United States Patent
Meulewaeter et al.

(10) Patent No.: US 10,202,613 B2
(45) Date of Patent: Feb. 12, 2019

(54) METHODS FOR ALTERING THE REACTIVITY OF PLANT CELL WALLS

(76) Inventors: Frank Meulewaeter, Merelbeke (BE); Bartel Vanholme, Oostakker (BE)

( * ) Notice: Subject to any disclaimer, the term of this patent is extended or adjusted under 35 U.S.C. 154(b) by 900 days.

(21) Appl. No.: 13/878,873

(22) PCT Filed: Sep. 30, 2011

(86) PCT No.: PCT/EP2011/004929
§ 371 (c)(1),
(2), (4) Date: Apr. 24, 2013

(87) PCT Pub. No.: WO2012/048807
PCT Pub. Date: Apr. 19, 2012

(65) Prior Publication Data
US 2013/0198976 A1    Aug. 8, 2013

Related U.S. Application Data

(60) Provisional application No. 61/394,109, filed on Oct. 18, 2010.

(30) Foreign Application Priority Data

Oct. 15, 2010  (EP) .................................. 10013693

(51) Int. Cl.
| | |
|---|---|
| C12N 15/54 | (2006.01) |
| C12N 15/82 | (2006.01) |
| A01H 5/00 | (2018.01) |
| C12N 9/10 | (2006.01) |
| A01H 5/10 | (2018.01) |
| D06P 3/66 | (2006.01) |

(52) U.S. Cl.
CPC ........... *C12N 15/8237* (2013.01); *A01H 5/00* (2013.01); *A01H 5/10* (2013.01); *C12N 9/1048* (2013.01); *C12N 9/1051* (2013.01); *C12N 15/8246* (2013.01); *C12Y 204/01* (2013.01); *D06P 3/66* (2013.01); *C07K 2319/01* (2013.01); *Y10T 428/249921* (2015.04)

(58) Field of Classification Search
CPC .......................... C12N 9/1051; C12N 15/8246
See application file for complete search history.

(56) References Cited

U.S. PATENT DOCUMENTS

| | | |
|---|---|---|
| 5,004,863 A | 4/1991 | Umbeck |
| 5,792,933 A | 8/1998 | Ma |
| 6,096,950 A | 8/2000 | John |
| 6,166,294 A | 12/2000 | Kasukabe et al. |
| 6,259,003 B1 | 7/2001 | Fujisawa et al. |
| 6,271,443 B1 | 8/2001 | Stalker et al. |
| 6,483,013 B1 | 11/2002 | Reynaerts et al. |
| 6,566,586 B1 | 5/2003 | Stalker et al. |
| 8,008,544 B2 * | 8/2011 | De Block .......... C12N 15/8246 435/320.1 |
| 2003/0106097 A1 | 6/2003 | Haigler et al. |
| 2003/0134120 A1 | 7/2003 | Kim et al. |
| 2009/0028837 A1 * | 1/2009 | De Block .......... C12N 15/8246 424/93.21 |

FOREIGN PATENT DOCUMENTS

| | | |
|---|---|---|
| WO | 1992/15675 | 9/1992 |
| WO | 1996/40924 | 12/1996 |
| WO | 1998/30698 | 7/1998 |
| WO | 2000/09729 | 2/2000 |
| WO | 2002/10377 | 2/2002 |
| WO | 2002/10413 | 2/2002 |
| WO | 2006/136351 | 12/2006 |
| WO | 2008/082969 | 7/2008 |
| WO | 2008/083969 | 7/2008 |
| WO | 2009/109315 | 9/2009 |

OTHER PUBLICATIONS

International Search Report for PCT Application No. PCT/EP2011/004929 dated Oct. 15, 2010.
Barny et al. The C-terminal domain of the Rltizobium /eguminosarum chitin synthase NodC is important for function and determines the orientation of the N-terminal region in the inner membrane1996, Molecular Microbiology, 19(3) 443-453.
Batista and Roberts, A novel, facile technique for deacetylating chitin1990, Makromolekulare Chemie—Macromolecular Chemistry and Physics, 191: 429-434.
Brandizzi et al., The Destination for Single-Pass Membrane Proteins Is Influenced Markedly by the Length of the Hydrophobic Domain 2002, Plant Cell, 14: 1077-1092.
Clough SJ and Bent AF, Floral dip: a simplified method for Agrobacterium-mediated transformation of *Arabidopsis thaliana*, The Plant Journal (1998) 16(6), 735-743.
Domard and Rinaudo, Preparation and characterization of fully deacetylated chitosan vol. 1 (1979)-1983, International Journal of Biological Macromolecules: structure, function and interactions, 5:49-52.
Essl et al. The N-terminal 77 amino acids from tobacco N-acetylglucosaminyltransferase I are su¤cient to retain a reporter protein in the Golgi apparatus of Nicotiana benthamiana cells, 1999, FEBS Lett., 453: 169-173.
Hood et al., The Hypervirulence of Agrobacterium tumefaciens A281 Is Encoded in a Region of pTiBo542 Outside of T-DNA, Department of Biology, Washington University, St. Louis, Missouri 631301; Ciba-Geigy Biotechnology Facility, Research Park, NC, Dec. 1986, p. 1291-1301.
Hou et al., SCFP, a novel fiber-specific promoter in cotton 2008, Chinese Science Bulletin, vol. 53, No. 17, 2639-2645.
Kamst et al., Rhizobium Nodulation Protein NodC Is an Important Determinant of Chitin Oligosaccharide Chain Length in Nod Factor Biosynthesis, Journal of Bacteriology, Apr. 1997, p. 2103-2108.
Kamst et al., Functional Domains in the Chitin Oligosaccharide Synthase NodC and Related B-Polysaccharide Synthases Trends in Glycoscience and Glycotechnology, vol. 11 No. 60 (Jul. 1999) pp. 187-199.

(Continued)

*Primary Examiner* — Lee A Visone

(57) ABSTRACT

Methods and means are provided to produce positively charged oligosaccharides in the plant cell wall by introducing into said plant cell a Nodulation C protein fused to a heterologous Golgi signal anchor sequence.

11 Claims, 7 Drawing Sheets

Specification includes a Sequence Listing.

(56) References Cited

OTHER PUBLICATIONS

Liu et al., Chitosan coated cotton fiber: preparation and physical properties, Carbohydrate Polymers, 44 (2001) 233-238.

Munro Sequences within and adjacent to the transmembrane segment of a-2,6-sialyltransferase specify Golgi retentionet al., 1991, EMBO Journal, vol. No. 12 pp. 3577-3588 1991.

No et al., Effective Deacetylation of Chitin under Conditions of 15 psi/121° C., 2000, Journal of Agricultural and Food Chemistry, 2000, 48: 2625-2627.

Pagny et al., Structural requirements for *Arabidopsis* β1,2-xylosyltransferase activity and targeting to the Golgi 2003, The Plant Journal, 33: 189-203.

Pelletier et al, Chitin/Chitosan Transformaion by Thermo-Mechano-Chemical Treatment Including Characterization by Enzymatic Depolymerization 1990, Biotechnol Bioeng., vol. 36 pp. 310-315.

Pu et al., The R2R3 MYB Transcription Factor GhMYB109 Is Required for Cotton Fiber Development 2008, Genetics, 180: 811-820.

Rao et al, Deacetylation of Chitin at Low Temperature by a Novel Alkali Impregnation Technique 1987, Indian Journal of Technology, vol. 25, Apr. 1987, pp. 194-196.

Rozaklis et al., Determination of Oligosaccharides in Pompe Disease by Electrospray Ionization Tandem Mass Spectrometry 2002, Clinical Chemistry, 48:1 131-139.

Saint-Jore et al., Redistribution of membrane proteins between the Golgi apparatus and endoplasmic reticulum in plants is reversible and not dependent on cytoskeletal networks 2002, The Plant Journal, 29(5) 661-678.

Ausubel, et al., Current Protocols in Molecular Biology, vol. 2, Published by Current ProtocolS WILEY LBS 487A4AO.

J. Sambrook et al., Molecular Cloning, Cold Spring Harbor Laboratory Press 1989.

R.R.D. Croy, Plant Molecular Biology LabFax, Department of Biological Sciences University of Durham, Science Laboratories, ISBN 1 872748 15 5. BIOS Scientific Publishers Limited, 1993.

\* cited by examiner

| | | | | | |
|---|---|---|---|---|---|
| ROT_NODC_RHILP | MTMLDTTSTV | AVSLYALLST | AYKSMQAVYS | LPTDVSLASH | GLGGFDELPS |
| ROT_NODC_BRAJA | MDLLATTSAA | AVSSYALLST | IYKSVQALYA | QPAINSSLDN | LGQAEVVVPA |
| ROT_NODC_RHIS3 | MDLLTTTSTV | AVACYALLST | VYKGMQAVYS | LPPTVAPASE | DLVGSDLWPS |
| ROT_NODC_RHISN | MDLLGTTGAV | AISLYAALST | AYKGMQAIYA | LPTNTTAAST | PVTGSGAPPS |
| ROT_NODC_RHILV | MTLLATTSIA | AISLYAMLST | VYKSAQVFHA | RRTTISTTPA | KDIETNPVPS |
| ROT_NODC_AZOCA | MSVVDVIGLL | ATAAYVTLAS | AYKVVQFIN. | VSSVTDVAGL | ESDALPLTPR |
| | M-------- | -A---Y---L-- | --YK--Q--- | ---------- | ----P---- |
| | | | | | |
| ROT_NODC_RHILP | VDVIVPSFNE | DPRTLSECLA | SIAGQEYGGR | LQVYLVDDGS | ENREALRLVH |
| ROT_NODC_BRAJA | VDVIVPCFNE | NPNTLAECLE | SIASQDYAGK | MQVYVVDDGS | ANRDVVAPVH |
| ROT_NODC_RHIS3 | VDVIIPCYNE | GPLTLSACLD | SIANQEYAGK | LRVYVVDDGS | GNRDAVIPIH |
| ROT_NODC_RHISN | VDVIVPCYNE | DPRALSACLA | SIAKQDYAGE | LRVYVVDDGS | GNRNAIIPVH |
| ROT_NODC_RHILV | VDVIVPCFNE | DPIVLSECLA | SLAEQDYAGK | LRIYVVDDGS | KNRDAVVAQR |
| ROT_NODC_AZOCA | VDVIVPTFNE | NSSTLLECVA | SICAQDYRGP | ITIVVVDDGS | TNKTSFHAVC |
| | VDVI-P--NE | -----L--C--- | S---Q-Y-G- | -----VDDGS | -N-------- |
| | | | | | |
| ROT_NODC_RHILP | EAFARDPRFN | ILLLPQNVGK | RKAQDRCDQR | SAGDMVLNVD | SDTILASDVI |
| ROT_NODC_BRAJA | RIYASDPRFS | FILLANNVGK | RKAQIAAIRS | SSGDLVLNVD | SDTILAADVV |
| ROT_NODC_RHIS3 | DNYAGDPRFD | FLLPENVGK | RKAQIAAIRR | SSGDLVLNVD | SDTTLASDVI |
| ROT_NODC_RHISN | DHYACDPRFR | FILMPKNVGK | RKAQIVAIRE | SSGDLILNVD | SDTTIAPDVV |
| ROT_NODC_RHILV | AAYADDERFN | FTILPKNVGK | RKA.IAAITQ | SGDLILNVD | SDTTIAPDVV |
| ROT_NODC_AZOCA | DKYASDERFI | FVELDQNKGT | A.AQMEAIRR | TDGDLIINVD | SDVIDKDVV |
| | ---A-D-R-- | F------N-G- | --A------ | --GD--LNVD | SDT-----DV- |
| | | | | | |
| ROT_NODC_RHILP | RKLVPKNARV | AVGR.MGQLT | GPQPKRQLAD | PFDDMEYWLA | CNEERSQQAR |
| ROT_NODC_BRAJA | TKLVLKMHDP | GIGAAMGQLI | ASNRNQTWLT | RLIDMEYWLA | CNEERAAQAR |
| ROT_NODC_RHIS3 | RKLARKMQDP | AIGAAMGQLT | ASNRSDTWLT | RLIDMEYWLA | CNEERAAQAR |
| ROT_NODC_RHISN | TKLALKMYSP | AVGAAMGQLT | ASNRSDTWLT | RLIDMEYWLA | CNEERAAQAR |
| ROT_NODC_RHILV | SKLAHKMRDP | AVGAAMGQMK | ASNQADTWLT | RLIDMEYWLA | CNEERAAQAR |
| ROT_NODC_AZOCA | TKLASSMRAP | NVGGVMGQLV | AKNRERSWLT | RLIDMEYWLA | CNEERIAQSR |
| | --KL------ | ---G--MGQ-- | --------- | ---DMEYWLA | CNEER--Q-R |
| | | | | | |
| ROT_NODC_RHILP | FGCVMFCSGS | CVMYRLVSA. | SLLDQYDAQY | FRKQR..FGE | .IDIHLSHAE |
| ROT_NODC_BRAJA | FGAVMCCCGP | CAMYRRSALA | LLLDQYEAQF | FRGKPSDFGE | DRHLTILMLK |
| ROT_NODC_RHIS3 | FGAVMCCCGP | CAMYRRSSLL | SLLDQYETQM | FRGKPSDFGE | DRHLTILMLE |
| ROT_NODC_RHISN | FGAVMCCCGP | CAMYRRSALL | LLLDKYETQL | FRGRPSDFGE | DRHLTILMLN |
| ROT_NODC_RHILV | FGAVMCCCGP | CAMYRRSAML | SLLDQYETQL | YRGKPSDFGE | DRHLTILMLS |
| ROT_NODC_AZOCA | FGSVMCCCGP | CAMYRRSAIT | PLLAEYEHQT | FLGRPSNFGE | DRHLTILMLK |
| | FG-VM-C-G- | C-MYR----- | --LL-Y---Q- | F------FGE | ---------- |

FIGURE 1

```
ROT_NODC_RHILP  GSFRTEYRPS AHAATVVPNK LGPYLGQQLR WARSTFRTTL LGAP.LPNLN
ROT_NODC_BRAJA  AGFRTEYVPD AIAATVVPHS LRPYLRQQLR WARSTFRDTF LAWRLLPELD
ROT_NODC_RHIS3  AGFRTEYVPD AIAVTVVPDR LGPYLRQQLR WARSTFRDTL LALRLLPGLD
ROT_NODC_RHISN  AGFRTEYVPE AIAATVVPNS MGAYLRQQLR WARSTFRDTL LALRLLPGLD
ROT_NODC_RHILV  AGFRTEYVPS AIAATVVPDT MGVYLRQQLR WARSTFRDTL LALPVLPGLD
ROT_NODC_AZOCA  AGFRTGYVPS AVARTLVPDG .SPYLRQQLR WARSTYRDTA LALRIKKNLS
                --FRT-Y-P- A-A-T-VP-- ----YL-QQLR WARST-R-T- L--------

ROT_NODC_RHILP  RFLMLDVVGQ NLGPLLLDHS VLTGLAQLAL TGTAPWLAAL MIVAMTIDRC
ROT_NODC_BRAJA  GYLTLDVIGQ NLGPLLLAIS SLAALAQLLI DGSIPWWTGL TIAAMTVRC
ROT_NODC_RHIS3  RYLTLDVVGQ NLGPLLLALS VIAGIAQFAL TATLPWPTIL VIAAMTIIRC
ROT_NODC_RHISN  RYLTLDVIGQ NLGPLLLALS VLTGLAQLAL TATVPWSTIL MIASMTMVRC
ROT_NODC_RHILV  RYLTLDAIGQ NVGLLLLALS VLTGIGQFAL TATLPWWTIL VIGSMTLVRC
ROT_NODC_AZOCA  KYITFEICAQ NLGTALLLVM TMISLSLTTS GSQTPVILLG VVVGMSIIRC
                ---------- N-G---LL-- ---------- ----P----- ----M---RC

ROT_NODC_RHILP  SVVALRARQL RFLGFSLHTF INIFLLLPLK AYALCTLSNI AWLSSLLCWQ
ROT_NODC_BRAJA  CVAALRAREL RFIGFSLHTP INICLLLPLK AYALCTLSNS DWLSRKVTDM
ROT_NODC_RHIS3  TVTACRARQA RFIGFSLHTF INIFLLLPLK AYALCTLSNS DWLSRKTATL
ROT_NODC_RHISN  GVAAFRAREL RFLGFSLHTL LNVALLLPLK AYALCTLSNS DWLSRGSPAA
ROT_NODC_RHILV  SVAAYRAREL RFLGFALHTL VNIFLLIPLK AYALCTLSNS DWLSRGSVAI
ROT_NODC_AZOCA  CSVALIAKDF RFLYFIVHSA LNVLILTPLK LYALLTIRDS RWLSRESS..
                ---------- RF-F----H-- -N---L-PLK -YAL-T---- -WLS------

ROT_NODC_RHILP  LESTSTADAR TT........ ....ECSDMR TASKLSPPPS CQANDV....
ROT_NODC_BRAJA  PTEEGKQPVI LHPNAGRSPA GVGGRLLLFV RRRYRSLHRA WRRRVFPVA
ROT_NODC_RHIS3  PNADKKQIIV ANPIAGVGTG SSGSAEAIRR TDLPRDSSKL VNADSVCSAE
ROT_NODC_RHISN  APNGVKDSPE PHC....... .......... .......... ..........
ROT_NODC_RHILV  APTVGQQGAT KMP....... .......... .......GR ATSEIAYSGE
ROT_NODC_AZOCA  .......... .......... .......... .......... ..........

ROT_NODC_RHILP  .......... .......... .......... .......... ..........
ROT_NODC_BRAJA  IVRLSTNKWS ADDSGRKPSV IRARVGCRRP VAPRH
ROT_NODC_RHIS3  .......... .......... .......... .....
ROT_NODC_RHISN  .......... .......... .......... .....
ROT_NODC_RHILV  .......... .......... .......... .....
ROT_NODC_AZOCA  .......... .......... .......... .....
```

FIGURE 1 CONTINUED

```
ROT_NODC_BRAJA    MDLLATTSAA AVSSYALLST IYKSVQALYA QPAINSSLDN LGQAEVVVPA
ROT_NODC_RHIS3    MDLLTTTSTV AVACYALLST VYKGMQAVYS LPPTVAPASE DLVGSDLWPS
ROT_NODC_RHISN    MDLLGTTGAV AISLYAALST AYKGMQAIYA LPTNTTAAST PVTGSGAPPS
ROT_NODC_RHILV    MTLLATTSIA AISLYAMLST VYKSAQVFHA RRTTISTTPA KDIETNPVPS
ROT_NODC_AZOCA    MSVVDVIGLL ATAAYVTLAS AYKVVQFIN. VSSVTDVAGL ESDALPLTPR
                  M--------- A----Y---L- --YK---Q-- ---------- --------P-

ROT_NODC_BRAJA    VDVIVPCFNE NPNTLAECLE SIASQDYAGK MQVYVVDDGS ANRDVVAPVH
ROT_NODC_RHIS3    VDVIIPCYNE GPLITLSACLD SIANQEYAGK LRVYVVDDGS GNRDAVIPIH
ROT_NODC_RHISN    VDVIVPCYNE DPRALSACLA SIAKQDYAGE LRVYVVDDGS GNRNAIIPVH
ROT_NODC_RHILV    VDVIVPCFNE DPIVLSECLA SLAEQDYAGK LRIYVVDDGS KNRDAVVAQR
ROT_NODC_AZOCA    VDVIVPTFNE NSSTLLECVA SICAQDYRGP ITIVVVDDGS TNKTSFHAVC
                  VDVI-P--NE -----L--C-- S----Q-Y-G- ----VVDDGS -N--------

ROT_NODC_BRAJA    RIYASDPRFS FILLANNVGK RKAQIAAIRS SSGDLVLNVD SDTILAADVV
ROT_NODC_RHIS3    DNYAGDPRFD FILLPENVGK RKAQIAAIRR SSGDLVLNVD SDTTLASDVI
ROT_NODC_RHISN    DHYACDPRFR FILMPKNVGK RKAQIVAIRE SSGDLVLNVD SDTTIAPDVV
ROT_NODC_RHILV    AAYADDEREN FTILPKNVGK RKA.IAAITQ SSGDLILNVD SDTTIAPDVV
ROT_NODC_AZOCA    DKYASDERFI FVELDQNKGT A.AQMEAIRR TDGDLILNVD SDTVIDKDVV
                  ---A-D-R-- F-----N-G- --A------- --GDL-LNVD SDT----DV-

ROT_NODC_BRAJA    TKLVLKMHDP GIGAAMGQLI ASNRNQTWLT RLIDMEYWLA CNEERAAQAR
ROT_NODC_RHIS3    RKLARKMQDP AIGAAMGQLT ASNRSDTWLT RLIDMEYWLA CNEERAAQAR
ROT_NODC_RHISN    TKLALKMYSP AVGAAMGQLT ASNRSDTWLT RLIDMEYWLA CNEERAAQAR
ROT_NODC_RHILV    SKLAHKMRDP AVGAAMGQMK ASNQADTWLT RLIDMEYWLA CNEERAAQAR
ROT_NODC_AZOCA    TKLASSMRAP NVGGVMGQLV AKNRERSWLT RLIDMEYWLA CNEERIAQSR
                  -KL----M--P --G---MGQ-- A-N-----WLT RLIDMEYWLA CNEER--Q-R

ROT_NODC_BRAJA    FGAVMCCCGP CAMYRRSALA LLLDQYEAQF FRGKPSDFGE DRHLTILMLK
ROT_NODC_RHIS3    FGAVMCCCGP CAMYRRSSLL SLLDQYETQM FRGKPSDFGE DRHLTILMLE
ROT_NODC_RHISN    FGAVMCCCGP CAMYRRSALL LLLDKYETQL FRGRPSDFGE DRHLTILMLN
ROT_NODC_RHILV    FGAVMCCCGP CAMYRRSAML SLLDQYETQL YRGKPSDFGE DRHLTILMLS
ROT_NODC_AZOCA    FGSVMCCCGP CAMYRRSAIT PLLAEYEHQT FLGRPSNFGE DRHLTILMLK
                  FG-VMCCCGP CAMYRRS--- --LL--YE-Q- F-G-PS-FGE DRHLTILML-
```

FIGURE 2

```
ROT_NODC_BRAJA    AGFRTEYVPD AIAATVVPHS LRPYLRQQLR WARSTFRDTF LAWRLLPELD
ROT_NODC_RHIS3    AGFRTEYVPD AIAVTVVPDR LGPYLRQQLR WARSTFRDTL LALRLLPGLD
ROT_NODC_RHISN    AGFRTEYVPE AIAATVVPNS MGAYLRQQLR WARSTFRDTL LALRLLPGLD
ROT_NODC_RHILV    AGFRTEYVPS AIAATVVPDT MGVYLRQQLR WARSTFRDTL LALPVLPGLD
ROT_NODC_AZOCA    AGFRTGYVPS AVARTIVPDG .SPYLRQQLR WARSTYRDTA LALRIKKNLS
                  AGFRT-YVP- A-A-T-VP-- ---YLRQQLR WARST-RDT- LA-------

ROT_NODC_BRAJA    GYLTLDVIGQ NLGPLLLAIS SLAALAQLLI DGSIPWWTGL TIAAMTVRC
ROT_NODC_RHIS3    RYLTLDVVGQ NLGPLLLALS VIAGIAQFAL TATLPWPTIL VIAAMTIIRC
ROT_NODC_RHISN    RYLTLDVIGQ NLGPLLLALS VLTGLAQLAL TATVPWSTIL MIASMTMVRC
ROT_NODC_RHILV    RYLTLDAIGQ NVGLLLLALS VLTGIGQFAL TATLPWWTIL VIGSMTLVRC
ROT_NODC_AZOCA    KYITFEICAQ NLGTALLLVM TMISLSLTTS GSQTPVIILG VVVGMSIIRC
                  -Y-T------Q N-G---LL-- ---------- ----P----- ---M---RC

ROT_NODC_BRAJA    CVAALRAREL RFIGFSLHTP INICLLLPLK AYALCTLSNS DWLSRKVTDM
ROT_NODC_RHIS3    TVTACRARQA RFIGFSLHTF INIFLLLPLK AYALCTLSNS DWLSRKTATL
ROT_NODC_RHISN    GVAAFRAREL RFLGFSLHTL LNVALLLPLK AYALCTLSNS DWLSRGSPAA
ROT_NODC_RHILV    SVAAYRAREL RELGFALHTL VNIFLLIPLK AYALCTLSNS DWLSRGSVAI
ROT_NODC_AZOCA    CSVALIAKDF RFLYFIVHSA LNVLILTPLK LYALLTIRDS RWLSRESS..
                  ---------- RF-FF--H-- -N---L-PLK -YAL-T---- -WLSR----

ROT_NODC_BRAJA    PTEEGKQPVI LHPNAGRSPA GVGGRLLLFV RRRYRSLHRA WRRRRVFPVA
ROT_NODC_RHIS3    PNADKKQIIV ANPIAGVGTG SSGSAEAIRR TDLPRDSSKL VNADSVCSAE
ROT_NODC_RHISN    APNGVKDSPE PHC.......
ROT_NODC_RHILV    APTVGQQGAT KMP....... .......... ........GR ATSEIAYSGE
ROT_NODC_AZOCA    .......... .......... .......... .......... ..........

ROT_NODC_BRAJA    IVRLSTNKWS ADDSGRKPSV IRARVGCRRP VAPRH
ROT_NODC_RHIS3    .......... .......... .......... .....
ROT_NODC_RHISN    .......... .......... .......... .....
ROT_NODC_RHILV    .......... .......... .......... .....
ROT_NODC_AZOCA    .......... .......... .......... .....
```

FIGURE 2 CONTINUED

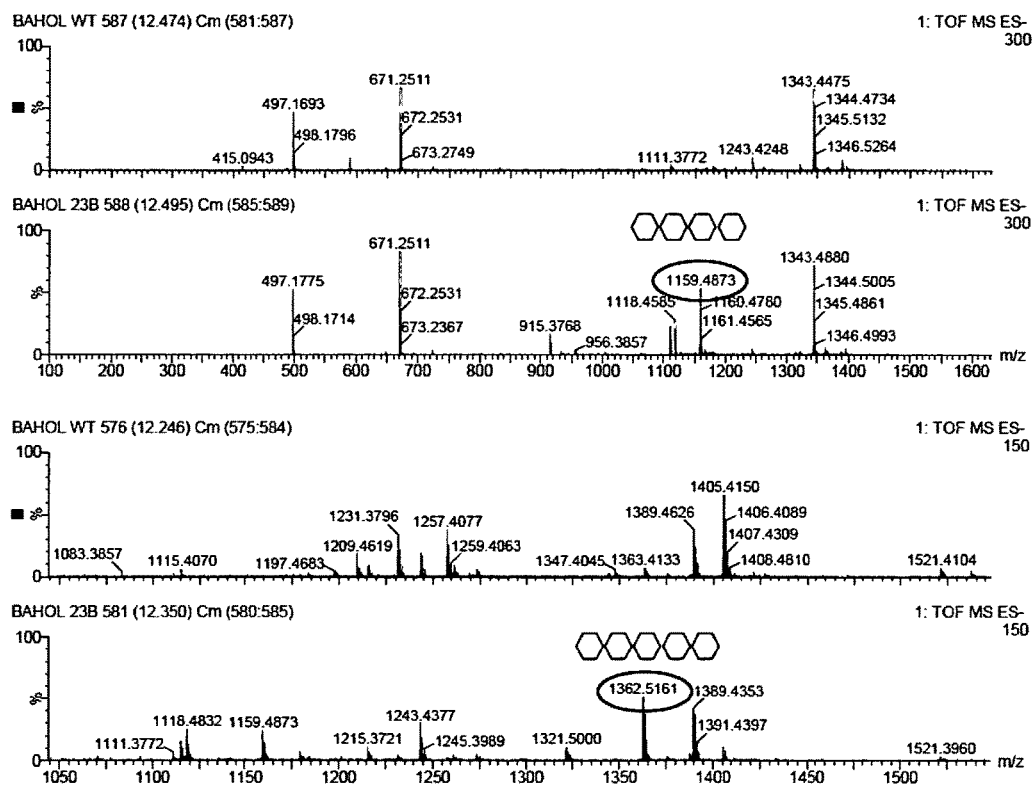
Figure 4, continued

SEQUENCE LISTING

```
<160> NUMBER OF SEQ ID NOS: 31

<210> SEQ ID NO 1
<211> LENGTH: 397
<212> TYPE: PRT
<213> ORGANISM: Azorhizobium caulinodans

<400> SEQUENCE: 1

Met Ser Val Val Asp Val Ile Gly Leu Leu Ala Thr Ala Ala Tyr Val
1               5                   10                  15

Thr Leu Ala Ser Ala Tyr Lys Val Val Gln Phe Ile Asn Val Ser Ser
            20                  25                  30

Val Thr Asp Val Ala Gly Leu Glu Ser Asp Ala Leu Pro Leu Thr Pro
        35                  40                  45

Arg Val Asp Val Ile Val Pro Thr Phe Asn Glu Asn Ser Ser Thr Leu
    50                  55                  60

Leu Glu Cys Val Ala Ser Ile Cys Ala Gln Asp Tyr Arg Gly Pro Ile
65                  70                  75                  80

Thr Ile Val Val Val Asp Asp Gly Ser Thr Asn Lys Thr Ser Phe His
                85                  90                  95

Ala Val Cys Asp Lys Tyr Ala Ser Asp Glu Arg Phe Ile Phe Val Glu
            100                 105                 110

Leu Asp Gln Asn Lys Gly Lys Arg Ala Ala Gln Met Glu Ala Ile Arg
        115                 120                 125

Arg Thr Asp Gly Asp Leu Ile Leu Asn Val Asp Ser Asp Thr Val Ile
    130                 135                 140

Asp Lys Asp Val Val Thr Lys Leu Ala Ser Ser Met Arg Ala Pro Asn
145                 150                 155                 160

Val Gly Gly Val Met Gly Gln Leu Val Ala Lys Asn Arg Glu Arg Ser
                165                 170                 175

Trp Leu Thr Arg Leu Ile Asp Met Glu Tyr Trp Leu Ala Cys Asn Glu
            180                 185                 190

Glu Arg Ile Ala Gln Ser Arg Phe Gly Ser Val Met Cys Cys Cys Gly
        195                 200                 205

Pro Cys Ala Met Tyr Arg Arg Ser Ala Ile Thr Pro Leu Leu Ala Glu
    210                 215                 220

Tyr Glu His Gln Thr Phe Leu Gly Arg Pro Ser Asn Phe Gly Glu Asp
225                 230                 235                 240

Arg His Leu Thr Ile Leu Met Leu Lys Ala Gly Phe Arg Thr Gly Tyr
                245                 250                 255
```

-continued

```
Val Pro Gly Ala Val Ala Arg Thr Leu Val Pro Asp Gly Leu Ala Pro
            260                 265                 270

Tyr Leu Arg Gln Gln Leu Arg Trp Ala Arg Ser Thr Tyr Arg Asp Thr
        275                 280                 285

Ala Leu Ala Leu Arg Ile Lys Lys Asn Leu Ser Lys Tyr Ile Thr Phe
    290                 295                 300

Glu Ile Cys Ala Gln Asn Leu Gly Thr Ala Leu Leu Leu Val Met Thr
305                 310                 315                 320

Met Ile Ser Leu Ser Leu Thr Thr Ser Gly Ser Gln Thr Pro Val Ile
                325                 330                 335

Ile Leu Gly Val Val Gly Met Ser Ile Ile Arg Cys Cys Ser Val
            340                 345                 350

Ala Leu Ile Ala Lys Asp Phe Arg Phe Leu Tyr Phe Ile Val His Ser
        355                 360                 365

Ala Leu Asn Val Leu Ile Leu Thr Pro Leu Lys Leu Tyr Ala Leu Leu
    370                 375                 380

Thr Ile Arg Asp Ser Arg Trp Leu Ser Arg Glu Ser Ser
385                 390                 395

<210> SEQ ID NO 2
<211> LENGTH: 485
<212> TYPE: PRT
<213> ORGANISM: Bradyrhizobium japonicum

<400> SEQUENCE: 2

Met Asp Leu Leu Ala Thr Thr Ser Ala Ala Val Ser Ser Tyr Ala
1               5                   10                  15

Leu Leu Ser Thr Ile Tyr Lys Ser Val Gln Ala Leu Tyr Ala Gln Pro
            20                  25                  30

Ala Ile Asn Ser Ser Leu Asp Asn Leu Gly Gln Ala Glu Val Val Val
        35                  40                  45

Pro Ala Val Asp Val Ile Val Pro Cys Phe Asn Glu Asn Pro Asn Thr
    50                  55                  60

Leu Ala Glu Cys Leu Glu Ser Ile Ala Ser Gln Asp Tyr Ala Gly Lys
65                  70                  75                  80

Met Gln Val Tyr Val Val Asp Asp Gly Ser Ala Asn Arg Asp Val Val
                85                  90                  95

Ala Pro Val His Arg Ile Tyr Ala Ser Asp Pro Arg Phe Ser Phe Ile
            100                 105                 110

Leu Leu Ala Asn Asn Val Gly Lys Arg Lys Ala Gln Ile Ala Ala Ile
        115                 120                 125

Arg Ser Ser Ser Gly Asp Leu Val Leu Asn Val Asp Ser Asp Thr Ile
    130                 135                 140

Leu Ala Ala Asp Val Val Thr Lys Leu Val Leu Lys Met His Asp Pro
145                 150                 155                 160

Gly Ile Gly Ala Ala Met Gly Gln Leu Ile Ala Ser Asn Arg Asn Gln
                165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
        195                 200                 205

Gly Pro Cys Ala Met Tyr Arg Arg Ser Ala Leu Ala Leu Leu Leu Asp
    210                 215                 220

Gln Tyr Glu Ala Gln Phe Phe Arg Gly Lys Pro Ser Asp Phe Gly Glu
```

```
            225                 230                 235                 240

Asp Arg His Leu Thr Ile Leu Met Leu Lys Ala Gly Phe Arg Thr Glu
                    245                 250                 255

Tyr Val Pro Asp Ala Ile Ala Thr Val Pro His Ser Leu Arg
                    260                 265                 270

Pro Tyr Leu Arg Gln Gln Leu Arg Trp Ala Arg Ser Thr Phe Arg Asp
                    275                 280                 285

Thr Phe Leu Ala Trp Arg Leu Leu Pro Glu Leu Asp Gly Tyr Leu Thr
                    290                 295                 300

Leu Asp Val Ile Gly Gln Asn Leu Gly Pro Leu Leu Ala Ile Ser
    305                 310                 315                 320

Ser Leu Ala Ala Leu Ala Gln Leu Leu Ile Asp Gly Ser Ile Pro Trp
                    325                 330                 335

Trp Thr Gly Leu Thr Ile Ala Ala Met Thr Thr Val Arg Cys Cys Val
                    340                 345                 350

Ala Ala Leu Arg Ala Arg Glu Leu Arg Phe Ile Gly Phe Ser Leu His
                    355                 360                 365

Thr Pro Ile Asn Ile Cys Leu Leu Leu Pro Leu Lys Ala Tyr Ala Leu
                    370                 375                 380

Cys Thr Leu Ser Asn Ser Asp Trp Leu Ser Arg Lys Val Thr Asp Met
    385                 390                 395                 400

Pro Thr Glu Glu Gly Lys Gln Pro Val Ile Leu His Pro Asn Ala Gly
                    405                 410                 415

Arg Ser Pro Ala Gly Val Gly Gly Arg Leu Leu Leu Phe Val Arg Arg
                    420                 425                 430

Arg Tyr Arg Ser Leu His Arg Ala Trp Arg Arg Arg Val Phe Pro
                    435                 440                 445

Val Ala Ile Val Arg Leu Ser Thr Asn Lys Trp Ser Ala Asp Asp Ser
                    450                 455                 460

Gly Arg Lys Pro Ser Val Ile Arg Ala Arg Val Gly Cys Arg Arg Pro
    465                 470                 475                 480

Val Ala Pro Arg His
                    485

<210> SEQ ID NO 3
<211> LENGTH: 433
<212> TYPE: PRT
<213> ORGANISM: Rhizobium galegae

<400> SEQUENCE: 3

Met Thr Leu Leu Glu Thr Ile Gly Ile Ala Ala Val Thr Leu His Ala
1               5                   10                  15

Leu Leu Ser Ala Ile Tyr Lys Ser Met Gln Ala Phe Tyr Ala Arg Lys
                20                  25                  30

Ala Ser Gly Ser Gln Pro Arg Ser Lys Asp Ile Asp Pro Ala Ala Leu
            35                  40                  45

Pro Ser Val Asp Ile Ile Val Pro Cys Phe Asn Glu Asp Pro Ala Ile
        50                  55                  60

Leu Ser Ala Cys Leu Ser Ser Leu Ala Gly Gln Asp Tyr Gly Gly Lys
65                  70                  75                  80

Leu Arg Ile Tyr Met Val Asp Asp Gly Ser Cys Asn Arg Glu Ala Ile
                85                  90                  95

Leu Pro Val His Asp Phe Tyr Thr Ser Asp Pro Arg Phe Glu Phe Leu
                100                 105                 110
```

-continued

```
Leu Leu Ser Lys Asn Val Gly Lys Arg Lys Ala Gln Ile Ala Ala Ile
            115                 120                 125
Glu Arg Ser Cys Gly Asp Leu Ile Leu Asn Val Asp Ser Asp Thr Ser
        130                 135                 140
Ile Ala Ser Asp Val Val Thr Leu Leu Val Glu Lys Met Arg Asp Ser
145                 150                 155                 160
Asp Val Gly Ala Ala Met Gly Gln Leu Lys Ala Ser Asn Arg Asp Lys
                165                 170                 175
Asn Leu Leu Thr Arg Leu Ile Asp Met Glu Tyr Trp Leu Ala Cys Asn
            180                 185                 190
Asp Glu Arg Ala Ala Gln Ala Arg Phe Gly Ala Val Met Cys Cys Cys
        195                 200                 205
Gly Pro Cys Ala Met Tyr Arg Arg Ser Ala Leu Leu Leu Leu Leu Asp
210                 215                 220
Gln Tyr Gln Thr Gln Leu Tyr Arg Gly Lys Pro Ser Asp Phe Gly Glu
225                 230                 235                 240
Asp Arg His Leu Thr Ile Leu Met Leu Ser Ala Gly Phe Arg Thr Glu
                245                 250                 255
Tyr Val Pro Glu Ala Ile Ala Lys Thr Val Val Pro Asp Arg Met Gly
            260                 265                 270
Ser Tyr Leu Arg Gln Gln Leu Arg Trp Ala Arg Ser Thr Phe Arg Asp
        275                 280                 285
Thr Leu Leu Ala Leu Pro Leu Leu Pro Ser His Asn Arg Phe Leu Thr
290                 295                 300
Leu Asp Ala Ile His Gln Asn Ile Gly Pro Leu Leu Leu Ala Val Ser
305                 310                 315                 320
Ser Ala Thr Gly Ile Thr Gln Phe Ile Leu Thr Ala Thr Val Pro Gly
                325                 330                 335
Trp Thr Ile Ile Ile Ile Ala Ser Met Thr Met Val Arg Cys Ser Val
            340                 345                 350
Ala Ala Tyr Arg Ser Arg Gln Ile Arg Phe Leu Ala Phe Ser Leu His
        355                 360                 365
Thr Leu Ile Asn Leu Phe Met Leu Ile Pro Leu Lys Gly Phe Ala Leu
370                 375                 380
Leu Thr Leu Ser Asn Ser Asp Trp Leu Ser Arg Gly Ser Thr Thr Asp
385                 390                 395                 400
Gly Pro Ala Ile Ala Glu Ser Asn Ala Ala Ser Asn Glu Ala Glu Ile
                405                 410                 415
Val Ala Ser Ala Ser Pro Phe Gly Gly Gly Thr Ser Trp Arg Phe Arg
            420                 425                 430
Arg
```

<210> SEQ ID NO 4
<211> LENGTH: 424
<212> TYPE: PRT
<213> ORGANISM: Rhizobium leguminosarum

<400> SEQUENCE: 4

```
Met Thr Leu Leu Ala Thr Thr Ser Ile Ala Ala Ile Ser Leu Tyr Ala
1               5                   10                  15
Met Leu Ser Thr Val Tyr Lys Ser Ala Gln Val Phe His Ala Arg Arg
                20                  25                  30
Thr Thr Ile Ser Thr Thr Pro Ala Lys Asp Ile Glu Thr Asn Pro Val
            35                  40                  45
```

Pro Ser Val Asp Val Ile Val Pro Cys Phe Asn Glu Asp Pro Ile Val
        50                  55                  60

Leu Ser Glu Cys Leu Ala Ser Leu Ala Glu Gln Asp Tyr Ala Gly Lys
65                  70                  75                  80

Leu Arg Ile Tyr Val Val Asp Asp Gly Ser Lys Asn Arg Asp Ala Val
                85                  90                  95

Val Ala Gln Arg Ala Ala Tyr Ala Asp Asp Glu Arg Phe Asn Phe Thr
                100                 105                 110

Ile Leu Pro Lys Asn Val Gly Lys Arg Lys Ala Ile Ala Ala Ile Thr
            115                 120                 125

Gln Ser Ser Gly Asp Leu Ile Leu Asn Val Asp Ser Asp Thr Thr Ile
130                 135                 140

Ala Pro Asp Val Val Ser Lys Leu Ala His Lys Met Arg Asp Pro Ala
145                 150                 155                 160

Val Gly Ala Ala Met Gly Gln Met Lys Ala Ser Asn Gln Ala Asp Thr
                165                 170                 175

Trp Leu Thr Arg Leu Ile Asp Met Glu Tyr Trp Leu Ala Cys Asn Glu
            180                 185                 190

Glu Arg Ala Ala Gln Ala Arg Phe Gly Ala Val Met Cys Cys Cys Gly
        195                 200                 205

Pro Cys Ala Met Tyr Arg Arg Ser Ala Met Leu Ser Leu Leu Asp Gln
210                 215                 220

Tyr Glu Thr Gln Leu Tyr Arg Gly Lys Pro Ser Asp Phe Gly Glu Asp
225                 230                 235                 240

Arg His Leu Thr Ile Leu Met Leu Ser Ala Gly Phe Arg Thr Glu Tyr
                245                 250                 255

Val Pro Ser Ala Ile Ala Ala Thr Val Val Pro Asp Thr Met Gly Val
            260                 265                 270

Tyr Leu Arg Gln Gln Leu Arg Trp Ala Arg Ser Thr Phe Arg Asp Thr
        275                 280                 285

Leu Leu Ala Leu Pro Val Leu Pro Gly Leu Asp Arg Tyr Leu Thr Leu
290                 295                 300

Asp Ala Ile Gly Gln Asn Val Gly Leu Leu Leu Ala Leu Ser Val
305                 310                 315                 320

Leu Thr Gly Ile Gly Gln Phe Ala Leu Thr Ala Thr Leu Pro Trp Trp
                325                 330                 335

Thr Ile Leu Val Ile Gly Ser Met Thr Leu Val Arg Cys Ser Val Ala
            340                 345                 350

Ala Tyr Arg Ala Arg Glu Leu Arg Phe Leu Gly Phe Ala Leu His Thr
        355                 360                 365

Leu Val Asn Ile Phe Leu Leu Ile Pro Leu Lys Ala Tyr Ala Leu Cys
370                 375                 380

Thr Leu Ser Asn Ser Asp Trp Leu Ser Arg Gly Ser Val Ala Ile Ala
385                 390                 395                 400

Pro Thr Val Gly Gln Gln Gly Ala Thr Lys Met Pro Gly Arg Ala Thr
                405                 410                 415

Ser Glu Ile Ala Tyr Ser Gly Glu
                420

<210> SEQ ID NO 5
<211> LENGTH: 426
<212> TYPE: PRT
<213> ORGANISM: Rhizobium meliloti

<400> SEQUENCE: 5

```
Met Tyr Leu Leu Asp Thr Thr Ser Thr Ala Ala Ile Ser Ile Tyr Ala
1               5                   10                  15

Leu Leu Leu Thr Ala Tyr Arg Ser Met Gln Val Leu Tyr Ala Arg Pro
            20                  25                  30

Ile Asp Gly Pro Ala Val Ala Ala Glu Pro Val Glu Thr Arg Pro Leu
            35                  40                  45

Pro Ala Val Asp Val Ile Val Pro Ser Phe Asn Glu Asp Pro Gly Ile
50                  55                  60

Leu Ser Ala Cys Leu Ala Ser Ile Ala Asp Gln Asp Tyr Pro Gly Glu
65                  70                  75                  80

Leu Arg Val Tyr Val Asp Asp Gly Ser Arg Asn Arg Glu Ala Ile
                85                  90                  95

Val Arg Val Arg Ala Phe Tyr Ser Arg Asp Pro Arg Phe Ser Phe Ile
                100                 105                 110

Leu Leu Pro Glu Asn Val Gly Lys Arg Lys Ala Gln Ile Ala Ala Ile
            115                 120                 125

Gly Gln Ser Ser Gly Asp Leu Val Leu Asn Val Asp Ser Asp Ser Thr
        130                 135                 140

Ile Ala Phe Asp Val Val Ser Lys Leu Ala Ser Lys Met Arg Asp Pro
145                 150                 155                 160

Glu Val Gly Ala Val Met Gly Gln Leu Thr Ala Ser Asn Ser Gly Asp
                165                 170                 175

Thr Trp Leu Thr Lys Leu Ile Asp Met Glu Tyr Trp Leu Ala Cys Asn
            180                 185                 190

Glu Glu Arg Ala Ala Gln Ser Arg Phe Gly Ala Val Met Cys Cys Cys
            195                 200                 205

Gly Pro Cys Ala Met Tyr Arg Arg Ser Ala Leu Ala Ser Leu Leu Asp
        210                 215                 220

Gln Tyr Glu Thr Gln Leu Phe Arg Gly Lys Pro Ser Asp Phe Gly Glu
225                 230                 235                 240

Asp Arg His Leu Thr Ile Leu Met Leu Lys Ala Gly Phe Arg Thr Glu
            245                 250                 255

Tyr Val Pro Asp Ala Ile Val Ala Thr Val Pro Asp Thr Leu Lys
                260                 265                 270

Pro Tyr Leu Arg Gln Gln Leu Arg Trp Ala Arg Ser Thr Phe Arg Asp
        275                 280                 285

Thr Phe Leu Ala Leu Pro Leu Leu Arg Gly Leu Ser Pro Phe Leu Ala
    290                 295                 300

Phe Asp Ala Val Gly Gln Asn Ile Gly Gln Leu Leu Ala Leu Ser
305                 310                 315                 320

Val Val Thr Gly Leu Ala His Leu Ile Met Thr Ala Thr Val Pro Trp
            325                 330                 335

Trp Thr Ile Leu Ile Ile Ala Cys Met Thr Ile Ile Arg Cys Ser Val
            340                 345                 350

Val Ala Leu His Ala Arg Gln Leu Arg Phe Leu Gly Phe Val Leu His
            355                 360                 365

Thr Pro Ile Asn Leu Phe Leu Ile Leu Pro Leu Lys Ala Tyr Ala Leu
    370                 375                 380

Cys Thr Leu Ser Asn Ser Asp Trp Leu Ser Arg Tyr Ser Ala Pro Glu
385                 390                 395                 400

Val Pro Val Ser Gly Gly Lys Gln Thr Pro Ile Gln Thr Ser Gly Arg
                405                 410                 415
```

```
Val Thr Pro Asp Cys Thr Cys Ser Gly Glu
            420                 425

<210> SEQ ID NO 6
<211> LENGTH: 452
<212> TYPE: PRT
<213> ORGANISM: Rhizobium tropici

<400> SEQUENCE: 6

Met Asn Leu Leu Asp Ala Thr Ser Thr Ala Ala Ile Ser Leu Tyr Ala
1               5                   10                  15

Met Leu Ser Thr Ala Tyr Lys Ser Met Gln Val Val Tyr Ala Arg Pro
            20                  25                  30

Ile Glu Glu Pro Ser Thr Ser Ala Glu Pro Ile Ala Ser Ala Gln Trp
        35                  40                  45

Pro Ser Val Asp Val Ile Ile Pro Ser Phe Asn Glu Asp Pro Gly Thr
    50                  55                  60

Leu Trp Asp Cys Leu Glu Ser Ile Ala His Glu Glu Tyr Ala Gly Asp
65                  70                  75                  80

Leu Asn Val Tyr Val Val Asp Asp Gly Ser Ser Asn Arg Asp Ala Ile
                85                  90                  95

Thr Pro Val His Thr Ala Phe Ala Arg Asp Pro Arg Phe Thr Phe Ile
            100                 105                 110

Leu Leu Arg Lys Asn Val Gly Lys Arg Lys Ala Gln Ile Ala Ala Ile
        115                 120                 125

Arg Arg Ser Ser Gly Asp Leu Val Leu Asn Val Asp Ser Asp Thr Ile
    130                 135                 140

Leu Ala Pro Asp Val Val Val Lys Leu Ala Leu Lys Met Gln Asp Pro
145                 150                 155                 160

Ala Ile Gly Ala Ala Met Gly Gln Leu Ala Ala Ser Asn Arg His Glu
                165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
        195                 200                 205

Gly Pro Cys Ala Met Tyr Arg Arg Thr Ala Leu Thr Met Leu Leu Asp
    210                 215                 220

Gln Tyr Glu Thr Gln Met Phe Arg Gly Lys Arg Ser Asp Phe Gly Glu
225                 230                 235                 240

Asp Arg His Leu Thr Ile Leu Met Leu Lys Ala Gly Phe Arg Thr Glu
                245                 250                 255

Tyr Val Pro Thr Ala Ile Ala Ala Thr Val Val Pro Asn Lys Leu Arg
            260                 265                 270

Pro Tyr Leu Arg Gln Gln Leu Arg Trp Ala Arg Ser Thr Phe Arg Asp
        275                 280                 285

Thr Leu Leu Ala Met Asn Leu Leu Pro Gly Leu Asp Arg Phe Leu Thr
    290                 295                 300

Leu Asp Val Ile Gly Gln Asn Leu Gly Pro Leu Leu Leu Ala Leu Ser
305                 310                 315                 320

Val Leu Thr Gly Leu Ala Gln Phe Ala Leu Thr Gly Thr Val Pro Trp
                325                 330                 335

Trp Thr Cys Leu Met Ile Ala Ser Met Thr Met Ile Arg Cys Ser Val
            340                 345                 350

Ala Ala Val Arg Ala Arg Gln Phe Arg Phe Ile Gly Phe Ser Leu His
        355                 360                 365
```

```
Thr Phe Ile Asn Ile Phe Phe Leu Leu Pro Leu Lys Ala Tyr Ala Leu
    370             375                 380

Cys Thr Leu Ser Asn Ser Asp Trp Leu Ser Arg Gly Ser Ala Ala Lys
385             390                 395                 400

Ala Thr Gly Lys Gly Lys Leu Asp Ala Ile Gln Asp Pro Val Ala
                405             410                 415

Ala Ser Ser Pro Arg Glu Ser Gln Glu Asn Glu Ala Pro Leu Arg Arg
                420                 425                 430

His Asn Leu Ala Arg Asp Ala Thr Arg Ser Met Ala Tyr Asp Gly Ile
            435                 440                 445

Cys Thr Asp Gln
            450

<210> SEQ ID NO 7
<211> LENGTH: 428
<212> TYPE: PRT
<213> ORGANISM: Rhizobium leguminosarum

<400> SEQUENCE: 7

Met Thr Met Leu Asp Thr Thr Ser Thr Val Ala Val Ser Leu Tyr Ala
1               5                   10                  15

Leu Leu Ser Thr Ala Tyr Lys Ser Met Gln Ala Val Tyr Ser Leu Pro
                20                  25                  30

Thr Asp Val Ser Leu Ala Ser His Gly Leu Gly Gly Phe Asp Glu Leu
            35                  40                  45

Pro Ser Val Asp Val Ile Val Pro Ser Phe Asn Glu Asp Pro Arg Thr
    50                  55                  60

Leu Ser Glu Cys Leu Ala Ser Ile Ala Gly Gln Glu Tyr Gly Gly Arg
65                  70                  75                  80

Leu Gln Val Tyr Leu Val Asp Asp Gly Ser Glu Asn Arg Glu Ala Leu
                85                  90                  95

Arg Leu Val His Glu Ala Phe Ala Arg Asp Pro Arg Phe Asn Ile Leu
            100                 105                 110

Leu Leu Pro Gln Asn Val Gly Lys Arg Lys Ala Gln Asp Arg Cys Asp
        115                 120                 125

Gln Arg Ser Ala Gly Asp Met Val Leu Asn Val Asp Ser Asp Thr Ile
    130                 135                 140

Leu Ala Ser Asp Val Ile Arg Lys Leu Val Pro Lys Asn Ala Arg Val
145                 150                 155                 160

Ala Val Gly Arg Met Gly Gln Leu Thr Gly Pro Gln Pro Lys Arg Gln
                165                 170                 175

Leu Ala Asp Pro Phe Asp Asp Met Glu Tyr Trp Leu Ala Cys Asn Glu
            180                 185                 190

Glu Arg Ser Gln Gln Ala Arg Phe Gly Cys Val Met Phe Cys Ser Gly
        195                 200                 205

Ser Cys Val Met Tyr Arg Leu Val Ser Ala Ser Leu Leu Asp Gln Tyr
    210                 215                 220

Asp Ala Gln Tyr Phe Arg Lys Gln Arg Phe Gly Glu Ile Asp Ile His
225                 230                 235                 240

Leu Ser His Ala Glu Gly Ser Phe Arg Thr Glu Tyr Arg Pro Ser Ala
                245                 250                 255

His Ala Ala Thr Val Val Pro Asn Lys Leu Gly Pro Tyr Leu Gly Gln
            260                 265                 270

Gln Leu Arg Trp Ala Arg Ser Thr Phe Arg Thr Thr Leu Leu Gly Ala
```

```
                275                 280                 285
Pro Leu Pro Asn Leu Asn Arg Phe Leu Met Leu Asp Val Val Gly Gln
        290                 295                 300
Asn Leu Gly Pro Leu Leu Leu Asp His Ser Val Leu Thr Gly Leu Ala
305                 310                 315                 320
Gln Leu Ala Leu Thr Gly Thr Ala Pro Trp Leu Ala Ala Leu Met Ile
                325                 330                 335
Val Ala Met Thr Ile Asp Arg Cys Ser Val Val Ala Leu Arg Ala Arg
                340                 345                 350
Gln Leu Arg Phe Leu Gly Phe Ser Leu His Thr Phe Ile Asn Ile Phe
                355                 360                 365
Leu Leu Leu Pro Leu Lys Ala Tyr Ala Leu Cys Thr Leu Ser Asn Ile
        370                 375                 380
Ala Trp Leu Ser Ser Leu Leu Cys Trp Gln Leu Glu Ser Thr Ser Thr
385                 390                 395                 400
Ala Asp Ala Arg Thr Thr Glu Cys Ser Asp Met Arg Thr Ala Ser Lys
                405                 410                 415
Leu Ser Pro Pro Ser Cys Gln Ala Asn Asp Val
        420                 425

<210> SEQ ID NO 8
<211> LENGTH: 450
<212> TYPE: PRT
<213> ORGANISM: Rhizobium sp.

<400> SEQUENCE: 8

Met Asp Leu Leu Thr Thr Thr Ser Thr Val Ala Val Ala Cys Tyr Ala
1               5                   10                  15
Leu Leu Ser Thr Val Tyr Lys Gly Met Gln Ala Val Tyr Ser Leu Pro
                20                  25                  30
Pro Thr Val Ala Pro Ala Ser Glu Asp Leu Val Gly Ser Asp Leu Trp
            35                  40                  45
Pro Ser Val Asp Val Ile Ile Pro Cys Tyr Asn Glu Gly Pro Leu Thr
        50                  55                  60
Leu Ser Ala Cys Leu Asp Ser Ile Ala Asn Gln Glu Tyr Ala Gly Lys
65                  70                  75                  80
Leu Arg Val Tyr Val Asp Asp Gly Ser Gly Asn Arg Asp Ala Val
                85                  90                  95
Ile Pro Ile His Asp Asn Tyr Ala Gly Asp Pro Arg Phe Asp Phe Ile
                100                 105                 110
Leu Leu Pro Glu Asn Val Gly Lys Arg Lys Ala Gln Ile Ala Ala Ile
            115                 120                 125
Arg Arg Ser Ser Gly Asp Leu Val Leu Asn Val Asp Ser Asp Thr Thr
        130                 135                 140
Leu Ala Ser Asp Val Ile Arg Lys Leu Ala Arg Lys Met Gln Asp Pro
145                 150                 155                 160
Ala Ile Gly Ala Ala Met Gly Gln Leu Thr Ala Ser Asn Arg Ser Asp
                165                 170                 175
Thr Trp Leu Thr Arg Leu Ile Asp Met Glu Tyr Trp Leu Ala Cys Asn
                180                 185                 190
Glu Glu Arg Ala Ala Gln Ala Arg Phe Gly Ala Val Met Cys Cys Cys
            195                 200                 205
Gly Pro Cys Ala Met Tyr Arg Arg Ser Ser Leu Leu Ser Leu Leu Asp
        210                 215                 220
```

-continued

Gln Tyr Glu Thr Gln Met Phe Arg Gly Lys Pro Ser Asp Phe Gly Glu
225                 230                 235                 240

Asp Arg His Leu Thr Ile Leu Met Leu Glu Ala Gly Phe Arg Thr Glu
            245                 250                 255

Tyr Val Pro Asp Ala Ile Ala Val Thr Val Val Pro Asp Arg Leu Gly
        260                 265                 270

Pro Tyr Leu Arg Gln Gln Leu Arg Trp Ala Arg Ser Thr Phe Arg Asp
    275                 280                 285

Thr Leu Leu Ala Leu Arg Leu Leu Pro Gly Leu Asp Arg Tyr Leu Thr
290                 295                 300

Leu Asp Val Val Gly Gln Asn Leu Gly Pro Leu Leu Leu Ala Leu Ser
305                 310                 315                 320

Val Ile Ala Gly Ile Ala Gln Phe Ala Leu Thr Ala Thr Leu Pro Trp
            325                 330                 335

Pro Thr Ile Leu Val Ile Ala Ala Met Thr Ile Ile Arg Cys Thr Val
        340                 345                 350

Thr Ala Cys Arg Ala Arg Gln Ala Arg Phe Ile Gly Phe Ser Leu His
    355                 360                 365

Thr Phe Ile Asn Ile Phe Leu Leu Leu Pro Leu Lys Ala Tyr Ala Leu
370                 375                 380

Cys Thr Leu Ser Asn Ser Asp Trp Leu Ser Arg Lys Thr Ala Thr Leu
385                 390                 395                 400

Pro Asn Ala Asp Lys Lys Gln Ile Ile Val Ala Asn Pro Ile Ala Gly
            405                 410                 415

Val Gly Thr Gly Ser Ser Gly Ser Ala Glu Ala Ile Arg Arg Thr Asp
        420                 425                 430

Leu Pro Arg Asp Ser Ser Lys Leu Val Asn Ala Asp Ser Val Cys Ser
    435                 440                 445

Ala Glu
450

<210> SEQ ID NO 9
<211> LENGTH: 424
<212> TYPE: PRT
<213> ORGANISM: Rhizobium loti

<400> SEQUENCE: 9

Met Asn Leu Phe Ala Ser Ala Ser Thr Val Ala Ile Cys Ser Tyr Ala
1               5                   10                  15

Leu Leu Ser Thr Val Tyr Lys Thr Ala Gln Val Phe Tyr Thr Leu Pro
            20                  25                  30

Thr Asn Val Pro Pro Thr Ser Gly Asp Pro Pro Ser Gly Glu Pro Trp
        35                  40                  45

Pro Ser Val Asp Val Ile Ile Pro Cys Tyr Asn Glu Ala Pro Arg Thr
    50                  55                  60

Leu Ser Asp Cys Leu Ala Ser Ile Ala Ser Gln Asp Tyr Ala Gly Lys
65                  70                  75                  80

Leu Gln Val Tyr Val Val Asp Asp Gly Ser Ala Asn Arg Asp Ala Leu
                85                  90                  95

Val Gly Val His Glu Glu Tyr Ala Gly Asp Pro Arg Phe Asn Phe Val
            100                 105                 110

Ala Leu Pro Lys Asn Val Gly Lys Arg Lys Ala Gln Ile Ala Ala Ile
        115                 120                 125

Arg Arg Ser Cys Gly Asp Leu Val Leu Asn Val Asp Ser Asp Thr Ile
    130                 135                 140

```
Leu Ala Pro Asp Val Ile Thr Arg Leu Ala Leu Lys Met Gln Asp Gln
145                 150                 155                 160

Ala Val Gly Ala Ala Met Gly Gln Leu Ala Ala Ser Asn Arg Ser Glu
                165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
        195                 200                 205

Gly Pro Cys Ala Met Tyr Arg Arg Ser Ala Leu Val Ser Leu Leu Asp
    210                 215                 220

Gln Tyr Glu Thr Gln Arg Phe Arg Gly Lys Pro Ser Asp Phe Gly Glu
225                 230                 235                 240

Asp Arg His Leu Thr Ile Leu Met Leu Lys Ala Gly Phe Arg Thr Glu
                245                 250                 255

Tyr Val Pro Glu Ala Val Ala Ala Thr Val Val Pro Asn Ser Met Gly
                260                 265                 270

Pro Tyr Leu Arg Gln Gln Leu Arg Trp Ala Arg Ser Thr Phe Arg Asp
            275                 280                 285

Thr Leu Leu Ala Phe Gln Leu Leu Arg Gly Leu Asn Ile Tyr Leu Thr
290                 295                 300

Leu Asp Val Ile Gly Gln Asn Ile Gly Pro Leu Leu Leu Ser Leu Ser
305                 310                 315                 320

Ile Leu Ala Gly Leu Ala Gln Phe Val Thr Thr Gly Thr Val Pro Trp
                325                 330                 335

Thr Ala Cys Leu Met Ile Ala Ala Met Thr Ile Val Arg Cys Ser Val
            340                 345                 350

Ala Ala Phe Arg Ala Arg Gln Leu Arg Phe Leu Gly Phe Ser Leu His
        355                 360                 365

Thr Leu Ile Asn Ile Phe Leu Leu Leu Pro Leu Lys Ala Tyr Ala Leu
    370                 375                 380

Cys Thr Leu Ser Asn Ser Asp Trp Leu Ser Arg Ser Ser Ala Ala Asn
385                 390                 395                 400

Val Gln Asp Thr Gly Asp Ala Leu Pro Lys Pro Asn Leu Val Gly Ser
                405                 410                 415

Asp Ala Ala Tyr Ser Glu Gln Gln
            420

<210> SEQ ID NO 10
<211> LENGTH: 3971
<212> TYPE: DNA
<213> ORGANISM: Artificial
<220> FEATURE:
<223> OTHER INFORMATION: T-DNA of pTJN6
<220> FEATURE:
<221> NAME/KEY: misc_feature
<222> LOCATION: (1)..(25)
<223> OTHER INFORMATION: Left T-DNA border (complement)
<220> FEATURE:
<221> NAME/KEY: terminator
<222> LOCATION: (56)..(316)
<223> OTHER INFORMATION: 3' nos: 3'UTR from nopaline synthase gene of
      T-DNA pTiT37 (complement)
<220> FEATURE:
<221> NAME/KEY: misc_feature
<222> LOCATION: (336)..(887)
<223> OTHER INFORMATION: bar: coding sequence of phosphinotricin acetyl
      transferease of Streptomyces hygroscopicus (complement)
<220> FEATURE:
<221> NAME/KEY: promoter
<222> LOCATION: (888)..(1720)
```

```
<223> OTHER INFORMATION: P35S3: Promoter region from CaMV35S gene
      (complement)
<220> FEATURE:
<221> NAME/KEY: promoter
<222> LOCATION: (1769)..(2303)
<223> OTHER INFORMATION: P35S2: Promoter region from CaMV35S gene
<220> FEATURE:
<221> NAME/KEY: 5'UTR
<222> LOCATION: (2304)..(2368)
<223> OTHER INFORMATION: 5'cab22L: untranslated leader sequence of
      cab22L gene from Petunia
<220> FEATURE:
<221> NAME/KEY: misc_feature
<222> LOCATION: (2369)..(2474)
<223> OTHER INFORMATION: XylT: sequence coding for 35 N-terminal amino
      acids of beta-1,2- xylosyltransferase from Arabidopsis thaliana
<220> FEATURE:
<221> NAME/KEY: misc_feature
<222> LOCATION: (2475)..(3664)
<223> OTHER INFORMATION: NodC coding region from A.caulinodans
<220> FEATURE:
<221> NAME/KEY: terminator
<222> LOCATION: (3666)..(3914)
<223> OTHER INFORMATION: 3'35S: 3' untranslated region from the CaMV35S
      gene
<220> FEATURE:
<221> NAME/KEY: misc_feature
<222> LOCATION: (3947)..(3971)
<223> OTHER INFORMATION: RB: right T-DNA border (synthetic) (complement)

<400> SEQUENCE: 10
cggcaggata tattcaattg taaatggctc catggcgatc gctctagagg atctgcgatc      60
tagtaacata gatgacaccg cgcgcgataa tttatcctag tttgcgcgct atattttgtt     120
ttctatcgcg tattaaatgt ataattgcgg gactctaatc ataaaaaccc atctcataaa     180
taacgtcatg cattacatgt taattattac atgcttaacg taattcaaca gaaattatat     240
gataatcatc gcaagaccgg caacaggatt caatcttaag aaactttatt gccaaatgtt     300
tgaacgatct gcttcggatc ctagaacgcg tgatctcaga tctcggtgac gggcaggacc     360
ggacggggcg gtaccggcag gctgaagtcc agctgccaga aacccacgtc atgccagttc     420
ccgtgcttga agccggccgc ccgcagcatg ccgcggggg catatccgag cgcctcgtgc      480
atgcgcacgc tcgggtcgtt gggcagcccg atgacagcga ccacgctctt gaagccctgt     540
gcctccaggg acttcagcag gtgggtgtag agcgtggagc ccagtcccgt ccgctggtgg     600
cggggggaga cgtacacggt cgactcggcc gtccagtcgt aggcgttgcg tgccttccag     660
gggcccgcgt aggcgatgcc ggcgacctcg ccgtccacct cggcgacgag ccagggatag     720
cgctcccgca gacggacgag gtcgtccgtc cactcctgcg gttcctgcgg ctcggtacgg     780
aagttgaccg tgcttgtctc gatgtagtgg ttgacgatgg tgcagaccgc cggcatgtcc     840
gcctcggtgg cacggcggat gtcggccggg cgtcgttctg ggtccatggt tatagagaga     900
gagatagatt tatagagaga gactggtgat ttcagcgtgt cctctccaaa tgaaatgaac     960
ttccttatat agaggaaggg tcttgcgaag gatagtggga ttgtgcgtca tcccttacgt    1020
cagtggagat gtcacatcaa tccacttgct ttgaagacgg ggttggaacg tcttcttttt    1080
ccacgatgct cctcgtgggt gggggtccat ctttgggacc actgtcggca gaggcatctt    1140
gaatgatagc ctttccttta tcgcaatgat ggcatttgta ggagccacct tccttttcta    1200
ctgtcctttc gatgaagtga cagatagctg ggcaatggaa tccgaggagg tttcccgaaa    1260
ttatcctttg ttgaaaagtc tcaatagccc tttggtcttc tgagactgta tctttgacat    1320
ttttggagta gaccagagtg tcgtgctcca ccatgttgac gaagatttc ttcttgtcat    1380 tgagtcgtaa aagactctgt atgaactgtt cgccagtctt cacggcgagt tctgttagat    1440
```

```
cctcgatttg aatcttagac tccatgcatg gccttagatt cagtaggaac tacctttta     1500
gagactccaa tctctattac ttgccttggt ttatgaagca agccttgaat cgtccatact    1560
ggaatagtac ttctgatctt gagaaatatg tctttctctg tgttcttgat gcaattagtc    1620
ctgaatcttt tgactgcatc tttaaccttc ttgggaaggt atttgatctc ctggagattg    1680
ttactcgggt agatcgtctt gatgagacct gctgcgtagg aacgcggccg ctgtacaggg    1740
cccgggcata tggcgcgcca tatgcaccat acatggagtc aaaaattcag atcgaggatc    1800
taacagaact cgccgtgaag actggcgaac agttcataca gagtctttta cgactcaatg    1860
acaagaagaa aatcttcgtc aacatggtgg agcacgacac tctcgtctac tccaagaata    1920
tcaaagatac agtctcagaa gaccaaaggg ctattgagac ttttcaacaa agggtaatat    1980
cgggaaacct cctcggattc cattgcccag ctatctgtca cttcatcaaa aggacagtag    2040
aaaaggaagg tggcacctac aaatgccatc attgcgataa aggaaaggct atcgttcaag    2100
atgcccctgc cgacagtggt cccaaagatg accccccacc cacgaggagc atcgtggaaa    2160
aagaagacgt tccaaccacg tcttcaaagc aagtggattg atgtgatatc tccactgacg    2220
taagggatga cgcacaatcc cactatcctt cgcaagaccc ttcctctata taggaagtt     2280
catttcattt ggagaggact cgagctcatt tctctattac ttcagccata caaaagaac     2340
tcttttctct tcttattaaa ccaaaaccat gagtaaacgg aatccgaaga ttctgaagat    2400
ttttctgtat atgttacttc tcaactctct ctttctcatc atctacttcg ttttcactc     2460
atcgtcgttt tcaagtgtcg tagatgtgat cggtttgctt gcgactgcag cctacgtgac    2520
gttggcgagc gcatacaagg tggtccagtt cattaacgtg tcgagcgtaa cggatgtcgc    2580
tggtctcgaa agtgatgctt tgccgctcac tccaagggtt gacgttatcg tgccgacatt    2640
caatgagaac tccagcacat gctcgagtg cgtcgcttct atatgcgcac aagactaccg    2700
cggaccaata acgattgtcg tggtagacga tgggtcgacc aacaaaacat catttcacgc    2760
agtatgcgac aagtacgcga cgacgaaag gttcatattt gtcgaacttg atcaaaacaa    2820
ggggaagcgc gccgcgcaaa tggaggccat caggagaaca gacggagacc tgatactaaa    2880
cgtagactcg gacacggtta tagataagga tgttgttaca aagcttgcgt cgtccatgag    2940
agccccgaat gtcggtggtg tcatgggca gctcgttgca agaatcgag aaagatcttg      3000
gcttaccaga ttaatcgata tggagtactg gcttgcgtgt aacgaggagc gcattgcgca    3060
gtcgaggttt ggctccgtga tgtgttgttg tgggccgtgc gccatgtata aagatctgc     3120
aattacgcca ctattggcag aatatgagca ccagacattc ctagggcgtc cgagcaactt    3180
tggtgaggat cgccatctca caatcctgat gctgaaggcg ggatttcgga ccgggtacgt    3240
cccaggtgcc gtagcgagga cgttggttcc ggatgggctg gcgccgtacc tgcgccagca    3300
actccgctgg gcccgcagca cttatcgcga caccgccctc gccttacgta taaagaaaaa    3360
tctaagcaaa tatatcacct ttgagatatg cgcacagaat ttgggtacgg ctctcttact    3420
tgtgatgacc atgatttcgc tttcgctgac tacatcaggg tcgcaaacgc ccgttatcat    3480
tctgggtgtc gttgtgggga tgtctataat aagatgttgt tctgtcgccc ttatagcgaa    3540
agattttcgg tttctatact tcatcgttca ctcagcgttg aatgttctaa ttttaacgcc    3600
gttaaaactc tatgccctgt taaccattcg ggatagtcgg tggctatcac gcgagagttc    3660
ctaagctagc aagcttggac acgctgaaat caccagtctc tctctacaaa tctatctctc    3720
tctattttct ccataataat gtgtgagtag ttcccagata agggaattag ggttcctata    3780
```

```
gggtttcgct catgtgttga gcatataaga aacccttagt atgtatttgt atttgtaaaa    3840
tacttctatc aataaaattt ctaattccta aaaccaaaat ccagtactaa aatccagatc    3900
atgcatggta cagcggccaa ttgcctgcag gtcgacggcc gagtactggc aggatatata    3960
ccgttgtaat t                                                         3971
```

<210> SEQ ID NO 11
<211> LENGTH: 431
<212> TYPE: PRT
<213> ORGANISM: Artificial
<220> FEATURE:
<223> OTHER INFORMATION: NODC protein linked to XylT Golgi signal anchor
      sequence
<220> FEATURE:
<221> NAME/KEY: SIGNAL
<222> LOCATION: (1)..(35)
<223> OTHER INFORMATION: 35 N-terminal amino acids of beta-1,2-
      xylosyltransferase from Arabidopsis thaliana
<220> FEATURE:
<221> NAME/KEY: MISC_FEATURE
<222> LOCATION: (36)..(431)
<223> OTHER INFORMATION: NODC from A.caulinodans

<400> SEQUENCE: 11

```
Met Ser Lys Arg Asn Pro Lys Ile Leu Lys Ile Phe Leu Tyr Met Leu
1               5                   10                  15

Leu Leu Asn Ser Leu Phe Leu Ile Ile Tyr Phe Val Phe His Ser Ser
            20                  25                  30

Ser Phe Ser Ser Val Val Asp Val Ile Gly Leu Leu Ala Thr Ala Ala
        35                  40                  45

Tyr Val Thr Leu Ala Ser Ala Tyr Lys Val Val Gln Phe Ile Asn Val
    50                  55                  60

Ser Ser Val Thr Asp Val Ala Gly Leu Glu Ser Asp Ala Leu Pro Leu
65                  70                  75                  80

Thr Pro Arg Val Asp Val Ile Val Pro Thr Phe Asn Glu Asn Ser Ser
                85                  90                  95

Thr Leu Leu Glu Cys Val Ala Ser Ile Cys Ala Gln Asp Tyr Arg Gly
            100                 105                 110

Pro Ile Thr Ile Val Val Asp Asp Gly Ser Thr Asn Lys Thr Ser
        115                 120                 125

Phe His Ala Val Cys Asp Lys Tyr Ala Ser Asp Glu Arg Phe Ile Phe
    130                 135                 140

Val Glu Leu Asp Gln Asn Lys Gly Lys Arg Ala Ala Gln Met Glu Ala
145                 150                 155                 160

Ile Arg Arg Thr Asp Gly Asp Leu Ile Leu Asn Val Asp Ser Asp Thr
                165                 170                 175

Val Ile Asp Lys Asp Val Val Thr Lys Leu Ala Ser Ser Met Arg Ala
            180                 185                 190

Pro Asn Val Gly Gly Val Met Gly Gln Leu Val Ala Lys Asn Arg Glu
        195                 200                 205

Arg Ser Trp Leu Thr Arg Leu Ile Asp Met Glu Tyr Trp Leu Ala Cys
    210                 215                 220

Asn Glu Glu Arg Ile Ala Gln Ser Arg Phe Gly Ser Val Met Cys Cys
225                 230                 235                 240

Cys Gly Pro Cys Ala Met Tyr Arg Arg Ser Ala Ile Thr Pro Leu Leu
                245                 250                 255

Ala Glu Tyr Glu His Gln Thr Phe Leu Gly Arg Pro Ser Asn Phe Gly
            260                 265                 270
```

```
Glu Asp Arg His Leu Thr Ile Leu Met Leu Lys Ala Gly Phe Arg Thr
            275                 280                 285
Gly Tyr Val Pro Gly Ala Val Ala Arg Thr Leu Val Pro Asp Gly Leu
        290                 295                 300
Ala Pro Tyr Leu Arg Gln Gln Leu Arg Trp Ala Arg Ser Thr Tyr Arg
305                 310                 315                 320
Asp Thr Ala Leu Ala Leu Arg Ile Lys Lys Asn Leu Ser Lys Tyr Ile
                325                 330                 335
Thr Phe Glu Ile Cys Ala Gln Asn Gly Thr Ala Leu Leu Leu Val
            340                 345                 350
Met Thr Met Ile Ser Leu Ser Leu Thr Thr Ser Gly Ser Gln Thr Pro
            355                 360                 365
Val Ile Ile Leu Gly Val Val Val Gly Met Ser Ile Ile Arg Cys Cys
        370                 375                 380
Ser Val Ala Leu Ile Ala Lys Asp Phe Arg Phe Leu Tyr Phe Ile Val
385                 390                 395                 400
His Ser Ala Leu Asn Val Leu Ile Leu Thr Pro Leu Lys Leu Tyr Ala
                405                 410                 415
Leu Leu Thr Ile Arg Asp Ser Arg Trp Leu Ser Arg Glu Ser Ser
            420                 425                 430

<210> SEQ ID NO 12
<211> LENGTH: 8491
<212> TYPE: DNA
<213> ORGANISM: Artificial Sequence
<220> FEATURE:
<223> OTHER INFORMATION: TDNA comprising nucleic acids encoding the
      F286 promoter, a Golgi retention peptide and a NODC protein
<220> FEATURE:
<221> NAME/KEY: misc_feature
<222> LOCATION: (1)..(25)
<223> OTHER INFORMATION: right border repeat from the T-DNA of
      Agrobacterium tumefaciens (Zambryski, 1988)
<220> FEATURE:
<221> NAME/KEY: promoter
<222> LOCATION: (75)..(1484)
<223> OTHER INFORMATION: sequence including the promoter region of the
      chitinase F286 gene of Gossypium hirsutum (cotton) (Haigler et
      al., 2004)
<220> FEATURE:
<221> NAME/KEY: sig_peptide
<222> LOCATION: (1485)..(1589)
<220> FEATURE:
<221> NAME/KEY: gene
<222> LOCATION: (1590)..(2778)
<220> FEATURE:
<221> NAME/KEY: 3'UTR
<222> LOCATION: (2781)..(3013)
<223> OTHER INFORMATION: sequence including the 3' untranslated region
      of the 35S transcript of the Cauliflower Mosaic Virus (Sanfacon et
      al., 1991)
<220> FEATURE:
<221> NAME/KEY: promoter
<222> LOCATION: (3036)..(4451)
<223> OTHER INFORMATION: sequence including the promoter region of the
      chitinase F286 gene of Gossypium hirsutum (cotton) (Haigler et
      al., 2004)
<220> FEATURE:
<221> NAME/KEY: gene
<222> LOCATION: (4452)..(6281)
<223> OTHER INFORMATION: coding region of the glutamine:fructose-6-
      phosphate amidotransferase gene of Escherichia coli (Frohberg and
      Essigmann, 2006)
<220> FEATURE:
<221> NAME/KEY: 3'UTR
<222> LOCATION: (6282)..(6555)
<223> OTHER INFORMATION: sequence including the 3' untranslated region
      of the nopaline synthase gene from the T-DNA of pTiT37 (Depicker
      et al., 1982)
```

```
<220> FEATURE:
<221> NAME/KEY: misc_feature
<222> LOCATION: (6598)..(6631)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: promoter
<222> LOCATION: (6632)..(7468)
<223> OTHER INFORMATION: P35S3: sequence including the promoter region
      of the Cauliflower Mosaic Virus 35S transcript (Odell et al.,
      1985)
<220> FEATURE:
<221> NAME/KEY: gene
<222> LOCATION: (7469)..(8020)
<223> OTHER INFORMATION: bar: the coding sequence of the
      phosphinothricin acetyltransferase gene of Streptomyces
      hygroscopicus (Thompson et al., 1987).
<220> FEATURE:
<221> NAME/KEY: 3'UTR
<222> LOCATION: (8021)..(8304)
<223> OTHER INFORMATION: 3'nos: sequence including the 3' untranslated
      region of the nopaline synthase gene from the T-DNA of pTiT37
      (Depicker et al., 1982)
<220> FEATURE:
<221> NAME/KEY: misc_feature
<222> LOCATION: (8305)..(8338)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: misc_feature
<222> LOCATION: (8467)..(8491)
<223> OTHER INFORMATION: left border repeat from the T-DNA of
      Agrobacterium tumefaciens (Zambryski, 1988)

<400> SEQUENCE: 12
aattacaacg gtatatatcc tgccagtact gggcccccctc gagggcgatc gctacgtacc      60
tgcagggcgg ccgccaacct ctcgagctgc catattgggt ttttcactac ccacctcttc     120
attaaatgta tcttcaacct ctcaactcct ttcaccacca gacgaatctt ctttagcaaa     180
atcaaaatga cctatgaaa atttagcacg tccacctcca gattcaaagg ctgtgaatcc     240
ccaacttcgg aaattgttca tctccacatt caagaataat gagttcctca atttgttta     300 actgattagc cgatattaag cgagttagac tccatggaaa taaaatcacc ctaataaata     360
gcaacgcttt tgaacgtctc taggttccaa gcgtgctaag gagcgccagt aacttcaatc     420
caagttgtgc gaaaacgtat gaaatggaac tgagaccagc gttcaacatc gatgaaaatt     480
tgttttaaca atgagaactg caaatcctcc atagtcttct aacatttcaa cattcgaaat     540
ctcgaaaaga aattggcttg atatgattta tttagggtgt taattttatg tattataata     600
atgcacaaat tgatattta tgcatcacat ttaatatttt taaagtatat aatatcaaat     660
cattttatga aaataaaaat accaaataat acataaattg atagttcaag tatttcatta     720
aaaattttca aaatataaat atcatattga aacatttat aaaagaatag ataccaaata     780
tgacatcatc ccctgttgag agtaaccaaa cactgttttc atccagccca tgagaagtat     840
ttggcccaaa agcaaaagtt tcagtacaat gaattatgaa tccaaaaaa accccaagtg     900 gtccaggtcc aagccagtct agggctgagg aaagaaatgg aaaaattgaa aagtaattcc     960
agggtctgat tcaattttat taaatttagt ttgattttgg tttcggttca taaatttaaa    1020 aataattta aaatgttata taaaactgtt ttttaaaat aaattaatca ataatctaaa    1080
acgataaaaa tggcgatttg aattaagctc atatttgaa aaaaaaataa aaattatctc    1140
atccagaact gattaaaacc gaaccgatga atcctagaag ccaagccaag tgtgcagagt    1200
aagaatagaa catcaacatt ttgctttaag ctttttcgttg cttgcactct aagaagcata    1260
```

```
aaacgcaagc aaaacttgac actagtgtga gtgtgagtgc ccatcattca tcaaccctga    1320
aaatcgccct tcccctaatc agttctaacc tcactttcta acactttcac tgcagcactc    1380
aaaaacattc gccgaatctt tactataaac tcccagtgtt ggtttctcca ctccaaaccc    1440
aaaccacgac caccacattt tgcttcgtat ctttgatatc tatcatgagt aaacggaatc    1500
cgaagattct gaagattttt ctgtatatgt tacttctcaa ctctctcttt ctcatcatct    1560
acttcgtttt tcactcatcg tcgttttcaa gtgtcgtaga tgtgatcggt ttgcttgcga    1620
ctgcagccta cgtgacgttg gcgagcgcat acaaggtggt ccagttcatt aacgtgtcga    1680
gcgtaacgga tgtcgctggt ctcgaaagtg atgctttgcc gctcactcca agggttgacg    1740
ttatcgtgcc gacattcaat gagaactcca gcacattgct cgagtgcgtc gcttctatat    1800
gcgcacaaga ctaccgcgga ccaataacga ttgtcgtggt agacgatggg tcgaccaaca    1860
aaacatcatt tcacgcagta tgcgacaagt acgcgagcga cgaaaggttc atatttgtcg    1920
aacttgatca aaacaagggg aagcgcgccg cgcaaatgga ggccatcagg agaacagacg    1980
gagacctgat actaaacgta gactcggaca cggttataga taaggatgtt gttacaaagc    2040
ttgcgtcgtc catgagagcc ccgaatgtcg gtggtgtcat ggggcagctc gttgcaaaga    2100
atcgagaaag atcttggctt accagattaa tcgatatgga gtactggctt gcgtgtaacg    2160
aggagcgcat tgcgcagtcg aggtttggct ccgtgatgtg ttgttgtggg ccgtgcgcca    2220
tgtatagaag atctgcaatt acgccactat tggcagaata tgagcaccag acattcctag    2280
ggcgtccgag caactttggt gaggatcgcc atctcacaat cctgatgctg aaggcgggat    2340
ttcggaccgg gtacgtccca ggtgccgtag cgaggacgtt ggttccggat gggctggcgc    2400
cgtacctgcg ccagcaactc cgctgggccc gcagcactta tcgcgacacc gccctcgcct    2460
tacgtataaa gaaaaatcta agcaaatata tcacctttga gatatgcgca cagaatttgg    2520
gtacggctct cttacttgtg atgaccatga tttcgctttc gctgactaca tcagggtcgc    2580
aaacgcccgt tatcattctg ggtgtcgttg tggggatgtc tataataaga tgttgttctg    2640
tcgcccttat agcgaaagat tttcggtttc tatacttcat cgttcactca gcgttgaatg    2700
ttctaatttt aacgccgtta aaactctatg ccctgttaac cattcgggat agtcggtggc    2760
tatcacgcga gagttcctaa gctagcaagc ttggacacgc tgaaatcacc agtctctctc    2820
tacaaatcta tctctctcta tttttctccat aataatgtgt gagtagttcc cagataaggg    2880
aattagggtt cctatagggt ttcgctcatg tgttgagcat ataagaaacc cttagtatgt    2940
atttgtattt gtaaaatact tctatcaata aaatttctaa ttcctaaaac caaaatccag    3000
tactaaaatc cagacgcgtt taattaagcg gccgccaacc tctcgagctg ccatattggg    3060
tttttcacta cccacctctt cattaaatgt atcttcaacc tctcaactcc tttcaccacc    3120
agacgaatct tctttagcaa aatcaaaatg accttatgaa aatttagcac gtccacctcc    3180
agattcaaag gctgtgaatc cccaacttcg gaaattgttc atctccacat tcaagaataa    3240
tgagttcctc aatttgtttt aactgattag ccgatattaa gcgagttaga ctccatggaa    3300
ataaaatcac cctaataaat agcaacgctt tgaacgtct ctaggttcca agcgtgctaa    3360
ggagcgccag taacttcaat ccaagttgtg cgaaaacgta tgaaatggaa ctgagaccag    3420
cgttcaacat cgatgaaaat ttgttttaac aatgagaact gcaaatcctc catagtcttc    3480
taacatttca acattcgaaa tctcgaaaag aaattggctt gatatgattt atttagggtg    3540 ttaatttat gtattataat aatgcacaaa ttgatatttt atgcatcaca tttaatattt    3600
```

```
ttaaagtata taatatcaaa tcattttatg aaaataaaaa taccaaataa tacataaatt    3660
gatagttcaa gtatttcatt aaaaattttc aaaatataaa tatcatattg aaacatttta    3720
taaaagaata gataccaaat atgacatcat ccctgttga gagtaaccaa acactgtttt    3780
catccagccc atgagaagta tttggcccaa aagcaaaagt ttcagtacaa tgaattatga    3840
atcccaaaaa aaccccaagt ggtccaggtc aagccagtc tagggctgag aaagaaatg     3900 gaaaaattga aaagtaattc cagggtctga ttcaatttta ttaaatttag tttgattttg    3960
gtttcggttc ataaatttaa aaataatttt aaaatgttat ataaaactgt ttttaaaaa    4020 taaattaatc aataatctaa aacgataaaa atggcgattt gaattaagct catattttga    4080
aaaaaaaata aaaattatct catccagaac tgattaaaac cgaaccgatg aatcctagaa    4140
gccaagccaa gtgtgcagag taagaataga acatcaacat tttgctttaa gcttttcgtt    4200
gcttgcactc taagaagcat aaaacgcaag caaaacttga cactagtgtg agtgtgagtg    4260
cccatcattc atcaaccctg aaaatcgccc ttccctaat cagttctaac ctcactttct    4320
aacactttca ctgcagcact caaaaacatt cgccgaatct ttactataaa ctcccagtgt    4380
tggtttctcc actccaaacc caaccacga ccaccacatt ttgcttcgta tctttgatat    4440
ctaggtctcc catgtgcgga attgttggtg ctatcgccca aagagacgtt gctgagattt    4500
tgttagaggg tctgcgaagg ctagagtata gaggatatga ctccgctggt ctggctgtcg    4560
ttgatgctga gggtcatatg acaaggctaa gaaggttagg aaaggttcag atgcttgctc    4620
aggcagctga ggaacatcca ttgcatggag gtactggtat tgcacatacc aggtgggcta    4680
ctcatgggga gccatcagaa gttaatgctc atccacatgt gagtgagcat atcgttgtag    4740
ttcacaatgg gataattgaa aaccacgaac cattgaggga agagttaaag gcaagaggat    4800 atactttgt gagtgagact gacactgagg ttattgcaca tttagtgaac tgggaactca    4860 aacaggggg cacattgcgt gaggctgtgt taagagctat tcctcaactt agaggtgcat    4920
acggtactgt tattatggat tcaagacacc cagatactct ccttgcagct agatcaggta    4980
gtcccttggt cataggactt ggaatggtg aaaatttat cgctagcgac caattggcct    5040
tattgccagt tacaagacga tttatttcc ttgaagaggg cgatattgct gagattacta    5100
gaaggtctgt gaacatcttt gataagactg gcgctgaggt taaacgtcag gatatcgagt    5160
ctaaccttca atacgatgct ggtgataaag gaatttacag gcattatatg caaaaggaaa    5220
tttatgaaca accaaatgct atcaaaaaca cacttactgg ccgtatttct catggacagg    5280
tcgatttaag cgagcttggt cctaatgcag acgaactgct atcaaaagtt gagcacatac    5340
agatactggc atgcggaact agttataatt caggaatggt gtctagatac tggttcgaaa    5400
gcttggcagg tataccttgt gatgtagaga tcgcttctga gtttaggtat agaaagtctg    5460
ctgtgcgtag aaattcatta atgattacat tatctcaatc cggagaaaca gcagatacac    5520
tggctggatt gaggctttct aaggaactcg gatatctggg ttcacttgct atttgtaatg    5580
taccaggttc ctcattggtt cgtgaatcag atctagcact tatgacaaat gcaggaactg    5640
aaataggtgt ggcaagtacc aaggctttca aacccaact gaccgtactt ttaatgttgg    5700
tagcaaaact cagtcgatta aaggggctag atgcatctat cgaacatgat attgttcacg    5760
ggcttcaagc tctcccttca agaattgaac aaatgctttc acaagataag agaatagagg    5820
cattggctga agatttttcc gacaaacatc acgcattgtt tcttggacgt ggcgatcaat    5880
atccaattgc attggaagga gctttgaagt tgaaagaaat aagttacatt cacgcagaag    5940
catatgcagc tggagaactc aagcatggtc ctttggcact catcgacgct gacatgcccg    6000
```

```
tgatcgtagt ggctcctaat aacgaactgc tcgaaaagct aaatcaaat atcgaagagg      6060 ttcgagctag aggaggtcag ctttacgttt tcgctgaaca agatgctgga ttcgtgtcaa     6120
gcgataatat gcatataatt gaaatgcctc acgttgaaga agtgattgca cctatatttt    6180
atacagtccc attgcaactt ctagcttacc atgttgcact tattaaagga actgatgttg    6240
atcagcctag aaacctagca aaatctgtaa cagtcgaata acgcgtggc gcgccgaagc     6300 agatcgttca acatttggc aataaagttt cttaagattg aatcctgttg ccggtcttgc     6360
gatgattatc atataatttc tgttgaatta cgttaagcat gtaataatta acatgtaatg    6420
catgacgtta tttatgagat gggttttat gattagagtc ccgcaattat acatttaata    6480
cgcgatagaa acaaaatat agcgcgcaaa ctaggataaa ttatcgcgcg cggtgtcatc    6540
tatgttacta gatcggaatt cgatatcatt accctgttat ccctaaagct tattaatata   6600
acttcgtata gcatacatta tacgaagtta tgtttcctac gcagcaggtc tcatcaagac   6660
gatctacccg agtaacaatc tccaggagat caaatacctt cccaagaagg ttaaagatgc   6720
agtcaaaaga ttcaggacta attgcatcaa gaacacagag aaagacatat ttctcaagat   6780
cagaagtact attccagtat ggacgattca aggcttgctt cataaaccaa ggcaagtaat   6840
agagattgga gtctctaaaa aggtagttcc tactgaatct aaggccatgc atggagtcta   6900
agattcaaat cgaggatcta acagaactcg ccgtgaagac tggcgaacag ttcatacaga   6960
gtcttttacg actcaatgac aagaagaaaa tcttcgtcaa catggtggag cacgacactc   7020
tggtctactc caaaaatgtc aaagatacag tctcagaaga ccaaagggct attgagactt    7080
ttcaacaaag gataatttcg ggaaacctcc tcggattcca ttgcccagct atctgtcact    7140
tcatcgaaag gacagtagaa aaggaaggtg ctcctacaa atgccatcat tgcgataaag    7200
gaaaggctat cattcaagat gcctctgccg acagtggtcc caaagatgga cccccaccca    7260
cgaggagcat cgtggaaaaa gaagacgttc caaccacgtc ttcaaagcaa gtggattgat    7320
gtgacatctc cactgacgta agggatgacg cacaatccca ctatccttcg caagacccttt   7380 cctctatata aggaagttca tttcatttgg agaggacacg ctgaaatcac cagtctctct    7440
ctataaatct atctctctct ctataacaat ggacccagaa cgacgcccgg ccgacatccg    7500
ccgtgccacc gaggcggaca tgccggcggt ctgcaccatc gtcaaccact acatcgagac    7560
aagcacggtc aacttccgta ccgagccgca ggaaccgcag gagtggacgg acgacctcgt    7620
ccgtctgcgg gagcgctatc cctggctcgt cgccgaggtg acggcgagg tcgccggcat    7680 cgcctacgcg ggcccctgga aggcacgcaa cgcctacgac tggacggccg agtcgaccgt    7740
gtacgtctcc ccccgccacc agcggacggg actgggctcc acgtctctaca cccacctgct   7800 gaagtccctg gaggcacagg gcttcaagag cgtggtcgct gtcatcgggc tgcccaacga    7860
cccgagcgtg cgcatgcacg aggcgctcgg atatgcccc cgcggcatgc tgcgggcggc   7920
cggcttcaag cacgggaact ggcatgacgt gggtttctgg cagctggact tcagcctgcc    7980
ggtaccgccc cgtccggtcc tgcccgtcac cgagatctga gatcacccgt tctaggatcc    8040
gaagcagatc gttcaaacat ttggcaataa agtttcttaa gattgaatcc tgttgccggt    8100
cttgcgatga ttatcatata atttctgttg aattacgtta agcatgtaat aattaacatg    8160
taatgcatga cgttatttat gagatgggtt tttatgatta gagtcccgca attatacatt    8220
taatacgcga tagaaaacaa aatatagcgc gcaaactagg ataaattatc gcgcgcggtg    8280
tcatctatgt tactagatcg aaacataact tcgtatagca tacattatac gaagttatca    8340
```

```
aaacgtcgtg agacagtttg gttaactata acggtcctaa ggtagcgatc gaggcattac    8400
ggcattacgg cactcgcgag ggtccgaatc tatgtcgggt gcggagaaag aggtaatgaa    8460
atggcaattt acaattgaat atatcctgcc g                                   8491
```

```
<210> SEQ ID NO 13
<211> LENGTH: 9567
<212> TYPE: DNA
<213> ORGANISM: Artificial Sequence
<220> FEATURE:
<223> OTHER INFORMATION: TDNA comprising nucleic acid sequences encoding
      the gluc1A promoter, a Golgi retention peptide and a NODC protein
<220> FEATURE:
<221> NAME/KEY: misc_feature
<222> LOCATION: (1)..(25)
<223> OTHER INFORMATION: right border repeat from the T-DNA of
      Agrobacterium tumefaciens (Zambryski, 1988)
<220> FEATURE:
<221> NAME/KEY: promoter
<222> LOCATION: (26)..(2025)
<223> OTHER INFORMATION: sequence including the promoter region of the
      beta-1,3-endoglucanase gene gluc1 of the A subgenome of Gossypium
      hirsutum (cotton)(Engelen and Arioli, 2008)
<220> FEATURE:
<221> NAME/KEY: sig_peptide
<222> LOCATION: (2026)..(2130)
<220> FEATURE:
<221> NAME/KEY: gene
<222> LOCATION: (2131)..(3321)
<220> FEATURE:
<221> NAME/KEY: 3'UTR
<222> LOCATION: (3322)..(3554)
<223> OTHER INFORMATION: sequence including the 3' untranslated region
      of the 35S transcript of the Cauliflower Mosaic Virus (Sanfacon et
      al., 1991)
<220> FEATURE:
<221> NAME/KEY: promoter
<222> LOCATION: (3555)..(5527)
<223> OTHER INFORMATION: Pgluc1(A1.9): sequence including the promoter
      region of the beta-1,3-endoglucanase gene gluc1 of the A subgenome
      of Gossypium hirsutum (cotton)(Engelen and Arioli, 2008)
<220> FEATURE:
<221> NAME/KEY: gene
<222> LOCATION: (5528)..(7357)
<223> OTHER INFORMATION: gfaEc-1Pb: coding region of the glutamine:
      fructose-6-phosphate amidotransferase gene of Escherichia coli
      (Frohberg and Essigmann, 2006)
<220> FEATURE:
<221> NAME/KEY: 3'UTR
<222> LOCATION: (7358)..(7631)
<223> OTHER INFORMATION: 3'nos: sequence including the 3' untranslated
      region of the nopaline synthase gene from the T-DNA of pTiT37
      (Depicker et al., 1982)
<220> FEATURE:
<221> NAME/KEY: misc_feature
<222> LOCATION: (7674)..(7707)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: promoter
<222> LOCATION: (7708)..(8544)
<223> OTHER INFORMATION: P35S3: sequence including the promoter region
      of the Cauliflower Mosaic Virus 35S transcript (Odell et al.,
      1985)
<220> FEATURE:
<221> NAME/KEY: gene
<222> LOCATION: (8545)..(9096)
<223> OTHER INFORMATION: bar: coding sequence of the phosphinothricin
      acetyltransferase gene of Streptomyces hygroscopicus (Thompson et
      al., 1987).
<220> FEATURE:
<221> NAME/KEY: 3'UTR
<222> LOCATION: (9097)..(9380)
<223> OTHER INFORMATION: 3'nos: sequence including the 3' untranslated
      region of the nopaline synthase gene from the T-DNA of pTiT37
      (Depicker et al., 1982)
```

```
<220> FEATURE:
<221> NAME/KEY: misc_feature
<222> LOCATION: (9381)..(9414)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: misc_feature
<222> LOCATION: (9543)..(9567)
<223> OTHER INFORMATION: left border repeat from the T-DNA of
      Agrobacterium tumefaciens (Zambryski, 1988)

<400> SEQUENCE: 13
```

| | | | | | |
|---|---|---|---|---|---|
| aattacaacg | gtatatatcc | tgccagtact | gggcccctc | gagggcgatc | gctacgtacc | 60 |
| tgcagggcgg | ccgcgattat | ataaataggg | ggcgaatcta | gggagctggc | atgacccta | 120 |
| aaatagaatt | ttctattttg | acctatcaaa | attttaaaa | ttttaaatta | gtaaaggtaa | 180 |
| atttgtactt | taacctctta | aaatgataaa | attttacttt | aatcctttaa | aatttacatt | 240 |
| tttactatca | taaaaattac | aatttgattt | taccctaaa | attttttct | agcttagccc | 300 |
| tgtatataaa | tatattattt | ataatttta | tatttaaaat | ataagtttt | taattataca | 360 |
| aataattaaa | atctgatatt | taaaactaaa | gtaatttctt | ttttcttttt | actttttttt | 420 |
| aattgcaaca | taatggttta | aatatctata | taacgtatga | agtaatttga | tataaatttt | 480 |
| atttaatttt | attattatat | aaattcattt | agtaaaaact | tttaatagaa | tcaaaatttt | 540 |
| tatttgtaaa | ttcgataact | tttcttatca | agtatatttg | tgagaaccaa | atatttagta | 600 |
| aaattaatat | tcttatttat | aaatatgata | aatcttataa | aaaaatattt | aaaatgaaaa | 660 |
| aaattgtaca | aatattataa | aaaaatattt | aaaatgaaaa | acattgtaca | aaggctatat | 720 |
| aagaagttca | aaagtttctt | cgaccatgta | ctcttataga | gattatagat | agattataaa | 780 |
| actatatgta | gtttctctta | acttttaaat | aagaggataa | atgtatttta | atgtactcaa | 840 |
| acttatatat | ttttatattg | acaataatat | caatatcaac | ctaattaaga | ttcattctaa | 900 |
| cattaatgtt | gaagatttt | aataaaagaa | aaggttaata | aattaattag | aacacaaaca | 960 |
| aacacaaatt | taagtggtat | gtaaggtcct | tgacccaaag | gaaaaatttg | ttacgtcgat | 1020 |
| taaattataa | attaatttaa | agtaaaatta | cattttaacc | taaaaaaaga | gaaaagtata | 1080 |
| tctaatttct | tcgaaaatgg | aaagaaaatt | ataaatttat | ggcatttcta | aaaaaattct | 1140 |
| gaattcgcta | ctaaaagatg | aaattataaa | atccgaagca | ttaccagaag | atggatcacc | 1200 |
| aaatcacaaa | caatcaatga | aaagtaatga | taattaattg | aaagtgagca | tttaattttg | 1260 |
| atagccatat | acttcctgct | gaatttatag | gttctcatta | atgcaattaa | attatattcg | 1320 |
| acaccttttg | aatgaaataa | aatgacacaa | gaggaaagac | ggttcatcta | tttttctttt | 1380 |
| caatcgccca | tcaaaatacc | aaaaatgtaa | ctacatgcaa | aaaatcaaat | atgaaaata | 1440 |
| ttcatattt | gatattttaa | tatattgtgt | gttcaaaacg | taaatgtatt | gaaaaattat | 1500 |
| gatggtgttg | ttgctgtatg | tccataaaat | tcaatgtact | cacatttatc | aaatgtatac | 1560 |
| tttgagagaa | gttattttga | taatactcaa | gtttttttta | tagatgggaa | aattttttaa | 1620 |
| attatttttt | gattttgatg | aaatgtatat | ataaattta | attcgataca | tataaatata | 1680 |
| tatgtaaatt | ttaaatttaa | atttaataat | atacaattaa | gaaaataatt | tacataaata | 1740 |
| tatatcctaa | taaaaataaa | attagaaaga | ggaaatgtca | aaacctcttc | attatataca | 1800 |
| aatatgatgg | gacacgatac | cctcatgcat | tgatatctca | tgttgtccaa | aaactcggaa | 1860 |
| tcctttttga | aaaaaaactt | ccagagagag | tatataaatc | cagcagtagg | cacaagaaac | 1920 |
| gagcaccagt | tattgacttt | cctttgtaaa | aaaaaaaag | tgctgagatc | aagaaatata | 1980 |

```
gtgaaatatg ggtccaagat tttctgggtt tttaatctaa gcaccatgag taaacggaat    2040
ccgaagattc tgaagatttt tctgtatatg ttacttctca actctctctt tctcatcatc    2100
tacttcgttt ttcactcatc gtcgttttca agtgtcgtag atgtgatcgg tttgcttgcg    2160
actgcagcct acgtgacgtt ggcgagcgca tacaaggtgg tccagttcat taacgtgtcg    2220
agcgtaacgg atgtcgctgg tctcgaaagt gatgctttgc cgctcactcc aagggttgac    2280
gttatcgtgc cgacattcaa tgagaactcc agcacattgc tcgagtgcgt cgcttctata    2340
tgcgcacaag actaccgcgg accaataacg attgtcgtgg tagacgatgg gtcgaccaac    2400
aaaacatcat ttcacgcagt atgcgacaag tacgcgagcg acgaaaggtt catatttgtc    2460
gaacttgatc aaaacaaggg gaagcgcgcc gcgcaaatgg aggccatcag gagaacagac    2520
ggagacctga tactaaacgt agactcggac acgttatatg ataaggatgt tgttacaaag    2580
cttgcgtcgt ccatgagagc cccgaatgtc ggtggtgtca tggggcagct cgttgcaaag    2640
aatcgagaaa gatcttggct taccagatta atcgatatgg agtactggct tgcgtgtaac    2700
gaggagcgca ttgcgcagtc gaggtttggc tccgtgatgt gttgttgtgg gccgtgcgcc    2760
atgtatagaa gatctgcaat tacgccacta ttggcagaat atgagcacca gacattccta    2820
gggcgtccga gcaactttgg tgaggatcgc catctcacaa tcctgatgct gaaggcggga    2880
tttcggaccg ggtacgtccc aggtgccgta gcgaggacgt tggttccgga tgggctggcg    2940
ccgtacctgc gccagcaact ccgctgggcc cgcagcactt atcgcgacac cgccctcgcc    3000
ttacgtataa agaaaaatct aagcaaatat atcacctttg agatatgcgc acagaatttg    3060
ggtacggctc tcttacttgt gatgaccatg atttcgcttt cgctgactac atcagggtcg    3120
caaacgcccg ttatcattct gggtgtcgtt gtggggatgt ctataataag atgttgttct    3180
gtcgcccttt tagcgaaaga ttttcggttt ctatacttca tcgttcactc agcgttgaat    3240
gttctaattt taacgccgtt aaaactctat gccctgttaa ccattcggga tagtcggtgg    3300
ctatcacgcg agagttccta agctagcaag cttggacacg ctgaaatcac cagtctctct    3360
ctacaaatct atctctctct attttctcca taataatgtg tgagtagttc ccagataagg    3420
gaattagggt tcctataggg tttcgctcat gtgttgagca tataagaaac ccttagtatg    3480
tatttgtatt tgtaaaatac ttctatcaat aaaatttcta attcctaaaa ccaaaatcca    3540
gtactaaaat ccagacgcgt ttaattaagc ggccgcgatt atataaatag ggggcgaatc    3600
tagggagctg gcatgacccc taaaatagaa ttttctattt tgacctatca aaattttaa    3660 aattttaaat tagtaaaggt aaatttgtac tttaacctct taaaatgata aaattttact    3720
ttaatccttt aaaatttaca ttttactat cataaaaatt acaatttgat tttaccccta    3780 aaatttttt ctagcttagc cctgtatata aatatattat ttataattt tatatttaaa    3840 atataaagtt tttaattata caaataatta aaatctgata tttaaaacta aagtaatttc    3900
ttttttcttt ttacttttt ttaattgcaa cataatggtt taaatatcta taacgtat    3960 gaagtaattt gatataaatt ttattttaat ttattattat ataaattcat ttagtaaaaa    4020
cttttaatag aatcaaaatt tttatttgta aattcgataa cttttcttat caagtatatt    4080
tgtgagaacc aaatatttag taaaattaat attcttattt ataaatatga taaatcttat    4140
aaaaaaatat ttaaatgaa aaaaattgta caaatattat aaaaaaatat ttaaatgaa    4200 aaacattgta caaaggctat ataagaagtt caaaagtttc ttcgaccatg tactcttata    4260
gagattatag atagattata aaactatatg tagtttctct taacttttaa ataagaggat    4320
```

```
aaatgtattt taatgtactc aaacttatat attttatat tgacaataat atcaatatca    4380
acctaattaa gattcattct aacattaatg ttgaagattt ttaataaaag aaaaggttaa    4440
taaattaatt agaacacaaa caaacacaaa tttaagtggt atgtaaggtc cttgacccaa    4500
aggaaaaatt tgttacgtcg attaaattat aaattaattt aaagtaaaat tacattttaa    4560
cctaaaaaaa gagaaaagta tatctaattt cttcgaaaat ggaagaaaaa ttataaattt    4620
atggcatttc taaaaaaatt ctgaattcgc tactaaaaga tgaaattata aaatccgaag    4680
cattaccaga agatggatca ccaaatcaca aacaatcaat gaaaagtaat gataattaat    4740
tgaaagtgag catttaattt tgatagccat atacttcctg ctgaatttat aggttctcat    4800
taatgcaatt aaattatatt cgacaccttt tgaatgaaat aaaatgacac aagaggaaag    4860
acggttcatc tatttttct ttcaatcgcc catcaaaata ccaaaaatgt aactacatgc    4920
aaaaaatcaa atatgaaaaa tattcatatt ttgatatttt aatatattgt gtgttcaaaa    4980
cgtaaatgta ttgaaaaatt atgatggtgt tgttgctgta tgtccataaa attcaatgta    5040
ctcacattta tcaaatgtat actttgagag aagttatttt gataatactc aagtttttt    5100 tatagatggg aaaattttt aaattatttt ttgattttga tgaaatgtat atataaattt    5160
taattcgata catataaata tatatgtaaa ttttaaattt aaatttaata atatacaatt    5220
aagaaaataa tttacataaa tatatatcct aataaaaata aaattagaaa gaggaaatgt    5280
caaaacctct tcattatata caaatatgat gggacacgat accctcatgc attgatatct    5340
catgttgtcc aaaaactcgg aatccttttt gaaaaaaaac ttccagagag agtatataaa    5400
tccagcagta ggcacaagaa acgagcacca gttattgact ttcctttgta aaaaaaaaaa    5460
agtgctgaga tcaagaaata tagtgaaata tgggtccaag atttctgggg ttttaatct    5520 aagcaccatg tgcggaattg ttggtgctat cgcccaaaga gacgttgctg agattttgtt    5580
agagggtctg cgaaggctag agtatagagg atatgactcc gctggtctgg ctgtcgttga    5640
tgctgagggt catatgacaa ggctaagaag gttaggaaag gttcagatgc ttgctcaggc    5700
agctgaggaa catccattgc atggaggtac tggtattgca cataccaggt gggctactca    5760
tggggagcca tcagaagtta atgctcatcc acatgtgagt gagcatatcg ttgtagttca    5820
caatgggata attgaaaacc acgaaccatt gagggaagag ttaaaggcaa gaggatatac    5880
ttttgtgagt gagactgaca ctgaggttat tgcacattta tgaactggg aactcaaaca    5940 gggggggcaca ttgcgtgagg ctgtgttaag agctattcct caacttagag gtgcatacgg    6000
tactgttatt atggattcaa gacacccaga tactctcctt gcagctagat caggtagtcc    6060
cttggtcata ggacttggaa tgggtgaaaa ttttatcgct agcgaccaat tggccttatt    6120
gccagttaca agacgattta ttttccttga agagggcgat attgctgaga ttactagaag    6180
gtctgtgaac atctttgata agactggcgc tgaggttaaa cgtcaggata tcgagtctaa    6240
ccttcaatac gatgctggtg ataaaggaat ttacaggcat tatatgcaaa aggaaattta    6300
tgaacaacca aatgctatca aaaacacact tactggccgt atttctcatg acaggtcga    6360 tttaagcgag cttggtccta atgcagacga actgctatca aaagttgagc acatacagat    6420
actggcatgc ggaactagtt ataattcagg aatggtgtct agatactggt tcgaaagctt    6480
ggcaggtata ccttgtgatg tagagatcgc ttctgagttt aggtatagaa agtctgctgt    6540
gcgtagaaat tcattaatga ttacattatc tcaatccgga gaaacagcag atacactggc    6600
tggattgagg ctttctaagg aactcggata tctgggttca cttgctattt gtaatgtacc    6660
aggttcctca ttggttcgtg aatcagatct agcacttatg acaaatgcag gaactgaaat    6720
```

```
aggtgtggca agtaccaagg ctttcacaac ccaactgacc gtacttttaa tgttggtagc    6780
aaaactcagt cgattaaagg ggctagatgc atctatcgaa catgatattg ttcacgggct    6840
tcaagctctc ccttcaagaa ttgaacaaat gctttcacaa gataagagaa tagaggcatt    6900
ggctgaagat ttttccgaca acatcacgc attgtttctt ggacgtggcg atcaatatcc    6960
aattgcattg gaaggagctt tgaagttgaa agaaataagt tacattcacg cagaagcata    7020
tgcagctgga gaactcaagc atggtccttt ggcactcatc gacgctgaca tgcccgtgat    7080
cgtagtggct cctaataacg aactgctcga aaagcttaaa tcaaatatcg aagaggttcg    7140
agctagagga ggtcagcttt acgttttcgc tgaacaagat gctggattcg tgtcaagcga    7200
taatatgcat ataattgaaa tgcctcacgt tgaagaagtg attgcaccta tattttatac    7260
agtcccattg caacttctag cttaccatgt tgcacttatt aaaggaactg atgttgatca    7320
gcctagaaac ctagcaaaat ctgtaacagt cgaataaacg cgtggcgcgc cgaagcagat    7380
cgttcaaaca tttggcaata aagtttctta agattgaatc ctgttgccgg tcttgcgatg    7440
attatcatat aatttctgtt gaattacgtt aagcatgtaa taattaacat gtaatgcatg    7500
acgttattta tgagatgggt ttttatgatt agagtcccgc aattatacat ttaatacgcg    7560
atagaaaaca aaatatagcg cgcaaactag gataaattat cgcgcgcggt gtcatctatg    7620
ttactagatc ggaattcgat atcattaccc tgttatccct aaagcttatt aatataactt    7680
cgtatagcat acattatacg aagttatgtt tcctacgcag caggtctcat caagacgatc    7740
tacccgagta acaatctcca ggagatcaaa taccttccca agaaggttaa agatgcagtc    7800
aaaagattca ggactaattg catcaagaac acagagaaag acatatttct caagatcaga    7860
agtactattc cagtatggac gattcaaggc ttgcttcata aaccaaggca agtaatagag    7920
attggagtct ctaaaaaggt agttcctact gaatctaagg ccatgcatgg agtctaagat    7980
tcaaatcgag gatctaacag aactcgccgt gaagactggc gaacagttca tacagagtct    8040
tttacgactc aatgacaaga agaaaatctt cgtcaacatg gtggagcacg acactctggt    8100
ctactccaaa aatgtcaaag atacagtctc agaagaccaa agggctattg agacttttca    8160 acaaggata atttcgggaa acctcctcgg attccattgc ccagctatct gtcacttcat    8220
cgaaaggaca gtagaaaagg aaggtggctc ctacaaatgc catcattgcg ataaaggaaa    8280
ggctatcatt caagatgcct ctgccgacag tggtcccaaa gatggacccc cacccacgag    8340
gagcatcgtg gaaaaagaag acgttccaac cacgtcttca aagcaagtgg attgatgtga    8400
catctccact gacgtaaggg atgacgcaca atcccactat ccttcgcaag acccttcctc    8460
tatataagga agttcatttc atttggagag gacacgctga atcaccagt ctctctctat    8520 aaatctatct ctctctctat aacaatggac ccagaacgac gcccggccga catccgccgt    8580
gccaccgagg cggacatgcc ggcggtctgc accatcgtca accactacat cgagacaagc    8640
acggtcaact tccgtaccga gccgcaggaa ccgcaggagt ggacgacga cctcgtccgt    8700 ctgcgggagc gctatccctg gctcgtcgcc gaggtggacg gcgaggtcgc cggcatcgcc    8760
tacgcgggcc cctggaaggc acgcaacgcc tacgactgga cggccgagtc gaccgtgtac    8820
gtctcccccc gccaccagcg gacgggactg gctccacgc tctacaccca cctgctgaag    8880
tccctggagg cacagggctt caagagcgtg gtcgctgtca tcgggctgcc caacgacccg    8940
agcgtgcgca tgcacgaggc gctcggatat gcccccgcg gcatgctgcg gcggccggc    9000 ttcaagcacg ggaactggca tgacgtgggt ttctggcagc tggacttcag cctgccggta    9060
```

-continued

```
ccgccccgtc cggtcctgcc cgtcaccgag atctgagatc acccgttcta ggatccgaag      9120
cagatcgttc aaacatttgg caataaagtt tcttaagatt gaatcctgtt gccggtcttg      9180
cgatgattat catataattt ctgttgaatt acgttaagca tgtaataatt aacatgtaat      9240
gcatgacgtt atttatgaga tgggttttta tgattagagt cccgcaatta tacatttaat      9300
acgcgataga aaacaaaata tagcgcgcaa actaggataa attatcgcgc gcggtgtcat      9360
ctatgttact agatcgaaac ataacttcgt atagcataca ttatacgaag ttatcaaaac      9420
gtcgtgagac agtttggtta actataacgg tcctaaggta gcgatcgagg cattacggca      9480
ttacggcact cgcgagggtc cgaatctatg tcgggtgcgg agaaagaggt aatgaaatgg      9540
caatttacaa ttgaatatat cctgccg                                         9567
```

<210> SEQ ID NO 14
<211> LENGTH: 9621
<212> TYPE: DNA
<213> ORGANISM: Artificial Sequence
<220> FEATURE:
<223> OTHER INFORMATION: TDNA comprising nucleic acid sequences encoding
      the gluc1D promoter, a Golgi retention peptide and a NODC protein
<220> FEATURE:
<221> NAME/KEY: misc_feature
<222> LOCATION: (1)..(25)
<223> OTHER INFORMATION: right border repeat from the T-DNA of
      Agrobacterium tumefaciens (Zambryski, 1988)
<220> FEATURE:
<221> NAME/KEY: promoter
<222> LOCATION: (26)..(2052)
<223> OTHER INFORMATION: sequence including the promoter region of the
      beta-1,3-endoglucanase gene gluc1 of the D subgenome of Gossypium
      hirsutum (cotton)(Engelen and Arioli, 2008)
<220> FEATURE:
<221> NAME/KEY: sig_peptide
<222> LOCATION: (2053)..(2157)
<220> FEATURE:
<221> NAME/KEY: gene
<222> LOCATION: (2158)..(3348)
<220> FEATURE:
<221> NAME/KEY: 3'UTR
<222> LOCATION: (3349)..(3581)
<223> OTHER INFORMATION: sequence including the 3' untranslated region
      of the 35S transcript of the Cauliflower Mosaic Virus (Sanfacon et
      al., 1991)
<220> FEATURE:
<221> NAME/KEY: promoter
<222> LOCATION: (3582)..(5581)
<223> OTHER INFORMATION: Pgluc1(D2.0): sequence including the promoter
      region of the beta-1,3-endoglucanase gene gluc1 of the D subgenome
      of Gossypium hirsutum (cotton)(Engelen and Arioli, 2008)
<220> FEATURE:
<221> NAME/KEY: gene
<222> LOCATION: (5582)..(7411)
<223> OTHER INFORMATION: gfaEc-1Pb: coding region of the glutamine:
      fructose-6-phosphate amidotransferase gene of Escherichia coli
      (Frohberg and Essigmann, 2006)
<220> FEATURE:
<221> NAME/KEY: 3'UTR
<222> LOCATION: (7412)..(7685)
<223> OTHER INFORMATION: 3'nos: sequence including the 3' untranslated
      region of the nopaline synthase gene from the T-DNA of pTiT37
      (Depicker et al., 1982)
<220> FEATURE:
<221> NAME/KEY: misc_feature
<222> LOCATION: (7728)..(7761)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: promoter
<222> LOCATION: (7762)..(8598)
<223> OTHER INFORMATION: P35S3: sequence including the promoter region
      of the Cauliflower Mosaic Virus 35S transcript (Odell et al.,
      1985)

```
<220> FEATURE:
<221> NAME/KEY: gene
<222> LOCATION: (8599)..(9150)
<223> OTHER INFORMATION: bar: coding sequence of the phosphinothricin
      acetyltransferase gene of Streptomyces hygroscopicus (Thompson et
      al., 1987).
<220> FEATURE:
<221> NAME/KEY: 3'UTR
<222> LOCATION: (9151)..(9434)
<223> OTHER INFORMATION: 3'nos: sequence including the 3' untranslated
      region of the nopaline synthase gene from the T-DNA of pTiT37
      (Depicker et al., 1982)
<220> FEATURE:
<221> NAME/KEY: misc_feature
<222> LOCATION: (9435)..(9468)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: misc_feature
<222> LOCATION: (9597)..(9621)
<223> OTHER INFORMATION: left border repeat from the T-DNA of
      Agrobacterium tumefaciens (Zambryski, 1988)

<400> SEQUENCE: 14
aattacaacg gtatatatcc tgccagtact gggcccccctc gagggcgatc gctacgtacc      60
tgcagggcgg ccgcttcgaa cataatgcta ataaaaaatt tcctaatcat tattaaatca     120
tttgtataaa ctataaagaa attgatatat tgtaaattaa acttttaact attcaattt      180 ttcttaatag tcaataaatt aatcataata attcataatt aatatataat taacataacc     240
ataacataga atttttatt ttggcccatt aaaattttta aaattttaaa ttagtaaagg      300
aaaaattaca ctttgacccc ttaaaaatga taaaattta ttttaatcct ttaaaattga      360 cattttact attgtaaaaa ttacaattta attttgcccc cctaaaaat ttttctagct      420 tcgcccttgt gtataaatat attaattaca attttatat ttgaattata taaataatta     480
aattttgata tttaaaacta aagtaatctc tttttttttt acttttttt aattgaaaca     540 taatggttta aatatctata ttacgtatga agtaatttaa tataaatttt attttaattt     600
attattatat aaattcattt agtaaaaact tttaatagaa tcaaaattt tatttgtaaa     660 ttcgataact tttcttatca agtaaatttg ttgaattaaa tatttagtaa aattaatatt     720
tttatttata aatatgataa atcttataaa aaataaaaaa atatttaaaa tgaaaaacat     780
tgtacaaagg ctatataaga agttcaaaag tttcttcgac cctgtactct aatagagatt     840
atagatagat tatagaacta ttcatagttt ctcttaacct ttaaataaga attttagtgt     900
actcaaactt acatattttt atattgataa taatgtcaat accagccgag ttaagattca     960
ctcgacatta atgttgaaaa ttttaataa agaaaatgt tgataagtta attagaacac     1020
aagcaagcac aaatttaagt ggtaagtaag gtccttgacc ctaatggaaa aattgttatg     1080
ttgattaaat tataaattaa tttaaggtaa aattatattt tgacctaaaa aaatgaaaaa     1140
aatatatcta gtttcttcga aaatgaaaag aaaataataa attgatacat tataaaattt     1200
atggcatttc taaaaaaatt ctgaatttga tgaaattata ataaaaaaaa agtttaaaaa     1260
catatagatt tcaagaatag tgggaaaatt atatttgaac aacactgaag aaatccaaag     1320
cattagcaga aaatggatca ccaaatcaca aacaatcagt gaaaagtaat gataattaat     1380
tgaaagtgag catttaaatt tgatagccat atacttcctg ctgaatttat aggttctcat     1440
taatgcaatt aaattatatt tgtcactttt tgaatgaaat aaatgacaca gttcatctat     1500 ttttttttctt tcaatcgccc atcaaaatac cgaaaatgta actacattaa aaaagatcga     1560
aaaatattca tattttgata ttttaataga ttgtgtgttc aaggcgtaat gtactaaaaa     1620
```

```
attatgatgg tgttgtcgct gtatgtccat aaaattcaat gtattcgcat gtatcaaatg    1680
taaattttga cacaagttat tctaataata atcaagttat ttttatacat gagatacatc    1740
tcaaaattat ttttatatat ccgaaaaatc ataacgtacg atcaaactag aaagaggaag    1800
tgtcaaaacc tattcattat atgcaaatat gatgggacac gataccctca tgcattgata    1860
tctcatattg tccaaaaact cagaatcctt tttgaaaaaa aaaaattcca gagagagtgt    1920
ataaatccag cagtgtgcac aagaaacgag caccagttat tgacattcct ttgtaaaaaa    1980
aaaaagaagc tgagatcaag aaatatagtg aaatatgggt ccaacatttt ctgggttttt    2040
aatctcagca ccatgagtaa acggaatccg aagattctga agattttcct gtatatgtta    2100
cttctcaact ctctctttct catcatctac ttcgttttc actcatcgtc gttttcaagt     2160
gtcgtagatg tgatcggttt gcttgcgact gcagcctacg tgacgttggc gagcgcatac    2220
aaggtggtcc agttcattaa cgtgtcgagc gtaacggatg tcgctggtct cgaaagtgat    2280
gctttgccgc tcactccaag ggttgacgtt atcgtgccga cattcaatga gaactccagc    2340
acattgctcg agtgcgtcgc ttctatatgc gcacaagact accgcggacc aataacgatt    2400
gtcgtggtag acgatgggtc gaccaacaaa acatcatttc acgcagtatg cgacaagtac    2460
gcgagcgacg aaaggttcat atttgtcgaa cttgatcaaa acaaggggaa gcgcgccgcg    2520
caaatggagg ccatcaggag aacagacgga gacctgatac taaacgtaga ctcggacacg    2580
gttatagata aggatgttgt tacaaagctt gcgtcgtcca tgagagcccc gaatgtcggt    2640
ggtgtcatgg ggcagctcgt tgcaaagaat cgagaaagat cttggcttac cagattaatc    2700
gatatggagt actggcttgc gtgtaacgag gagcgcattg cgcagtcgag gtttggctcc    2760
gtgatgtgtt gttgtgggcc gtgcgccatg tatagaagat ctgcaattac gccactattg    2820
gcagaatatg agcaccagac attcctaggg cgtccgagca actttggtga ggatcgccat    2880
ctcacaatcc tgatgctgaa ggcgggattt cggaccgggt acgtcccagg tgccgtagcg    2940
aggacgttgg ttccggatgg gctggcgccg tacctgcgcc agcaactccg ctgggcccgc    3000
agcacttatc gcgacaccgc cctcgcctta cgtataaaga aaatctaag caaatatatc      3060 acctttgaga tatgcgcaca gaatttgggt acggctctct tacttgtgat gaccatgatt    3120
tcgctttcgc tgactacatc agggtcgcaa acgcccgtta tcattctggg tgtcgttgtg    3180
gggatgtcta aataagatg ttgttctgtc gcccttatag cgaaagattt tcggtttcta     3240
tacttcatcg ttcactcagc gttgaatgtt ctaattttaa cgccgttaaa actctatgcc    3300
ctgttaacca ttcgggatag tcggtggcta tcacgcgaga gttcctaagc tagcaagctt    3360
ggacacgctg aaatcaccag tctctctcta caaatctatc tctctctatt ttctccataa    3420
taatgtgtga gtagttccca gataagggaa ttagggttcc tatagggttt cgctcatgtg    3480
ttgagcatat aagaaaccct tagtatgtat ttgtatttgt aaaatacttc tatcaataaa    3540
atttctaatt cctaaaacca aaatccagta ctaaaatcca gacgcgttta attaagcggc    3600
cgcttcgaac ataatgctaa taaaaaattt cctaatcatt attaaatcat ttgtataaac    3660
tataaagaaa ttgatatatt gtaaattaaa cttttaacta ttcattttt tcttaatagt     3720 caataaatta atcataataa ttcataatta atatataatt aacataacca taacatagaa    3780
ttttttattt tggcccatta aaattttta aattttaaat tagtaaagga aaaattacac      3840 tttgaccct taaaaatgat aaaatttat tttaatcctt taaaattgac attttttacta     3900 ttgtaaaaat tacaattta ttttgccccc ctaaaaaatt tttctagctt cgcccttgtg      3960
```

```
tataaatata ttaattacaa tttttatatt tgaattatat aaataattaa attttgatat    4020
ttaaaactaa agtaatctct tttttttta ctttttttta attgaaacat aatggtttaa    4080
atatctatat tacgtatgaa gtaatttaat ataaatttta ttttaattta ttattatata    4140
aattcattta gtaaaaactt ttaatagaat caaaattttt atttgtaaat tcgataactt    4200
ttcttatcaa gtaaatttgt tgaattaaat atttagtaaa attaatattt ttatttataa    4260
atatgataaa tcttataaaa aataaaaaaa tatttaaaat gaaaaacatt gtacaaaggc    4320
tatataagaa gttcaaaagt ttcttcgacc ctgtactcta atagagatta tagatagatt    4380
atagaactat tcatagtttc tcttaacctt taaataagaa ttttagtgta ctcaaactta    4440
catatttta tattgataat aatgtcaata ccagccgagt taagattcac tcgacattaa    4500
tgttgaaaat ttttaataaa agaaaatgtt gataagttaa ttagaacaca agcaagcaca    4560
aatttaagtg gtaagtaagg tccttgaccc taatggaaaa attgttatgt tgattaaatt    4620
ataaattaat ttaaggtaaa attatatttt gacctaaaaa aatgaaaaaa atatatctag    4680
tttcttcgaa aatgaaaaga aaataataaa ttgatacatt ataaaattta tggcatttct    4740
aaaaaaattc tgaatttgat gaaattataa taaaaaaaaa gttttaaaaac atatagattt    4800
caagaatagt gggaaaatta tatttgaaca acactgaaga aatccaaagc attagcagaa    4860
aatggatcac caaatcacaa acaatcagtg aaaagtaatg ataattaatt gaaagtgagc    4920
atttaaattt gatagccata tacttcctgc tgaatttata ggttctcatt aatgcaatta    4980
aattatattt gtcacttttt gaatgaaata aatgacacag ttcatctatt ttttttcttt    5040
caatcgccca tcaaaatacc gaaaatgtaa ctacattaaa aaagatcgaa aaatattcat    5100
attttgatat tttaatagat tgtgtgttca aggcgtaatg tactaaaaaa ttatgatggt    5160
gttgtcgctg tatgtccata aaattcaatg tattcgcatg tatcaaatgt aaattttgac    5220
acaagttatt ctaataataa tcaagttatt tttatacatg agatacatct caaaattatt    5280
tttatatatc cgaaaaatca taacgtacga tcaaactaga aagaggaagt gtcaaaacct    5340
attcattata tgcaaatatg atgggacacg ataccctcat gcattgatat ctcatattgt    5400
ccaaaaactc agaatccttt ttgaaaaaaa aaaattccag agagagtgta taaatccagc    5460
agtgtgcaca agaaacgagc accagttatt gacattcctt tgtaaaaaaa aaaagaagct    5520
gagatcaaga aatatagtga aatatgggtc caacattttc tgggttttta atctcagcac    5580
catgtgcgga attgttggtg ctatcgccca aagagacgtt gctgagattt tgttagaggg    5640
tctgcgaagg ctagagtata gaggatatga ctccgctggt ctggctgtcg ttgatgctga    5700
gggtcatatg acaaggctaa gaaggttagg aaaggttcag atgcttgctc aggcagctga    5760
ggaacatcca ttgcatggag gtactggtat tgcacatacc aggtgggcta ctcatgggga    5820
gccatcagaa gttaatgctc atccacatgt gagtgagcat atcgttgtag ttcacaatgg    5880
gataattgaa aaccacgaac cattgaggga agagttaaag gcaagaggat atactttgt    5940
gagtgagact gacactgagg ttattgcaca tttagtgaac tgggaactca acagggggg    6000
cacattgcgt gaggctgtgt taagagctat tcctcaactt agaggtgcat acggtactgt    6060
tattatggat tcaagacacc cagatactct ccttgcagct agatcaggta gtcccttggt    6120
cataggactt ggaatgggtg aaaatttttat cgctagcgac caattggcct tattgccagt    6180
tacaagacga tttatttcc ttgaagaggg cgatattgct gagattacta gaaggtctgt    6240
gaacatcttt gataagactg gcgctgaggt taaacgtcag gatatcgagt ctaaccttca    6300
atacgatgct ggtgataaag gaatttacag gcattatatg caaaaggaaa tttatgaaca    6360
```

```
accaaatgct atcaaaaaca cacttactgg ccgtatttct catggacagg tcgatttaag    6420
cgagcttggt cctaatgcag acgaactgct atcaaaagtt gagcacatac agatactggc    6480
atgcggaact agttataatt caggaatggt gtctagatac tggttcgaaa gcttggcagg    6540
tataccttgt gatgtagaga tcgcttctga gtttaggtat agaaagtctg ctgtgcgtag    6600
aaattcatta atgattacat tatctcaatc cggagaaaca gcagatacac tggctggatt    6660
gaggctttct aaggaactcg gatatctggg ttcacttgct atttgtaatg taccaggttc    6720
ctcattggtt cgtgaatcag atctagcact tatgacaaat gcaggaactg aaataggtgt    6780
ggcaagtacc aaggctttca caacccaact gaccgtactt ttaatgttgg tagcaaaact    6840
cagtcgatta aggggctag atgcatctat cgaacatgat attgttcacg ggcttcaagc     6900
tctcccttca agaattgaac aaatgctttc acaagataag agaatagagg cattggctga    6960 agattttttcc gacaaacatc acgcattgtt tcttggacgt ggcgatcaat atccaattgc   7020
attggaagga gctttgaagt tgaaagaaat aagttacatt cacgcagaag catatgcagc    7080
tggagaactc aagcatggtc ctttggcact catcgacgct gacatgcccg tgatcgtagt    7140
ggctcctaat aacgaactgc tcgaaaagct taaatcaaat atcgaagagg ttcgagctag    7200
aggaggtcag ctttacgttt tcgctgaaca agatgctgga ttcgtgtcaa gcgataatat    7260
gcatataatt gaaatgcctc acgttgaaga agtgattgca cctatatttt atacagtccc    7320
attgcaactt ctagcttacc atgttgcact tattaaagga actgatgttg atcagcctag    7380
aaacctagca aaatctgtaa cagtcgaata acgcgtggc gcgccgaagc agatcgttca     7440
aacatttggc aataaagttt cttaagattg aatcctgttg ccggtcttgc gatgattatc    7500
atataatttc tgttgaatta cgttaagcat gtaataatta acatgtaatg catgacgtta    7560
tttatgagat gggttttttat gattagagtc ccgcaattat acatttaata cgcgatagaa   7620
aacaaaatat agcgcgcaaa ctaggataaa ttatcgcgcg cggtgtcatc tatgttacta    7680
gatcggaatt cgatatcatt accctgttat ccctaaagct tattaatata acttcgtata    7740
gcatacatta tacgaagtta tgtttcctac gcagcaggtc tcatcaagac gatctacccg    7800
agtaacaatc tccaggagat caaataccct cccaagaagg ttaaagatgc agtcaaaaga    7860
ttcaggacta attgcatcaa gaacacagag aaagacatat ttctcaagat cagaagtact    7920
attccagtat ggacgattca aggcttgctt cataaaccaa ggcaagtaat agagattgga    7980
gtctctaaaa aggtagttcc tactgaatct aaggccatgc atggagtcta agattcaaat    8040
cgaggatcta acagaactcg ccgtgaagac tggcgaacag ttcatacaga gtcttttacg    8100
actcaatgac aagaagaaaa tcttcgtcaa catggtggag cacgacactc tggtctactc    8160
caaaaatgtc aaagatacag tctcagaaga ccaagggct attgagactt ttcaacaaag     8220
gataatttcg gaaacctcc tcggattcca ttgcccagct atctgtcact tcatcgaaag     8280
gacagtagaa aaggaaggtg gctcctacaa atgccatcat tgcgataaag gaaaggctat    8340
cattcaagat gcctctgccg acagtggtcc caaagatgga cccccaccca cgaggagcat    8400
cgtggaaaaa gaagacgttc caaccacgtc ttcaaagcaa gtggattgat gtgcatctc     8460 cactgacgta agggatgacg cacaatccca ctatccttcg caagaccctt cctctatata    8520
aggaagttca tttcatttgg agaggacacg ctgaaatcac cagtctctct ctataaatct    8580
atctctctct ctataacaat ggacccagaa cgacgcccgg ccgacatccg ccgtgccacc    8640
gaggcggaca tgccggcggt ctgcaccatc gtcaaccact acatcgagac aagcacggtc    8700
```

```
aacttccgta ccgagccgca ggaaccgcag gagtggacgg acgacctcgt ccgtctgcgg    8760
gagcgctatc cctggctcgt cgccgaggtg gacggcgagg tcgccggcat cgcctacgcg    8820
ggcccctgga aggcacgcaa cgcctacgac tggacggccg agtcgaccgt gtacgtctcc    8880
ccccgccacc agcggacggg actgggctcc acgctctaca cccacctgct gaagtccctg    8940
gaggcacagg gcttcaagag cgtggtcgct gtcatcgggc tgcccaacga cccgagcgtg    9000
cgcatgcacg aggcgctcgg atatgccccc cgcggcatgc tgcgggcggc cggcttcaag    9060
cacgggaact ggcatgacgt gggtttctgg cagctggact tcagcctgcc ggtaccgccc    9120
cgtccggtcc tgcccgtcac cgagatctga gatcacccgt tctaggatcc gaagcagatc    9180
gttcaaacat ttggcaataa agtttcttaa gattgaatcc tgttgccggt cttgcgatga    9240
ttatcatata atttctgttg aattacgtta agcatgtaat aattaacatg taatgcatga    9300
cgttatttat gagatgggtt tttatgatta gagtcccgca attatacatt taatacgcga    9360
tagaaaacaa aatatagcgc gcaaactagg ataaattatc gcgcgcggtg tcatctatgt    9420
tactagatcg aaacataact tcgtatagca tacattatac gaagttatca aaacgtcgtg    9480
agacagtttg gttaactata acggtcctaa ggtagcgatc gaggcattac ggcattacgg    9540
cactcgcgag ggtccgaatc tatgtcgggt gcggagaaag aggtaatgaa atggcaattt    9600
acaattgaat atatcctgcc g                                              9621
```

<210> SEQ ID NO 15
<211> LENGTH: 7343
<212> TYPE: DNA
<213> ORGANISM: Artificial Sequence
<220> FEATURE:
<223> OTHER INFORMATION: TDNA comprising nucleic acid sequences encoding
      the expansin promoter, a Golgi retention peptide and a NODC
      protein
<220> FEATURE:
<221> NAME/KEY: misc_feature
<222> LOCATION: (1)..(25)
<223> OTHER INFORMATION: right border repeat from the T-DNA of
      Agrobacterium tumefaciens (Zambryski, 1988)
<220> FEATURE:
<221> NAME/KEY: promoter
<222> LOCATION: (26)..(913)
<223> OTHER INFORMATION: sequence including the promoter region of the
      expansin gene of Gossypium hirsutum (cotton)
<220> FEATURE:
<221> NAME/KEY: sig_peptide
<222> LOCATION: (914)..(1018)
<220> FEATURE:
<221> NAME/KEY: gene
<222> LOCATION: (1019)..(2209)
<220> FEATURE:
<221> NAME/KEY: 3'UTR
<222> LOCATION: (2210)..(2442)
<223> OTHER INFORMATION: sequence including the 3' untranslated region
      of the 35S transcript of the Cauliflower Mosaic Virus (Sanfacon et
      al., 1991)
<220> FEATURE:
<221> NAME/KEY: promoter
<222> LOCATION: (2465)..(3303)
<223> OTHER INFORMATION: Pcwp: sequence including the promoter region of
      the expansin gene of Gossypium hirsutum (cotton)
<220> FEATURE:
<221> NAME/KEY: gene
<222> LOCATION: (3304)..(5133)
<223> OTHER INFORMATION: gfaEc: coding region of the glutamine:fructose-
      6-phosphate amidotransferase gene of Escherichia coli (Frohberg
      and Essigmann, 2006)
<220> FEATURE:
<221> NAME/KEY: 3'UTR
<222> LOCATION: (5134)..(5407)
<223> OTHER INFORMATION: 3'nos: sequence including the 3' untranslated
      region of the nopaline synthase gene from the T-DNA of pTiT37

(Depicker et al., 1982)
<220> FEATURE:
<221> NAME/KEY: misc_feature
<222> LOCATION: (5450)..(5449)
<223> OTHER INFORMATION: lox: sequence including the 34bp recognition
     sequence for the Cre recombinase of bacteriophage P1 (Hoess and
     Abremski, 1985)
<220> FEATURE:
<221> NAME/KEY: promoter
<222> LOCATION: (5484)..(6320)
<223> OTHER INFORMATION: P35S3: sequence including the promoter region
     of the Cauliflower Mosaic Virus 35S transcript (Odell et al.,
     1985)
<220> FEATURE:
<221> NAME/KEY: gene
<222> LOCATION: (6321)..(6872)
<223> OTHER INFORMATION: bar: the coding sequence of the
     phosphinothricin acetyltransferase gene of Streptomyces
     hygroscopicus (Thompson et al., 1987).
<220> FEATURE:
<221> NAME/KEY: 3'UTR
<222> LOCATION: (6873)..(7156)
<223> OTHER INFORMATION: 3'nos: sequence including the 3' untranslated
     region of the nopaline synthase gene from the T-DNA of pTiT37
     (Depicker et al., 1982)
<220> FEATURE:
<221> NAME/KEY: misc_feature
<222> LOCATION: (7157)..(7190)
<223> OTHER INFORMATION: lox: sequence including the 34bp recognition
     sequence for the Cre recombinase of bacteriophage P1 (Hoess and
     Abremski, 1985)
<220> FEATURE:
<221> NAME/KEY: misc_feature
<222> LOCATION: (7319)..(7343)
<223> OTHER INFORMATION: left border repeat from the T-DNA of
     Agrobacterium tumefaciens (Zambryski, 1988)

<400> SEQUENCE: 15
aattacaacg gtatatatcc tgccagtact gggcccccte gagggcgatc gctacgtacc      60
tgcagggcgg ccgcgggctg gtatcttttg attggcacaa acagtgcgaa caaagaagac     120
cacacaataa caattttaac aatatactaa tttaaatgaa aaattttcaa taatttaata     180
agttaaccga ggaaaactta ctaagagtta gttacccctg ttaaaataac tttcatgaag     240
taatagaaac ttttagtacg tatcatctta tatagaacaa tttctatttt cagaaagtca     300
agaaaattgt attctagaaa atggcgactt cttcaccttc agtccttccc tgatcggcgc     360
ttgtgaaaaa cgaaaaacct gagtctgatt ggctgactga aaatgaacct actcatcacc     420
attcactatt accaacttca aatgatagg gaattaactg gtaaagtgta actccaccga     480
tggttgaggt ggttggctgg agttaaatga gattttttta gttttgtttc aagtggcttc     540
aattgcaagc aattaggaga ctgcgctgga ataacccctc gctcaacctt ccgccattgt     600
tatggtttaa ttaaacatta tgtttccatc catctatatt tatatccatt aaaacaagcc     660
gttgagcaaa taatggatac tggataccat catatctatg attaaaattt tgcatgtgcc     720
cttttaatgt atagcttaag ccttaattat cctccaaatt tgtactcttt caccacttaa     780
ttggctacgt acggtactta gcgttgcttg tcatcttctg tactacaaac tctttctcat     840
tttgtataaa tagctataca cttttttctct cctcaaatca ataaggttag gtcagccaat     900
tgtttgagct accatgagta aacggaatcc gaagattctg aagatttttc tgtatatgtt     960
acttctcaac tctctctttc tcatcatcta cttcgttttt cactcatcgt cgttttcaag    1020
tgtcgtagat gtgatcggtt tgcttgcgac tgcagcctac gtgacgttgg cgagcgcata    1080
caaggtggtc cagttcatta acgtgtcgag cgtaacggat gtcgctggtc tcgaaagtga    1140
tgctttgccg ctcactccaa gggttgacgt tatcgtgccg acattcaatg agaactccag    1200

```
cacattgctc gagtgcgtcg cttctatatg cgcacaagac taccgcggac caataacgat    1260
tgtcgtggta gacgatgggt cgaccaacaa aacatcattt cacgcagtat gcgacaagta    1320
cgcgagcgac gaaaggttca tatttgtcga acttgatcaa acaaggggga agcgcgccgc    1380
gcaaatggag gccatcagga gaacagacgg agacctgata ctaaacgtag actcggacac    1440
ggttatagat aaggatgttg ttacaaagct tgcgtcgtcc atgagagccc cgaatgtcgg    1500
tggtgtcatg gggcagctcg ttgcaaagaa tcgagaaaga tcttggctta ccagattaat    1560
cgatatggag tactggcttg cgtgtaacga ggagcgcatt gcgcagtcga ggtttggctc    1620
cgtgatgtgt tgttgtgggc cgtgcgccat gtatagaaga tctgcaatta cgccactatt    1680
ggcagaatat gagcaccaga cattcctagg gcgtccgagc aactttggtg aggatcgcca    1740
tctcacaatc ctgatgctga aggcgggatt tcggaccggg tacgtcccag gtgccgtagc    1800
gaggacgttg gttccggatg ggctggcgcc gtacctgcgc cagcaactcc gctgggcccg    1860
cagcacttat cgcgacaccg ccctcgcctt acgtataaag aaaaatctaa gcaaatatat    1920
cacctttgag atatgcgcac agaatttggg tacggctctc ttacttgtga tgaccatgat    1980
ttcgctttcg ctgactacat cagggtcgca acgcccgtt atcattctgg gtgtcgttgt     2040
ggggatgtct ataataagat gttgttctgt cgcccttata gcgaaagatt tcggtttct    2100 atacttcatc gttcactcag cgttgaatgt tctaatttta acgccgttaa aactctatgc    2160
cctgttaacc attcgggata gtcggtggct atcacgcgag agttcctaag ctagcaagct    2220
tggacacgct gaaatcacca gtctctctct acaaatctat ctctctctat tttctccata    2280
ataatgtgtg agtagttccc agataaggga attagggttc ctatagggtt tcgctcatgt    2340
gttgagcata taagaaaccc ttagtatgta tttgtatttg taaaatactt ctatcaataa    2400
aatttctaat tcctaaaacc aaaatccagt actaaaatcc agcccgggtt aattaagcgg    2460
ccgcgggctg gtatcttttg attggcacaa acagtgcgaa caaagaagac cacacaataa    2520
caattttaac aatatactaa tttaaatgaa aaattttcaa taatttaata agttaaccga    2580
ggaaaactta ctaagagtta gttaccccctg ttaaaataac tttcatgaag taatagaaac    2640
ttttagtacg tatcatctta tatagaacaa tttctatttt cagaaagtca agaaaattgt    2700
attctagaaa atggcgactt cttcaccttc agtccttccc tgatcggcgc ttgtgaaaaa    2760
cgaaaaacct gagtctgatt ggctgactga aaatgaacct actcatcacc attcactatt    2820
accaacttca aatgataggg gaattaactg gtaaagtgta actccaccga tggttgaggt    2880
ggttggctgg agttaaatga gatttttta gttttgtttc aagtggcttc aattgcaagc    2940
aattaggaga ctgcgctgga ataaccctc gctcaacctt ccgccattgt tatggtttaa    3000
ttaaacatta tgtttccatc catctatatt tatatccatt aaaacaagcc gttgagcaaa    3060
taatggatac tggataccat catatctatg attaaaattt tgcatgtgcc cttttaatgt    3120
atagcttaag ccttaattat cctccaaatt tgtactcttt caccacttaa ttggctacgt    3180
acggtactta gcgttgcttg tcatcttctg tactacaaac tctttctcat tttgtataaa    3240
tagctataca cttttttctct cctcaaatca ataaggttag gtcagccaat gtttgagct     3300 accatgtgcg gaattgttgg tgctatcgcc caaagacg ttgctgagat tttgttagag      3360
ggtctgcgaa ggctagagta tagaggatat gactccgctg gtctggctgt cgttgatgct    3420
gagggtcata tgacaaggct aagaaggtta ggaaaggttc agatgcttgc tcaggcagct    3480
gaggaacatc cattgcatgg aggtactggt attgcacata ccaggtgggc tactcatggg    3540
gagccatcag aagttaatgc tcatccacat gtgagtgagc atatcgttgt agttcacaat    3600
```

```
gggataattg aaaaccacga accattgagg gaagagttaa aggcaagagg atatacttt     3660 gtgagtgaga ctgacactga ggttattgca catttagtga actgggaact caaacagggg   3720
ggcacattgc gtgaggctgt gttaagagct attcctcaac ttagaggtgc atacggtact   3780
gttattatgg attcaagaca cccagatact ctccttgcag ctagatcagg tagtcccttg   3840
gtcataggac ttggaatggg tgaaaatttt atcgctagcg accaattggc cttattgcca   3900
gttacaagac gatttatttt ccttgaagag ggcgatattg ctgagattac tagaaggtct   3960
gtgaacatct ttgataagac tggcgctgag gttaaacgtc aggatatcga gtctaacctt   4020
caatacgatg ctggtgataa aggaatttac aggcattata tgcaaaagga aatttatgaa   4080
caaccaaatg ctatcaaaaa cacacttact ggccgtattt ctcatggaca ggtcgattta   4140
agcgagcttg gtcctaatgc agacgaactg ctatcaaaag ttgagcacat acagatactg   4200
gcatgcggaa ctagttataa ttcaggaatg gtgtctagat actggttcga aagcttggca   4260 ggtataccttt gtgatgtaga gatcgcttct gagtttaggt atagaaagtc tgctgtgcgt   4320
agaaattcat taatgattac attatctcaa tccggagaaa cagcagatac actggctgga   4380
ttgaggcttt ctaaggaact cggatatctg ggttcacttg ctatttgtaa tgtaccaggt   4440
tcctcattgg ttcgtgaatc agatctagca cttatgacaa atgcaggaac tgaaataggt   4500
gtggcaagta ccaaggcttt cacaacccaa ctgaccgtac ttttaatgtt ggtagcaaaa   4560
ctcagtcgat taaggggct agatgcatct atcgaacatg atattgttca cgggcttcaa   4620 gctctcccttt caagaattga acaaatgctt tcacaagata agagaataga ggcattggct   4680
gaagattttt ccgacaaaca tcacgcattg tttcttggac gtggcgatca atatccaatt   4740
gcattggaag gagctttgaa gttgaaagaa ataagttaca ttcacgcaga agcatatgca   4800
gctggagaac tcaagcatgg tccttttggca ctcatcgacg ctgacatgcc cgtgatcgta   4860
gtggctccta ataacgaact gctcgaaaag cttaaatcaa atatcgaaga ggttcgagct   4920
agaggaggtc agctttacgt tttcgctgaa caagatgctg gattcgtgtc aagcgataat   4980
atgcatataa ttgaaatgcc tcacgttgaa gaagtgattg cacctatatt ttatacagtc   5040
ccattgcaac ttctagctta ccatgttgca cttattaaag gaactgatgt tgatcagcct   5100
agaaacctag caaaatctgt aacagtcgaa taaacgcgtg gcgcgccgaa gcagatcgtt   5160
caaacatttg gcaataaagt ttcttaagat tgaatcctgt tgccggtctt gcgatgatta   5220
tcatataatt tctgttgaat tacgttaagc atgtaataat taacatgtaa tgcatgacgt   5280
tatttatgag atgggttttt atgattagag tcccgcaatt atacatttaa tacgcgatag   5340
aaaacaaaat atagcgcgca aactaggata aattatcgcg cgcggtgtca tctatgttac   5400
tagatcggaa ttcgatatca ttaccctgtt atccctaaag cttattaata taacttcgta   5460
tagcatacat tatacgaagt tatgtttcct acgcagcagg tctcatcaag acgatctacc   5520
cgagtaacaa tctccaggag atcaaatacc ttcccaagaa ggttaaagat gcagtcaaaa   5580
gattcaggac taattgcatc aagaacacag agaaagacat atttctcaag atcagaagta   5640
ctattccagt atggacgatt caaggcttgc ttcataaacc aaggcaagta atagagattg   5700
gagtctctaa aaaggtagtt cctactgaat ctaaggccat gcatggagtc taagattcaa   5760
atcgaggatc taacagaact cgccgtgaag actggcgaac agttcataca gagtcttta   5820 cgactcaatg acaagaagaa aatcttcgtc aacatggtgg agcacgacac tctggtctac   5880
tccaaaaatg tcaaagatac agtctcagaa gaccaaaggg ctattgagac ttttcaacaa   5940
```

```
aggataatttt cgggaaacct cctcggattc cattgcccag ctatctgtca cttcatcgaa    6000
aggacagtag aaaaggaagg tggctcctac aaatgccatc attgcgataa aggaaaggct    6060
atcattcaag atgcctctgc cgacagtggt cccaaagatg gacccccacc cacgaggagc    6120
atcgtggaaa aagaagacgt tccaaccacg tcttcaaagc aagtggattg atgtgacatc    6180
tccactgacg taagggatga cgcacaatcc cactatcctt cgcaagaccc ttcctctata    6240
taaggaagtt catttcattt ggagaggaca cgctgaaatc accagtctct ctctataaat    6300
ctatctctct ctctataaca atggacccag aacgacgccc ggccgacatc cgccgtgcca    6360
ccgaggcgga catgccggcg gtctgcacca tcgtcaacca ctacatcgag acaagcacgg    6420
tcaacttccg taccgagccg caggaaccgc aggagtggac ggacgacctc gtccgtctgc    6480
gggagcgcta tccctggctc gtcgccgagg tggacggcga ggtcgccggc atcgcctacg    6540
cgggcccctg gaaggcacgc aacgcctacg actggacggc cgagtcgacc gtgtacgtct    6600
ccccccgcca ccagcggacg ggactgggct ccacgctcta cacccacctg ctgaagtccc    6660
tggaggcaca gggcttcaag agcgtggtcg ctgtcatcgg gctgcccaac gacccgagcg    6720
tgcgcatgca cgaggcgctc ggatatgccc ccgcggcat gctgcgggcg gccggcttca    6780 agcacggaa ctggcatgac gtgggtttct ggcagctgga cttcagcctg ccggtaccgc    6840
cccgtccggt cctgcccgtc accgagatct gagatcaccc gttctaggat ccgaagcaga    6900
tcgttcaaac atttggcaat aaagtttctt aagattgaat cctgttgccg gtcttgcgat    6960
gattatcata taatttctgt tgaattacgt taagcatgta ataattaaca tgtaatgcat    7020
gacgttattt atgagatggg tttttatgat tagagtcccg caattataca tttaatacgc    7080
gatagaaaac aaaatatagc gcgcaaacta ggataaatta tcgcgcgcgg tgtcatctat    7140
gttactagat cgaaacataa cttcgtatag catacattat acgaagttat caaaacgtcg    7200
tgagacagtt tggttaacta taacggtcct aaggtagcga tcgaggcatt acggcattac    7260
ggcactcgcg agggtccgaa tctatgtcgg gtgcggagaa agaggtaatg aaatggcaat    7320
ttacaattga atatatcctg ccg                                             7343
```

<210> SEQ ID NO 16
<211> LENGTH: 10829
<212> TYPE: DNA
<213> ORGANISM: Artificial Sequence
<220> FEATURE:
<223> OTHER INFORMATION: TDNA comprising nucleic acid sequences encoding
      the E6 promoter, a Golgi retention peptide and a NODC protein
<220> FEATURE:
<221> NAME/KEY: misc_feature
<222> LOCATION: (1)..(25)
<223> OTHER INFORMATION: right border repeat from the T-DNA of
      Agrobacterium tumefaciens (Zambryski, 1988)
<220> FEATURE:
<221> NAME/KEY: promoter
<222> LOCATION: (26)..(2712)
<223> OTHER INFORMATION: sequence including the promoter region of the
      E6 gene of Gossypium barbadense (cotton)
<220> FEATURE:
<221> NAME/KEY: sig_peptide
<222> LOCATION: (2713)..(2817)
<220> FEATURE:
<221> NAME/KEY: gene
<222> LOCATION: (2818)..(4008)
<220> FEATURE:
<221> NAME/KEY: 3'UTR
<222> LOCATION: (4009)..(4244)
<223> OTHER INFORMATION: sequence including the 3' untranslated region
      of the 35S transcript of the Cauliflower Mosaic Virus (Sanfacon et
      al., 1991)
<220> FEATURE:

```
<221> NAME/KEY: promoter
<222> LOCATION: (4262)..(6901)
<223> OTHER INFORMATION: Pcwp: sequence including the promoter region of
      the E6 gene of Gossypium barbadense (cotton)
<220> FEATURE:
<221> NAME/KEY: gene
<222> LOCATION: (6902)..(8731)
<223> OTHER INFORMATION: gfaEc: coding region of the glutamine:fructose-
      6-phosphate amidotransferase gene of Escherichia coli (Frohberg
      and Essigmann, 2006)
<220> FEATURE:
<221> NAME/KEY: 3'UTR
<222> LOCATION: (8732)..(9005)
<223> OTHER INFORMATION: 3'nos: sequence including the 3' untranslated
      region of the nopaline synthase gene from the T-DNA of pTiT37
      (Depicker et al., 1982)
<220> FEATURE:
<221> NAME/KEY: misc_feature
<222> LOCATION: (9048)..(9085)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: promoter
<222> LOCATION: (9086)..(9918)
<223> OTHER INFORMATION: P35S3: sequence including the promoter region
      of the Cauliflower Mosaic Virus 35S transcript (Odell et al.,
      1985)
<220> FEATURE:
<221> NAME/KEY: gene
<222> LOCATION: (9919)..(10470)
<223> OTHER INFORMATION: bar: the coding sequence of the
      phosphinothricin acetyltransferase gene of Streptomyces
      hygroscopicus (Thompson et al., 1987).
<220> FEATURE:
<221> NAME/KEY: 3'UTR
<222> LOCATION: (10471)..(10750)
<223> OTHER INFORMATION: 3'nos: sequence including the 3' untranslated
      region of the nopaline synthase gene from the T-DNA of pTiT37
      (Depicker et al., 1982)
<220> FEATURE:
<221> NAME/KEY: misc_feature
<222> LOCATION: (10751)..(10788)
<223> OTHER INFORMATION: lox: sequence including the 34bp recognition
      sequence for the Cre recombinase of bacteriophage P1 (Hoess and
      Abremski, 1985)
<220> FEATURE:
<221> NAME/KEY: misc_feature
<222> LOCATION: (10805)..(10829)
<223> OTHER INFORMATION: left border repeat from the T-DNA of
      Agrobacterium tumefaciens (Zambryski, 1988)

<400> SEQUENCE: 16
aattacaacg gtatatatcc tgccagtact gggcccccte gagggcgatc gctacgtacc      60
tgcagggcgg ccgcgtcaac ggatcaacat tcaattacaa taaagagtat agatagatac     120
atcaatacta tccagccctc tttcatgatg atgttgcaag ttttgcactc caccccata      180 ttattatgaa gaggagaaat tcctgttaca acattaattg agctttattt tctaagaaat     240
gacttctaac attaataaat ttgaatcaat ttatagctat ttctcgtact ctttcgtagt     300
atagctttct ttttatgcta aaacaggaga tgattataag acgtgaagtt gtcttaagat     360
taacaaggca gttagatgca tttaaattgg tatttaagga tatgtctgta tataactaga     420
actaattaag attacaatac actgcaaaat gattccacct ttttttttt tttggttctc      480 tcttttatat gatcaaatac aatgttgata tgaacaaggt tttgcagttg tagaaaatcg     540
tggaggactt ttttttttaa aaaagaaaga taaaattcat aaaaaaatgt gaagttaagc     600
atatttagtg atgggtgggg tatgggtgg tttgctaaca tggaatgcgc atggcagatt      660
ggcactttaa agaagggatg gggccgaggg ggcgggagtt gttaaatcct cggcgtagaa     720
aaaggtcagt aagcgtgtcc ctggcattag acaaggagag ggggtagcac atgcacagcc     780
```

```
caactatatc tctttatttt atgtcccact ccactccccc tcatctctgc cgcaacatta    840
aataccttat gcatccttac tattcataat ggttttttt gttgggttga tgttacaaaa     900
ttaaatttt tattatagat gtattaatat ttttaaaaat atataagatt tttttaagt      960
aggagtttaa tctttggtgg tgatgttgat tttagatata ttccccaccc gcaagtagat    1020
atcatacatt ctaatataat ttaaaaaaaa gtataactaa aatatatttt atatttttt     1080
atattttt gaattttaa atttaaaaa attaattaaa tgttcatgtg tcatctacat         1140
gtatgcaacg ttagcgaagt ttaaaatata ttaattttt cattcgtgat ttgaaaaaaa     1200
aaaggtaagt ttaaaggtta aacaagcata aatctaaata aatagttaaa ataatttttt    1260
ttataaagtt agagaattaa ataaattatt attttattta aaaataattt tcaataaatt    1320
actaatttag tcacataatc taatataatt taaaaaataa ttattaacat tttaatttgt    1380
atgaattctt gttatgtatg gattcaaacc cgttcgttcc atcaacaaat tgatctgcat    1440
gagacttaag ggttagaatt ttgtgtaacc cttttcctc ctaattttta cttttaaaaa     1500
gaaattgcaa tacaattttt tttttataga attctcctat ttttatttat ttatttgctt   1560
aggaagtttt actgacactg ctttattttt tccatcaatc aaatttaaga gacaattcac    1620
ttttataat taacaaaaaa aaacaaaaag aaaataaaag aaattacttt tttcttttc     1680
gtgttcgata caagatagat gaaatatgaa aaataaaatg aaatgaaaat atattactag    1740
tgatatatga cctccattat gtaggggaaa gaaataaaaa ttatattaat ttatgatact   1800
tccataatgt ggttaaaaat aattatctag tattttttg taaaaaaaaa aaagttgata    1860
tctatgctac taatgaggtt tcttagtgag tttgttacta ctaataaagt ttatttgcat   1920
ggttgagacc ttatgctttt caaataccca tatttgaatt ttaaaaattg tgaattttta   1980
ttatatttaa aaaacaagtt atttatataa ctagtaatgt attattttga cttttttta    2040
atcgagttaa tgttggttat ttcgttatac caattcaata aaatattta tttatattaa    2100
attatagcat acctcacgat gtgggtgaag taaaattatt taacaaatat atttgaaaa    2160
attgataaaa atactaaatg aggttttggt tgaatagtaa gatataatta ttacaaatta   2220
taaatatgta ggttcaaaat ctatcatgtg tatatttgta ctattattct atataaattg   2280
ataaccttat aaaagtatct aatttagttt atggttgatt gatcgataat accaaattta   2340
ttaaaaatta atattagtaa agatatatag tacaaaacta aacataaaat tttatatgtt    2400
aaggaaatag cggaaaaaat atcatatttg tagaactgtt tagcagtgtg ggagaatggg    2460
atcattacaa ggaaaaatga aatatatatc attaatacca aacataaaag aaagcgtctt   2520
ttgataaagt tgttattggt gtaatgtgaa gggaccacaa tcatcaccat tcaccacttg    2580
ctcctaattg agttgaaatc tttttacaac atagaaaact agaagatcgc cctttcttgc   2640
ttcatatata tagatttgt atcatcgcaa tttcacatca cacacacaag taaagcatta    2700
gcaaccatag ccatgagtaa acggaatccg aagattctga agatttttct gtatatgtta   2760
cttctcaact ctctctttct catcatctac ttcgttttc actcatcgtc gttttcaagt    2820
gtcgtagatg tgatcggttt gcttgcgact gcagcctacg tgacgttggc gagcgcatac    2880
aaggtggtcc agttcattaa cgtgtcgagc gtaacggatg tcgctggtct cgaaagtgat    2940
gctttgccgc tcactccaag ggttgacgtt atcgtgccga cattcaatga gaactccagc    3000
acattgctcg agtgcgtcgc ttctatatgc gcacaagact accgcggacc aataacgatt    3060
gtcgtggtag acgatgggtc gaccaacaaa acatcatttc acgcagtatg cgacaagtac    3120
```

```
gcgagcgacg aaaggttcat atttgtcgaa cttgatcaaa acaaggggaa gcgcgccgcg    3180
caaatggagg ccatcaggag aacagacgga gacctgatac taaacgtaga ctcggacacg    3240
gttatagata aggatgttgt tacaaagctt gcgtcgtcca tgagagcccc gaatgtcggt    3300
ggtgtcatgg ggcagctcgt tgcaaagaat cgagaaagat cttggcttac cagattaatc    3360
gatatggagt actggcttgc gtgtaacgag gagcgcattg cgcagtcgag gtttggctcc    3420
gtgatgtgtt gttgtgggcc gtgcgccatg tatagaagat ctgcaattac gccactattg    3480
gcagaatatg agcaccagac attcctaggg cgtccgagca actttggtga ggatcgccat    3540
ctcacaatcc tgatgctgaa ggcgggattt cggaccgggt acgtcccagg tgccgtagcg    3600
aggacgttgg ttccggatgg gctggcgccg tacctgcgcc agcaactccg ctgggcccgc    3660
agcacttatc gcgacaccgc cctcgcctta cgtataaaga aaaatctaag caaatatatc    3720
acctttgaga tatgcgcaca gaatttgggt acggctctct tacttgtgat gaccatgatt    3780
tcgctttcgc tgactacatc agggtcgcaa acgcccgtta tcattctggg tgtcgttgtg    3840
gggatgtcta taataagatg ttgttctgtc gcccttatag cgaaagattt tcggtttcta    3900
tacttcatcg ttcactcagc gttgaatgtt ctaattttaa cgccgttaaa actctatgcc    3960
ctgttaacca ttcgggatag tcggtggcta tcacgcgaga gttcctaagc tagcaagctt    4020
ggacacgctg aaatcaccag tctctctcta caaatctatc tctctctatt ttctccataa    4080
taatgtgtga gtagttccca gataagggaa ttagggttcc tatagggttt cgctcatgtg    4140
ttgagcatat aagaaaccct tagtatgtat ttgtatttgt aaaatacttc tatcaataaa    4200
atttctaatt cctaaaacca aaatccagta ctaaaatcca gcccgggtta attaagcggc    4260
cgcgtcaacg gatcaacatt caattacaat aaagagtata gatagataca tcaatactat    4320
ccagccctct ttcatgatga tgttgcaagt tttgcactcc accccatat tattatgaag     4380
aggagaaatt cctgttacaa cattaattga gctttatttt ctaagaaatg acttctaaca    4440
ttaataaatt tgaatcaatt tatagctatt tctcgtactc tttcgtagta tagctttctt    4500
tttatgctaa aacaggagat gattataaga cgtgaagttg tcttaagatt aacaaggcag    4560
ttagatgcat ttaaattggt atttaaggat atgtctgtat ataactagaa ctaattaaga    4620
ttacaataca ctgcaaaatg attccacctt ttttttttttt ttggttctct cttttatatg    4680
atcaaataca atgttgatat gaacaaggtt ttgcagttgt agaaaatcgt ggaggacttt    4740
ttttttaaaa aagaaagat aaaattcata aaaaaatgtg aagttaagca tatttagtga    4800
tgggtggggt atgggtggt ttgctaacat ggaatgcgca tggcagattg gcactttaaa     4860
gaagggatgg ggccgagggg gcgggagttg ttaaatcctc ggcgtagaaa aaggtcagta    4920
agcgtgtccc tggcattaga caaggagagg gggtagcaca tgcacagccc aactatatct    4980
ctttatttta tgtcccactc cactccccct catctctgcc gcaacattaa ataccttatg    5040
catccttact attcataatg gttttttttg ttgggttgat gttacaaaat taaattttttt    5100
attatagatg tattaatatt tttaaaaata tataagattt ttttaagta ggagtttaat     5160
ctttggtggt gatgttgatt ttagatatat tccccacccg caagtagata tcatacattc    5220
taatataatt taaaaaaag tataactaaa atatattta tatttttta tattttttg        5280
aattttaaa ttttaaaaaa ttaattaaat gttcatgtgt catctacatg tatgcaacgt     5340
tagcgaagtt taaatatat taattttttc attcgtgatt tgaaaaaaaa aaggtaagtt     5400
taaaggttaa acaagcataa atctaaataa atagttaaaa taattttttt tataaagtta    5460
gagaattaaa taaattatta ttttattaa aaataatttt caataaatta ctaatttagt     5520
```

```
cacataatct aatataattt aaaaaataat tattaacatt ttaatttgta tgaattcttg    5580
ttatgtatgg attcaaaccc gttcgttcca tcaacaaatt gatctgcatg agacttaagg    5640
gttagaattt tgtgtaaccc tttttcctcc taatttttac ttttaaaaag aaattgcaat    5700
acaatttttt ttttatagaa ttctcctatt tttatttatt tatttgctta ggaagtttta    5760
ctgacactgc ttttattttt ccatcaatca aatttaagag acaattcact ttttataatt    5820
aacaaaaaaa aacaaaaaga aaataaaaga aattacttt tctttttcg tgttcgatac     5880 aagatagatg aaatatgaaa aataaaatga aatgaaaata tattactagt gatatatgac    5940
ctccattatg taggggaaag aaataaaaat tatattaatt tatgatactt ccataatgtg    6000
gttaaaaata attatctagt atttttttgt aaaaaaaaaa aagttgatat ctatgctact    6060
aatgaggttt cttagtgagt ttgttactac taataaagtt tatttgcatg gttgagacct    6120
tatgcttttc aaatacccat atttgaattt taaaaattgt gaattttat tatatttaaa     6180 aaacaagtta tttatataac tagtaatgta ttattttgac ttttttttaa tcgagttaat    6240
gttggttatt tcgttatacc aattcaataa aatatttat ttatattaaa ttatagcata     6300
cctcacgatg tgggtgaagt aaaattattt aacaaatata ttttgaaaaa ttgataaaaa    6360
tactaaatga ggttttggtt gaatagtaag atataattat tacaaattat aaatatgtag    6420
gttcaaaatc tatcatgtgt atatttgtac tattattcta tataaattga taaccttata    6480
aaagtatcta atttagttta tggttgattg atcgataata ccaaatttat taaaaattaa    6540
tattagtaaa gatatatagt acaaaactaa acataaaatt ttatatgtta aggaaatagc    6600
ggaaaaaata tcatatttgt agaactgttt agcagtgtgg gagaatggga tcattacaag    6660
gaaaaatgaa atatatatca ttaataccaa acataaaaga aagcgtctt tgataaagtt      6720 gttattggtg taatgtgaag ggaccacaat catcaccatt caccacttgc tcctaattga    6780
gttgaaatct ttttacaaca tagaaaacta gaagatcgcc ctttcttgct tcatatatat    6840
agattttgta tcatcgcaat ttcacatcac acacacaagt aaagcattag caaccatagc    6900
catgtgcgga attgttggtg ctatcgccca aagagacgtt gctgagattt tgttagaggg    6960
tctgcgaagg ctagagtata gaggatatga ctccgctggt ctggctgtcg ttgatgctga    7020
gggtcatatg acaaggctaa gaaggttagg aaaggttcag atgcttgctc aggcagctga    7080
ggaacatcca ttgcatggag gtactggtat tgcacatacc aggtgggcta ctcatgggga    7140
gccatcagaa gttaatgctc atccacatgt gagtgagcat atcgttgtag ttcacaatgg    7200
gataattgaa aaccacgaac cattgaggga agagttaaag gcaagaggat atactttttgt   7260 gagtgagact gacactgagg ttattgcaca tttagtgaac tgggaactca aacaggggg    7320 cacattgcgt gaggctgtgt taagagctat tcctcaactt agaggtgcat acggtactgt    7380
tattatggat tcaagacacc cagatactct ccttgcagct agatcaggta gtcccttggt    7440
cataggactt ggaatgggtg aaaattttat cgctagcgac caattggcct tattgccagt    7500
tacaagacga tttatttttcc ttgaagaggg cgatattgct gagattacta gaaggtctgt    7560
gaacatcttt gataagactg gcgctgaggt taaacgtcag gatatcgagt ctaaccttca    7620
atacgatgct ggtgataaag gaatttacag gcattatatg caaaaggaaa tttatgaaca    7680
accaaatgct atcaaaaaca cacttactgg ccgtatttct catggacagg tcgatttaag    7740
cgagcttggt cctaatgcag acgaactgct atcaaaagtt gagcacatac agatactggc    7800
atgcggaact agttataatt caggaatggt gtctagatac tggttcgaaa gcttggcagg    7860
```

```
tataccttgt gatgtagaga tcgcttctga gtttaggtat agaaagtctg ctgtgcgtag    7920
aaattcatta atgattacat tatctcaatc cggagaaaca gcagatacac tggctggatt    7980
gaggctttct aaggaactcg gatatctggg ttcacttgct atttgtaatg taccaggttc    8040
ctcattggtt cgtgaatcag atctagcact tatgacaaat gcaggaactg aaataggtgt    8100
ggcaagtacc aaggctttca cacccaact gaccgtactt ttaatgttgg tagcaaaact    8160
cagtcgatta aaggggctag atgcatctat cgaacatgat attgttcacg gcttcaagc    8220
tctcccttca agaattgaac aaatgctttc acaagataag agaatagagg cattggctga    8280
agatttttcc gacaaacatc acgcattgtt tcttggacgt ggcgatcaat atccaattgc    8340
attggaagga gctttgaagt tgaaagaaat aagttacatt cacgcagaag catatgcagc    8400
tggagaactc aagcatggtc ctttggcact catcgacgct gacatgcccg tgatcgtagt    8460
ggctcctaat aacgaactgc tcgaaaagct taaatcaaat atcgaagagg ttcgagctag    8520
aggaggtcag ctttacgttt tcgctgaaca agatgctgga ttcgtgtcaa gcgataatat    8580
gcatataatt gaaatgcctc acgttgaaga agtgattgca cctatatttt atacagtccc    8640
attgcaactt ctagcttacc atgttgcact tattaaagga actgatgttg atcagcctag    8700
aaacctagca aaatctgtaa cagtcgaata acgcgtggc gcgccgaagc agatcgttca    8760
aacatttggc aataaagttt cttaagattg aatcctgttg ccggtcttgc gatgattatc    8820
atataatttc tgttgaatta cgttaagcat gtaataatta acatgtaatg catgacgtta    8880
tttatgagat gggttttat gattagagtc ccgcaattat acatttaata cgcgatagaa    8940
aacaaaatat agcgcgcaaa ctaggataaa ttatcgcgcg cggtgtcatc tatgttacta    9000
gatcggaatt cgatatcatt accctgttat ccctaaagct tattaatata acttcgtata    9060
gcatacatta tacgaagtta tgtttcctac gcagcaggtc tcatcaagac gatctacccg    9120
agtaacaatc tccaggagat caaatacctt cccaagaagg ttaaagatgc agtcaaaaga    9180
ttcaggacta attgcatcaa gaacacagag aaagacatat ttctcaagat cagaagtact    9240
attccagtat ggacgattca aggcttgctt cataaaccaa ggcaagtaat agagattgga    9300
gtctctaaaa aggtagttcc tactgaatct aaggccatgc atggagtcta agattcaaat    9360
cgaggatcta acagaactcg ccgtgaagac tggcgaacag ttcatacaga gtcttttacg    9420
actcaatgac aagaagaaaa tcttcgtcaa catggtggag cacgacactc tggtctactc    9480
caaaaatgtc aaagatacag tctcagaaga ccaaagggct attgagactt ttcaacaaag    9540
gataatttcg ggaaacctcc tcggattcca ttgcccagct atctgtcact tcatcgaaag    9600
gacagtagaa aaggaaggtg gctcctacaa atgccatcat tgcgataaag gaaaggctat    9660
cattcaagat gcctctgccg acagtggtcc caaagatgga cccccacca cgaggagcat    9720
cgtggaaaaa gaagacgttc caaccacgtc ttcaaagcaa gtggattgat gtgacatctc    9780
cactgacgta agggatgacg cacaatccca ctatccttcg caagacccct tctctatata    9840
aggaagttca tttcatttgg agaggacacg ctgaaatcac cagtctctct ctataaatct    9900
atctctctct ctataacaat ggacccagaa cgacgcccgg ccgacatccg ccgtgccacc    9960
gaggcggaca tgccggcggt ctgcaccatc gtcaaccact acatcgagac aagcacggtc   10020
aacttccgta ccgagccgca ggaaccgcag gagtggacgg acgacctcgt ccgtctgcgg   10080
gagcgctatc cctggctcgt cgccgaggtg gacggcgagg tcgccggcat cgcctacgcg   10140
ggcccctgga aggcacgcaa cgcctacgac tggacggccg agtcgaccgt gtacgtctcc   10200
ccccgccacc agcggacggg actgggctcc acgctctaca cccacctgct gaagtccctg   10260
```

```
gaggcacagg gcttcaagag cgtggtcgct gtcatcgggc tgcccaacga cccgagcgtg   10320
cgcatgcacg aggcgctcgg atatgccccc cgcggcatgc tgcgggcggc cggcttcaag   10380
cacgggaact ggcatgacgt gggtttctgg cagctggact tcagcctgcc ggtaccgccc   10440
cgtccggtcc tgcccgtcac cgagatctga gatcacccgt tctaggatcc gaagcagatc   10500
gttcaaacat ttggcaataa agtttcttaa gattgaatcc tgttgccggt cttgcgatga   10560
ttatcatata atttctgttg aattacgtta agcatgtaat aattaacatg taatgcatga   10620
cgttatttat gagatgggtt tttatgatta gagtcccgca attatacatt taatacgcga   10680
tagaaaacaa atatagcgc  gcaaactagg ataaattatc gcgcgcggtg tcatctatgt   10740
tactagatcg aaacataact tcgtatagca tacattatac gaagttatat tcgagcatgg   10800
agccatttac aattgaatat atcctgccg                                     10829
```

<210> SEQ ID NO 17
<211> LENGTH: 413
<212> TYPE: PRT
<213> ORGANISM: Rhizobium sp.

<400> SEQUENCE: 17

```
Met Asp Leu Leu Gly Thr Thr Gly Ala Val Ala Ile Ser Leu Tyr Ala
1               5                   10                  15

Ala Leu Ser Thr Ala Tyr Lys Gly Met Gln Ala Ile Tyr Ala Leu Pro
            20                  25                  30

Thr Asn Thr Thr Ala Ala Ser Thr Pro Val Thr Gly Ser Gly Ala Pro
        35                  40                  45

Pro Ser Val Asp Val Ile Val Pro Cys Tyr Asn Glu Asp Pro Arg Ala
50                  55                  60

Leu Ser Ala Cys Leu Ala Ser Ile Ala Lys Gln Asp Tyr Ala Gly Glu
65                  70                  75                  80

Leu Arg Val Tyr Val Val Asp Asp Gly Ser Gly Asn Arg Asn Ala Ile
                85                  90                  95

Ile Pro Val His Asp His Tyr Ala Cys Asp Pro Arg Phe Arg Phe Ile
            100                 105                 110

Leu Met Pro Lys Asn Val Gly Lys Arg Lys Ala Gln Ile Val Ala Ile
        115                 120                 125

Arg Glu Ser Ser Gly Asp Leu Val Leu Asn Val Asp Ser Asp Thr Thr
    130                 135                 140

Ile Ala Pro Asp Val Val Thr Lys Leu Ala Leu Lys Met Tyr Ser Pro
145                 150                 155                 160

Ala Val Gly Ala Ala Met Gly Gln Leu Thr Ala Ser Asn Arg Ser Asp
                165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
        195                 200                 205

Gly Pro Cys Ala Met Tyr Arg Arg Ser Ala Leu Leu Leu Leu Leu Asp
    210                 215                 220

Lys Tyr Glu Thr Gln Leu Phe Arg Gly Arg Pro Ser Asp Phe Gly Glu
225                 230                 235                 240

Asp Arg His Leu Thr Ile Leu Met Leu Asn Ala Gly Phe Arg Thr Glu
                245                 250                 255

Tyr Val Pro Glu Ala Ile Ala Ala Thr Val Val Pro Asn Ser Met Gly
            260                 265                 270
```

Ala Tyr Leu Arg Gln Gln Leu Arg Trp Ala Arg Ser Thr Phe Arg Asp
            275                 280                 285

Thr Leu Leu Ala Leu Arg Leu Leu Pro Gly Leu Asp Arg Tyr Leu Thr
        290                 295                 300

Leu Asp Val Ile Gly Gln Asn Leu Gly Pro Leu Leu Leu Ala Leu Ser
305                 310                 315                 320

Val Leu Thr Gly Leu Ala Gln Leu Ala Leu Thr Ala Thr Val Pro Trp
            325                 330                 335

Ser Thr Ile Leu Met Ile Ala Ser Met Thr Met Val Arg Cys Gly Val
            340                 345                 350

Ala Ala Phe Arg Ala Arg Glu Leu Arg Phe Leu Gly Phe Ser Leu His
            355                 360                 365

Thr Leu Leu Asn Val Ala Leu Leu Leu Pro Leu Lys Ala Tyr Ala Leu
        370                 375                 380

Cys Thr Leu Ser Asn Ser Asp Trp Leu Ser Arg Gly Ser Pro Ala Ala
385                 390                 395                 400

Ala Pro Asn Gly Val Lys Asp Ser Pro Glu Pro His Cys
            405                 410

```
<210> SEQ ID NO 18
<211> LENGTH: 12
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 18
```

Pro Xaa Val Asp Val Ile Xaa Pro Xaa Xaa Asn Glu
1               5                   10

```
<210> SEQ ID NO 19
<211> LENGTH: 7
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (6)..(6)
<223> OTHER INFORMATION: Xaa can be any naturally occurring amino acid

<400> SEQUENCE: 19
```

Val Asp Asp Gly Ser Xaa Asn
1               5

```
<210> SEQ ID NO 20
<211> LENGTH: 17
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
```

```
<222> LOCATION: (3)..(4)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid

<400> SEQUENCE: 20

Gly Asp Xaa Xaa Leu Asp Val Asp Ser Asp Thr Xaa Xaa Xaa Xaa Asp
1               5                   10                  15

Val

<210> SEQ ID NO 21
<211> LENGTH: 6
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 21

Gly Xaa Xaa Met Gly Gln
1               5

<210> SEQ ID NO 22
<211> LENGTH: 32
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 22

Asp Met Glu Tyr Trp Leu Ala Cys Asn Glu Glu Arg Xaa Xaa Gln Xaa
1               5                   10                  15

Arg Phe Gly Xaa Val Met Xaa Cys Xaa Gly Xaa Cys Xaa Met Tyr Arg
            20                  25                  30

<210> SEQ ID NO 23
<211> LENGTH: 16
<212> TYPE: PRT
```

```
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 23

Phe Arg Thr Xaa Tyr Xaa Pro Xaa Ala Xaa Ala Xaa Thr Xaa Val Pro
1               5                   10                  15

<210> SEQ ID NO 24
<211> LENGTH: 18
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 24

Tyr Leu Xaa Gln Gln Leu Arg Trp Ala Arg Ser Thr Xaa Arg Xaa Thr
1               5                   10                  15

Xaa Leu

<210> SEQ ID NO 25
<211> LENGTH: 8
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
```

```
<400> SEQUENCE: 25

Gln Asn Xaa Gly Xaa Xaa Leu Leu
1               5

<210> SEQ ID NO 26
<211> LENGTH: 26
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 26

Arg Phe Xaa Phe Xaa Xaa Xaa His Xaa Xaa Xaa Asn Xaa Xaa Xaa Leu
1               5                   10                  15

Xaa Pro Leu Lys Xaa Tyr Ala Leu Xaa Thr
            20                  25

<210> SEQ ID NO 27
<211> LENGTH: 40
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 27

Trp Leu Thr Arg Leu Ile Asp Met Glu Tyr Trp Leu Ala Cys Asn Glu
1               5                   10                  15

Glu Arg Xaa Xaa Gln Xaa Arg Phe Gly Xaa Val Met Cys Cys Cys Gly
            20                  25                  30

Pro Cys Ala Met Tyr Arg Arg Ser
```

<210> SEQ ID NO 28
<211> LENGTH: 47
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 28

Leu Leu Xaa Xaa Tyr Glu Xaa Gln Xaa Phe Xaa Gly Xaa Pro Ser Xaa
1               5                   10                  15

Phe Gly Glu Asp Arg His Leu Thr Ile Leu Met Leu Xaa Ala Gly Phe
            20                  25                  30

Arg Thr Xaa Tyr Val Pro Xaa Ala Xaa Ala Xaa Thr Xaa Val Pro
        35                  40                  45

<210> SEQ ID NO 29
<211> LENGTH: 19
<212> TYPE: PRT
<213> ORGANISM: Artificial sequence
<220> FEATURE:
<223> OTHER INFORMATION: NODC protein conserved motif
<220> FEATURE:
<221> NAME/KEY: misc_feature
<222> LOCATION: (13)..(13)

```
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 29

Tyr Leu Arg Gln Gln Leu Arg Trp Ala Arg Ser Thr Xaa Arg Asp Thr
1               5                   10                  15

Xaa Leu Ala

<210> SEQ ID NO 30
<211> LENGTH: 5
<212> TYPE: PRT
<213> ORGANISM: Artificial sequence
<220> FEATURE:
<223> OTHER INFORMATION: targeting peptide from Arabidopsis DAGAT1

<400> SEQUENCE: 30

Tyr Tyr His Asp Leu
1               5

<210> SEQ ID NO 31
<211> LENGTH: 5
<212> TYPE: PRT
<213> ORGANISM: Artificial sequence
<220> FEATURE:
<223> OTHER INFORMATION: targeting peptide from Arabidopsis DAGAT2

<400> SEQUENCE: 31

Leu Lys Leu Glu Ile
1               5
```

METHODS FOR ALTERING THE REACTIVITY OF PLANT CELL WALLS

CROSS-REFERENCE TO RELATED APPLICATIONS

This application is a § 371 U.S. National Stage of International Application No. PCT/EP2011/004929, filed Sep. 30, 2011, which claims the benefit of U.S. Patent Application Ser. No. 61/394,109, filed Oct. 18, 2010, and European Patent Application Serial No. 10013693.6, filed Oct. 15, 2010, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "bcs102016.txt", created on Sep. 27, 2011, and having a size of 115 kilobytes and is filed concurrently with the specification. The sequence listing contained in this ASCII formatted document is part of the specification and is herein incorporated by reference in its entirety.

The present invention relates to the modification of the reactivity of plant cell walls, including secondary plant cell walls, particularly as they can be found in natural fibers of fiber producing plants. In particular, the present invention is related to cotton fibers with altered reactivity. The modified reactivity could be applied in methods for dyeing cell wall containing plant derived material such as natural fibers, using fiber-reactive dyes, to improve e.g. colorfastness, or to decrease the volumes of waste-water used during the dyeing process. The modified reactivity could also be applied to improve the reactivity of the natural fibers with reactants such as flame retardants, water, oil and soil repellents, anticrease agents, softeners, antistatic agents, fluorescent whitening agents etc.

The current invention provides methods to increase the efficiency of production of N-acetylglucosamine oligomers in plant cell walls, with the further advantage that the plants produced by methods of the invention do not show retardation in root growth.

BACKGROUND ART

Natural fibers, including cellulose containing natural fibers from plants, such as cotton and linen, have been used by mankind for more than 5000 years. Natural cellulose containing fibers, however, do not possess the chemical versatility of synthetic fibers, due to the relative inert nature of the cellulose consisting of β-1-4 linked glucose monomers.

This relatively inert nature is e.g. apparent during the dyeing process of cotton fibers and fabrics. Several types of dyes are used to color cotton, such as direct dyes and, most importantly, fiber-reactive dyes, which are both anionic molecules. Cotton itself develops an anionic charge in water, so that without special treatment, the uptake of dye by the fiber or fabric is quite elaborate.

Direct dyes create a relatively weak hydrogen bond with the cellulose polymer forming a semi-permanent attachment. Direct dyes are easier to use and less expensive than fiber-reactive dyes, but do not withstand well washing. Fiber-reactive dyes are molecules that combine chromophores with a reactive group that forms strong covalent bonds with the fiber via reaction with hydroxyl groups. The covalent bonds provide a good resistance of the dyed fiber against laundering.

During the dyeing process, large amounts of electrolytes are needed to shield the anionic dyes from the anionic fiber charges. Unreacted hydrolyzed dyes (up to 40%) need to be removed by multiple washing steps, generating large volumes of wastewater, also containing the above mentioned electrolytes.

Providing the cellulose fiber with a positive electric charge, e.g. by incorporation of positively charged chemical compounds, could therefore improve the dyeability of natural cellulose fibers, as well as improve any chemical reaction of the modified cellulose fiber with negatively charged chemical compounds. It would also make the use of acidic dyes possible.

Several publications have described the incorporation into or coating of chitosan oligomers into cellulose fibers to make chitosan/cellulose blends, yarns or fabrics. Chitosan is a positively charged polymer of glucosamine, which can be obtained by deacetylation of chitin, e.g. by alkalic treatments. Chitin itself is a polymer of β-1-4 linked N-acetylglucosamine (GlcNAc).

US patent application US2003/0134120 describes the coating of natural fibers with chitosan.

Liu et al. (*Carbohydrate Polymers* 44(2003) 233-238) describe a method for coating cotton fibers with chitosan, by oxidation of the cotton thread with potassium periodate at 60° C. in water and subsequent treatment with a solution of chitosan in aqueous acetic acid. With the chitosan coating, the cotton fiber surface became physiologically and biologically active. Since the chemical reactivity of the amino group is greater than the hydroxyl group of cellulose monomers, the fiber has more potential for further chemical modification. Moreover, the smooth surface of the cotton fiber became coarse, suggesting a greater potential for drug absorption and controlled release thereof.

Based on the physiological function of chitosan in inhibiting e.g. dermatophytes, many functional clothes, fabrics and fibers employ cellulose-chitosan blend fibers, cellulose fiber-chitosan conjugates and fabrics coated with chitosan-containing resins.

WO 00/09729 describes the expression of chitin synthase and chitin deacetylase genes in plants to alter the cell wall for industrial uses and improved disease resistance. Specifically cited uses are: to provide a single plant source of cellulose, chitin and chitosan, to increase tensile strength and to increase brittle snap. Specifically suggested chitin synthase genes are derived from fungal organisms. No experimental data are provided on the production of chitin or chitosan in plants, nor on the incorporation thereof in plant cell walls.

WO2006/136351 showed that the strategy as proposed in WO00/09729 does not lead to the functional incorporation of chitin into the plant cell wall. Instead, WO 2006/136351 discloses that chitin is effectively produced in the secondary cell wall of cotton fibers only when the N-acetylglucosamine transferase is relocated to the Golgi apparatus. For the fungal chitin synthase from *Neurospora crassa*, relocation to the Golgi apparatus is achieved by operable fusion of this fungal chitin synthase with a heterologous signal anchor sequence specific for the Golgi apparatus, and by expressing the resulting chimeric gene in plants. For the NODC type of N-acetylglucosamine transferase however, addition of a signal anchor sequence is not required for localization of the NodC protein to the Golgi apparatus, and for incoporation of chito-oligosaccharides into the plant cell wall without external GlcNAc feeding. Although chitin could be efficiently produced in the plant cell walls, it was also observed that transgenic plants comprising NODC had shorter roots as compared to wild-type plants.

Thus there remains a need for alternative methods to produce plant cell walls such as secondary cell walls which comprise positively charged polysaccharides. In particular a need exists for providing methods to produce plants with positively charged oligosaccharides in their cell walls, but without root growth retardation. These and other problems are solved as described hereinafter in the different embodiments, examples and claims.

SUMMARY OF THE INVENTION

In one embodiment, the invention provides a method for production of a plant cell, or a plant, such as a cotton plant, comprising positively charged oligosaccharides in the cell wall, particularly the secondary cell wall of a plant cell, comprising introducing a chimeric gene into the plant cell, whereby the chimeric gene comprises a plant-expressible promoter operably linked to a DNA region coding for a NODC-type N-acetylglucosamine transferase fused to a Golgi signal anchor sequence; and a transcription termination and polyadenylation region. In another embodiment, a method is provided for production of a plant, such as a cotton plant, comprising positively charged oligosaccharides in the cell using methods according to the invention, characterized in that the root length of said plant is essentially the same as that of a wild-type plant not comprising the NODC gene.

The invention further provides a method to produce plants comprising positively charged oligosaccharides in the cell wall, further comprising the step of deacetylating said oligosaccharides consisting of N-acetylglucosamine monomers by treating the cell wall from said plant with an alkali solution or through the enzymatic action of chitin deacetylases.

The invention also provides chimeric genes comprising a plant-expressible promoter; a DNA region coding for a Nodulation C protein fused to a signal anchor sequence for targeting to the membranes of the Golgi-apparatus; and a transcription termination and polyadenylation region, and plant cells, plants, such as cotton and cotton fibers comprising such a chimeric gene. In another embodiment, the invention provides plants consisting essentially of plant cells comprising a chimeric gene comprising a NODC fused to a Golgi signal anchor sequence, characterised in that the root length of said plant is essentially the same as that of a wild-type plant not comprising NODC.

The invention further provides plant cells, plants, such as cotton plants, cotton fibers and yarns generated from cotton fibers comprising the chimeric gene comprising NODC fused to a Golgi signal anchor sequence.

The invention also provides plant cell walls, comprising an increased amount of oligosaccharides, which can be positively charged oligosaccharides, such as oligo-N acetylglucosamines, with a polymerization degree of 2 to 10, or 2 to 9, or 2 to 8, or 2 to 7, or 2 to 6, or 2 to 5, or 3 to 5. Such plant cell walls are obtainable by the methods of the invention. These plant cell walls may be subjected to further chemical modification.

In a specific embodiment, the invention provides cotton fibers comprising an increased amount of the positively charged oligosaccharides mentioned herein, and yarns, textiles which comprise such cotton fibers. The cotton fibers may be used as such or may have been subjected to further chemical modification, including dying. These cotton fibers can be recognized e.g. through detection of the NODC comprising chimeric genes, through their increased binding of anionic dyes, including congo red, through their increased binding of wheat germ agglutinin or through their increased reactivity with amine-reactive dyes when compared to cotton fibers obtained from cotton plants of a an isogenic line which does not contain a chimeric NODC gene operably linked to a Golgi signal anchor sequence as described herein. The presence and/or the amount of oligosaccharides in the cotton fibers can also be determined directly through e.g. high performance thin layer chromatography (HPTLC) or high-performance liquid chromatography and mass spectrometry (HPLC-MS).

In another embodiment, the invention is directed towards the use of a DNA region coding for an N-acetylglucosamine transferase capable of being targeted to the Golgi apparatus of a plant cell to increase the amount of positively charged oligasacccharides in the cell wall of a plant cell or to increase the reactivity of plant cell walls for chemical modifications of such plant cell walls.

In one embodiment, the invention is directed to a method of dying cotton fibers, yarn or fabric comprising providing the fiber described herein or the yarn or fabric described herein and applying a dye reactive to said fibers, yarn or fabric.

The invention also provides chimeric genes comprising the following operably linked DNA regions: a plant-expressible promoter; a DNA region coding for a NODC-type N-acetylglucosamine transferase fused to a Golgi signal anchor sequence; and a transcription termination and polyadenylation region, and the use of these chimeric genes to increase the amount of positively charged oligosaccharides in the plant cell wall and to produce cotton fibers, yarns and fabrics with improved reactivity, such as dyeability.

BRIEF DESCRIPTION OF THE FIGURES

FIG. 1: Alignment of the amino acid sequence of different NODC proteins. Amino acid residues conserved in all proteins are indicated in bold. ROT_NODC_RHILP: NODC protein from *Rhizobium leguminosarum* (biovar *phaseoli*) (SEQ ID No 7); ROT_NODC_BRAJA: NODC protein from *Bradyrhizobium japonicum* (SEQ ID No 2); ROT_NODC_RHIS3 NODC protein from *Rhizobium* sp. (strain N33) (SEQ ID No 8); ROT_NODC_RHISN: NODC protein from *Rhizobium* sp (SEQ ID No 17); ROT_NODC_RHILV: NODC protein from *Rhizobium leguminosarum* (biovar *viciae*) (SEQ ID No 4) and ROT_NODC_AZOCA: NODC protein from *Azorhizobium caulinodans* (SEQ ID No 1).

FIG. 2: Alignment of the amino acid sequence of different NODC proteins. Amino acid residues conserved in all proteins are indicated in bold. ROT_NODC_BRAJA: NODC protein from *Bradyrhizobium japonicum* (SEQ ID No 2); ROT_NODC_RHIS3 NODC protein from *Rhizobium* sp. (strain N33) (SEQ ID No 8); ROT_NODC_RHISN: NODC protein from *Rhizobium* sp (SEQ ID No 17); ROT_NODC_RHILV: NODC protein from *Rhizobium leguminosarum* (biovar *viciae*) (SEQ ID No 4) and ROT_NODC_AZOCA: NODC protein from *Azorhizobium caulinodans* (SEQ ID No 1).

comparison between wild-type plants and different transgenic lines containing pTJN6. Black bars: wild-type; checked bars: pTJN6-4; hatched bars: TJN6-14; vertically striped bars: pTJN6-23; horizontally striped bars: pTJN6-26.

Figure 4:
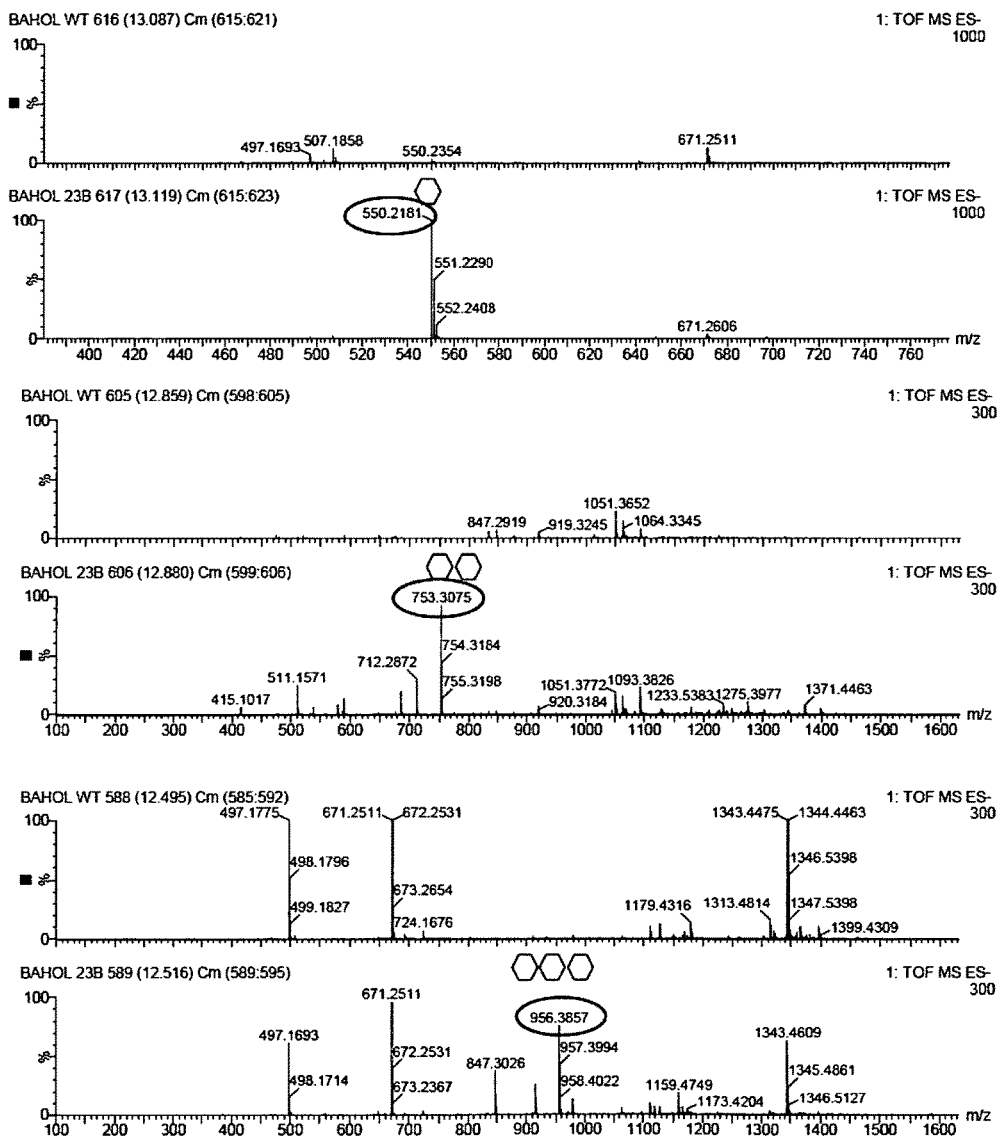

FIG. 4. Presence of mono-, di-, tri-, tetra- and pentamers of GlcNAc in *Arabidopsis* plants transformed with pTJN6. The circled values represent the values for the GlcNAc oligomers; the number of hexagons above these values represents the degree of polymerisation of these oligomers. The graphs are shown in pairs, of which the upper graph is wild-type, and the lower graph is the transformant containing pTJN6.

DETAILED DESCRIPTION OF DIFFERENT EMBODIMENTS OF THE INVENTION

The current invention is based on the finding that, upon expression in plant cells, fusion of a heterologous Golgi signal anchor sequence to a N-acetylglucosamine transferase of the NODC type unexpectedly increased incorporation of specific N-acetylglucosamine oligomers in plant cell walls up to 65-fold when compared to cell walls from plants expressing an N-acetylglucosamine transferase of the NODC type not fused to a Golgi signal anchor sequence. The synthesis of the GlcNAc oligomers did not require the external addition of GlcNAc to the growth medium.

At the same time, whereas expression of NODC in plants negatively affected root length, fusion of the heterologous Golgi signal anchor sequence to NODC restored the root length to wild-type level.

Thus, in a first embodiment of the invention, a method is provided for the production of positively charged oligosaccharides in the plant cell wall, particularly the secondary cell wall, wherein the method comprises the step of introducing a chimeric gene into the plant cell, and the chimeric gene comprising the following operably linked DNA fragments:
  a plant-expressible promoter
  a DNA region coding for an N-acetylglucosamine transferase of the NODC type fused to a signal anchor sequence for targeting to the membranes of the Golgi apparatus; and
  a transcription termination and polyadenylation region.

In another embodiment, a method is provided for the production of a plant comprising positively charged oligosaccharides in the cell wall, particularly the secondary cell wall, wherein the method comprises the steps of
  introducing a chimeric gene into the plant cell, and the chimeric gene comprising the following operably linked DNA fragments:
    a plant-expressible promoter;
    a DNA region coding for an N-acetylglucosamine transferase of the NODC type fused to a signal anchor sequence for targeting to the membranes of the Golgi apparatus; and
    a transcription termination and polyadenylation region;
  regeneration of said plant cell into a plant.

Suitable for the method of the invention is that the Nodulation C protein is expressed in said plant cell. The Nodulation C protein may be expressed in all cells of said plant. Alternatively, the Nodulation C protein may be expressed in specific tissues of said plant only, but not in others, such as roots or cotton leaves.

Nodulation proteins and their encoding genes are involved in the synthesis of the lipochitooligosaccharide signals or acetylated chitooligomers (Nod factors) which lead to the nodule formation typical of the symbiosis between *Rhizobiaceae* and leguminous plants.

The most crucial nod gene products required for the synthesis of these lipo-chito-oligosaccharides are NODA, NODB and NODC. In the absence of other nod gene products they can form a core signal consisting of oligomers of four or five N-acetylglucosamine residues carrying an N-linked acyl group. The function of each of the three proteins in the synthesis of nodulation factors is well known: NODC is an N-acetylglucosaminyl transferase which produces the chito-oligosacharide chain; the N-acetyl group from the non-reducing N-acetylglucosamine residue of the chito-oligosaccharide chain is removed by NODB, which acts as a chitin oligosaccharide deacetylase; NODA is involved in the attachment of the acyl chain to the free amino group generated by the action of NODB. Other Nod factors, encoded by other nod genes, provide for any of the decorating chemical groups discriminating the different nodulation factors. For the purposes of the present invention, only the NODC proteins and encoding genes are of relevance.

Nodulation C protein ("NODC protein") is a well characterized protein (for a review see Kamst and Spaink, 1999, *Trends in Glycoscience and Glycotechnology*, 11, pp 187-199). It belongs to a family of β-polysaccharide synthase proteins that are involved in the synthesis of linear polysaccharides containing β-linked monosaccharide residues. The enzymes that are structurally most closely related to NODC are transferases involved in the synthesis of chitin (β-1-4 linked N-acetylglucosamines); cellulose (the polymer of β-1-4 linked glucose residues); hyaluronic acid (a co-polymer of N-acetylglucosamine and glucuronic acid) and chitin oligosaccharides produced during early development of zebrafish embryos. Six short regions conserved between these proteins can be recognized. For NODC proteins, these short sequences correspond to:
  1) a K residue at position 23 of SEQ ID No 1 (NODC from *Azorhizobium caulinodans*)
  2) the sequence DDG at position 86-88 of SEQ ID No 1
  3) the sequence VDSDT at position 137-141 of SEQ ID No 1
  4) the sequence GPCAMYR at position 207-213 of SEQ ID No 1
  5) the sequence GEDRHL at position 237-242 of SEQ ID No 1; and
  6) the sequence QQLRW at position 274-278 of SEQ ID No 1

However, it is important to realize that some NODC proteins or variants thereof may exist wherein one or more of the above mentioned consensus sequences are not absolutely conserved.

NODC proteins are also frequently characterized by hydrophobic stretches of amino acid residues representing transmembrane domains (Barney et al. 1996, *Molecular Microbiology* 19, pp 443-453). The N-terminal hydrophobic domain spans the bacterial membrane in a $N_{out}$-$C_{in}$ orientation, with the adjacent large hydrophilic domain being exposed to the bacterial cytoplasm. This orientation appears to be dependent upon the presence of the hydrophobic region(s) near the C-terminus, potentially containing three membrane spans, such that the C-terminus of NODC is normally located in the bacterial periplasm.

The large hydrophilic loop of NODC also has other structural similarity to similar regions in the other β-glucosyl transferases. This region has been proposed to be made up of an A domain (which extends from about residue 45 to 140 in the sequence of SEQ ID No 4) consisting of alternating β-sheets and α-helices, and a B-domain (corresponding to residues 215-280 of SEQ ID No 4) thought to be responsible for the processivity of NODC. In the A-domain, two aspartate residues are conserved (residues 88 and 139 of SEQ ID No. 4); in the B-domain one aspartate residue and the motif QXXRW (residue 240 and 276-280 of SEQ ID No 4) are also conserved and thought to be crucial for catalytic activity.

When different NODC proteins are compared among themselves, amino acid sequences which are more conserved are revealed. FIG. 1 represents an alignment of different NODC proteins from SEQ ID No 1, 2, 8, 4, 7, 17 and indicates a number of conserved residues between the different NODC proteins including (in order):

```
the sequence
PXVDVIXPXXNE (SEQ ID No 18)

the sequence
VDDGSXN (SEQ ID No 19)

the sequence
GDXXLDVDSDTXXXXDV (SEQ ID No 20)

the sequence
GXXMGQ (SEQ ID No 21)

the sequence DMEYWLACNEERXXQXRFGXVMXCXGXCXMYR
(SEQ ID No 22)

the sequence
FRTXYXPXAXAXTXVP (SEQ ID No 23)

the sequence
YLXQQLRWARSTXRXTXL (SEQ ID No 24)

the sequence
QNXGXXLL (SEQ ID No 25)

the sequence RFXFXXXHXXXNXXXLXPLKXYALXT
(SEQ ID No 26)
```

FIG. 2 represents an alignment of a subset of different NODC proteins, showing even more conserved residues such as:

```
the sequence
WLTRLIDMEYWLACNEERXXQXRFGXVMCCCGPCAMYRRS
(SEQ ID No 27)

the sequence
LLXXYEXQXFXGXPSXFGEDRHLTILMLXAGFRTXYVPXAXAXTXVP
(SEQ ID No 28)

the sequence
YLRQQLRWARSTXRDTXLA (SEQ ID No 29)
```

The length of the oligosaccharide backbone in lipo-chitin oligosaccharides produced by different *Rhizobiaceae* varies between two and six residues. It has been shown that the nodulation protein NODC is an important determinant of the chitin oligosaccharide chain length in the synthesis of the chito-oligosaccharide chain (Kamst et al., 1997, *Journal of Bacteriology* 179, p 2103-2108).

Coding regions coding for an N-acetylglucosamine transferase of the NODC type may be obtained directly from bacteria belonging to the genera *Rhizobium, Azorhizobium, Bradyrhizobium, Mesorhizobium, Ralstonia, Cupriavidus, Streptomyces, Burkholderia, Sinorhizobium, Desulfobacterium, Dokdonia, Methylobacterium, Phyllobacterium* or *Psychroflexus*. However, it will be immediately clear that such coding regions may also be made synthetically, even with a codon usage adapted to the plant, particularly the fiber producing plant into which the chimeric gene overexpresing the NODC type protein is introduced.

Different sequences for NODC proteins are available from databases such as the protein sequences identified by the following accession numbers: 1615305C, 1615305D, 1615305E, AAA26226, AAA63602, AAB16897, AAB24745, AAB34509, AAB47353, AAB51164, AAB71694, AAB91695, AAB95329, AAC80567, AAD11313, AAD11315, AAD11317, AAD11319, AAD11321, AAD11323, AAD11325, AAD11327, AAD11329, AAD11331, AAD11333, AAD11335, AAD11337, AAD11339, AAD11341, AAD11343, AAD11345, AAD11347, AAD11349, AAD11351, AAD11353, AAD11355, AAD11357, AAD11359, AAD11361, AAD11363, AAD11365, AAD11367, AAD11369, AAD11371, AAD11373, AAD11375, AAD11377, AAD11379, AAD11381, AAD11383, AAD11385, AAD11387, AAD11389, AAD11391, AAD11393, AAD11395, AAD11397, AAD11399, AAD11401, AAD11403, AAD11405, AAG60998, AAK00157, AAK39956, AAK39957, AAK39958, AAK39959, AAK39960, AAK39961, AAK39962, AAK39963, AAK39964, AAK39965, AAK39966, AAK39967, AAK50872, AAK65131, AAL88670, AAN62903, AAS91748, AAU11338, AAU11339, AAU11340, AAU11341, AAU11342, AAU11343, AAU11344, AAU11345, AAU11346, AAU11347, AAU11348, AAU11349, AAU11350, AAU11351, AAU11352, AAU11353, AAU11354, AAU11355, AAU11356, AAU11357, AAU11358, AAU11359, AAU11360, AAU11361, AAU11362, AAU11363, AAU11364, AAU11365, AAX30049, AAX30050, AAY44091, AAY44092, AAY44093, AAY89044, AAZ81541, ABC40958, ABC67303, ABD39006, ABD39007, ABD39008, ABD39009, ABD39010, ABD39011, ABD39012, ABD39013, ABD39014, ABD39015, ABD39016, ABD39017, ABD39018, ABD39019, ABD39020, ABD39021, ABD39022, ABD39023, ABD39024, ABD39025, ABD39026, ABD39027, ABD39028, ABD39029, ABD39030, ABD39031, ABD39032, ABD39033, ABD39034, ABD39035, ABD39036, ABD39037, ABD39038, ABD67413, ABD67416, ABD67419, ABD67422, ABD67425, ABD67428, ABD67431, ABD67434, ABD73319, ABD73320, ABD73321, ABD73322, ABD73323, ABD73324, ABD73325, ABD73326, ABD73327, ABD73328, ABD73329, ABD73330, ABD94161, ABD94162, ABD94163, ABD94164, ABD94165, ABF93198, ABF93199, ABF93200, ABF93201, ABF93202, ABM69186, ABM69187, ABM69188, ABM69189, ABM69190, ABN09217, ABN09218, ABN09219, ABN11177, ABN11178, ABN11179, ABP93834, ABS85176, ABS85177, ABS85178, ABS85179, ABS85180, ABS85181, ABS85182, ABU69044, ABU69045, ABU69046, ABU69047, ABU69048, ABU69049, ABU69050, ABU69051, ABU69052, ABU69053, ABU69054, ABU69055, ABU69056, ABU69057, ABU69058, ABU69059, ABU69060, ABU69061, ABU89879, ABV25689, ABV25690, ABV25691, ABV25692, ABV25693, ABV25694, ABW96196, ABW96197, ABW96198, ABW96199, ABW96200, ABW96201, ABW96202, ABW96203, ABW96204, ABW96205, ABW96206, ABW96207, ABW96208, ABW96209, ABW96210, ABW96211, ABY59633, ABY59634, ABY59635, ABY59636, ABY59637, ACA80309, ACA80310, ACA80311, ACA80312, ACA80313, ACC77565, ACD39337, ACD39338, ACD39339, ACD39340, ACD39341, ACD39342, ACD39343, ACD39344, ACD39345, ACD39346, ACD39347, ACD62595, ACD63093, ACD63094, ACD63095, ACD63096, ACD63097, ACD63098, ACD63099, ACD63100, ACD63101, ACD63102, ACD63103, ACD63104, ACF19762, ACF19763, ACF19764, ACF19765, ACF19766, ACF19767, ACF19768, ACF19769, ACF19770, ACH91221, ACH91222, ACH91223, ACH91224, ACH91225, ACH91226, ACH91227, ACH91228, ACH91229, ACH91230, ACH91231, ACH91232, ACH91233, ACH91242, ACH91243, ACH91244, ACH91245, ACH91246, ACH91247, ACH91248, ACH91249, ACI47333, ACI47334, ACI47335, ACI47336, ACI47337, ACI47338, ACI47339, ACI47340, ACI47341, ACI47342, ACI47343, ACI47344, ACI47345, ACL12058, ACL12059, ACL50517, ACL50518, ACL50519, ACL50520, ACL50521, ACL50522, ACL50523, ACM69382, ACM79634, ACM79635, ACM79636, ACM79637, ACM79638, ACM79639, ACM79640, ACM79641, ACM79642, ACM79643, ACM79644, ACM79645, ACM79646, ACN17701, ACN69201, ACN69202, ACN69203, ACN69204, ACN69205, ACN69206, ACN69207, ACN69208, ACN69209, ACN69210, ACN69211, ACN69212, ACN69213, ACO58664, ACO58665, ACO58666, ACO58667, ACO58668, ACO58669, ACO58670, ACO58671, ACO58672, ACO58673, ACO58674, ACO58675, ACP40990, ACS35430, ACS35434, ACT34091, ACT34094, ACT34097, ACT34100, ACT34101, ACT34104, ACT34107, ACT34110, ACT34113, ACT34116, ACT34119, ACT34122, ACT34125, ACT34128, ACT34131, ACT34134, ACT34137, ACT34140, ACT34143, ACV52950, ACV52951, ACV52952, ACV52953, ACV52954, ACV52955, ACX47326, ACX47327, ACX47328, ACX47329, ACX47330, ACX47331, ACX47332, ACX47333, ACX47334, ACY02884, ACY78518, ACZ52692, ACZ52693, ACZ52694, ACZ52695, ACZ52696, ACZ52697, ADD20957, ADD20958, ADD20959, ADD20960, ADD20961, ADD20962, ADD20963, ADD20964, ADD20965, ADD20966, ADD20967, ADD20968, ADD20969, ADD20970, ADD20971, ADG63645, ADG63646, ADG63647, ADG63648, ADG63649, ADG63650, ADG63651, ADG63652, ADJ18191, ADJ18192, BAA06082, BAA06083, BAA06084, BAA06085, BAA06086, BAA06087, BAA06088, BAA06089, BAA06090, BAA24092, BAB52500, C26813, CAA25810, CAA25811, CAA25814, CAA26310, CAA26311, CAA51773, CAA51774, CAA608779, CAA67139, CAB56055, CAC42489, CAD29949, CAD29950, CAD29951, CAD29952, CAD29953, CAD29954, CAD29955, CAD29956, CAD29957, CAD31533, CAD43933, CAD90257, CAD90583, CAD90584, CAD90585, CAD90586, CAD90587, CAD90588, CAH04369, CAN84684, CAP64017, EAQ38847, EAS72439, NP_106714, NP_435719, NP_443883, P04340, P04341, P04677, P04678, P04679, P06234, P06235, P17862, P24151, P26024, P50357, P53417, P72334, Q07755, Q53513, YP_001796208, YP_002605865, ZP_01050448 or ZP_01252570 (incorporated herein by reference).

Other entries in the UNIPROT databases referring to full length NODC proteins are summarized in the table below. All mentioned amino acid sequences referenced by the accession number are herein incorporated by reference.

TABLE full length NODC proteins

| UniProt/UniParc ID | UniProt Accessions | Species Name | Length |
|---|---|---|---|
| NODC_BRAJA | P26024 | *Bradyrhizobium japonicum* | 485 |
| NODC_AZOCA | Q07755 | *Azorhizobium caulinodans* | 395 |
| Q6PTX8_9RHIZ | Q6PTX8 | *Rhizobium* sp. SIN-1 | 408 |
| Q70YC2_9BURK | Q70YC2 | *Cupriavidus taiwanensis* | 450 |
| Q6EX51_SINSB | Q6EX51 | *Sinorhizobium* sp. | 452 |
| NODC_RHIS3 | P72334 | *Rhizobium* sp. | 450 |
| NODC_RHILP | P24151 | *Rhizobium leguminosarum* | 428 |
| Q8GNH5_RHIME | Q8GNH5 | *Rhizobium meliloti* | 421 |
| Q53254_RHITR | Q53254 | *Rhizobium tropici* | 452 |
| Q9AQ23_BRASW | Q9AQ23 | *Bradyrhizobium* sp. | 452 |
| NODC_RHISN | P50357 | *Rhizobium* sp. | 413 |
| Q8KLG3_RHIET | Q8KLG3 | *Rhizobium etli* | 443 |
| Q9RAN5_MESS7 | Q9RAN5 | *Mesorhizobium* sp. | 416 |
| Q9Z3I6_BRASS | Q9Z3I6 | *Bradyrhizobium* sp. | 481 |
| NODC_RHILO | P17862 | *Rhizobium loti* | 424 |
| Q8KJI5_RHILO | Q8KJI5 | *Rhizobium loti* | 424 |
| NODC_RHIGA | P50356 | *Rhizobium galegae* | 433 |
| NODC_RHIME | P04341 | *Rhizobium meliloti* | 426 |
| Q9R614_RHIME | Q9R614 | *Rhizobium meliloti* | 424 |
| O52478_RHIME | O52478 | *Rhizobium meliloti* | 402 |
| Q52971_RHIME | Q52971 | *Rhizobium meliloti* | 402 |
| NODC_RHILV | P04340 | *Rhizobium leguminosarum* | 424 |

However, it will be clear that variants of NODC proteins, wherein one or more amino acid residues have been deleted, substituted or inserted, which can be deduced from the above mentioned amino acid sequences, can also be used to the same effect in the methods according to the invention, provided that the enzymatic activity has not changed. These variant NODC proteins may have about 95% sequence identity to any one of the herein mentioned NODC proteins. A method for determining enzymatic activity of NODC proteins in vitro has been described e.g. by Kamst et al., 1997 Journal of Bacteriology, 179, p 2103-2108.

Thus, as used herein, an "N-acetylglucosamine transferase that is of the NODC type" is an N-acetylglucosamine transferase that catalyzes the transfer of the GlcNAc moiety from UDP-GlcNAc to a nascent chitin oligosaccharide. Preferably the protein contains the conserved regions which can be found by comparing the different NODC proteins.

Suitable for the methods of the invention are the proteins listed in SEQ ID No 1 to SEQ ID No 9, particularly the protein listed in SEQ ID No 1, and the DNA fragments encoding such a protein.

NODC should be equipped with heterologous signal anchor sequences targeting the NODC to the membranes of the Golgi apparatus. Such sequences are known in the art, including the sequences within and adjacent to the transmembrane segment of α-2,6-sialyltransferase (particularly the first 44 or 52 amino acids thereof; Munro et al. 1991, EMBO Journal, 10: 3577-3588); the signal anchor sequence from human galactosyl transferase (particularly the first 60 amino acids thereof) or the signal anchor sequence from the *Arabidopsis* homologue of the yeast HDEL receptor (AtERD2) (Saint-Jore et al., 2002, The Plant Journal, 29: 661-678), the signal anchor sequence from β1,2-xylosyltransferase protein (particularly the first 36 amino acids thereof; Pagny et al., 2003, The Plant Journal 33: 189-203), the signal anchor sequences of N-acetyl-glucosaminyl transferase I (particularly the first 77 amino acids thereof; Essl et al. 1999, FEBS Lett. 453:169-173) or a 20 amino acid fragment of the human lysosomal protein LAMP1 (Brandizzi et al., 2002, Plant Cell 14: 1077-1092) (all publication incorporated herein by reference). Other Golgi targeting signals to be employed by fusion at the C-terminus of the N-acetylglucosamine transferase include the amino acid sequence "YYHDL" (SEQ ID No 30) as can be found in *Arabidopsis* DAGAT1 protein or "LKLEI" (SEQ ID No 31) as can be found in *Arabidopsis* DAGAT2. Fusion of such Golgi signal anchor sequences to NODC by linking DNA fragments encoding the respective polypeptides can be achieved using standard recombinant DNA techniques.

A heterologous signal anchor sequence as used herein means a signal anchor sequence that is not naturally part of the protein to which it is fused. The heterologous signal anchor sequence can thus be derived from another protein from the same species, or can be derived from a protein from another species.

The chimeric genes according to the invention comprise a plant-expressible promoter. As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, T-DNA gene promoters such as Pmas, Pnos, Ptr1, Ptr2, Cassava vein mosaic virus and the like.

A transcription termination and polyadenylation region as used herein is a sequence that drives the cleavage of the nascent RNA, whereafter a poly(A) tail is added at the resulting RNA 3' end. Transcription termination and polyadenylation signals functional in plants include, but are not limited to, 3'nos, 3'35S, 3'his and 3'g7.

A plant-expressible promoter that controls initiation and maintenance of transcription preferentially in fiber cells is a promoter that drives transcription of the operably linked DNA region to a higher level in fiber cells and the underlying epidermis cells than in other cells or tissues of the plant. Such promoters include the promoter from cotton from a fiber-specific β-tubulin gene (as described in WO0210377), the promoter from cotton from a fiber-specific actin gene (as described in WO0210413), the promoter from a fiber specific lipid transfer protein gene from cotton (as described in U.S. Pat. No. 5,792,933), the promoter from the seed coat and fiber-specific protease from cotton (Hou et al., 2008, *Chinese Science Bulletin* 53, pp 2639-2645), the promoter from fiber-specific R2R3 MYB gene from cotton (Pu et al., 2008, *Genetics* 180, pp 811-820), a promoter from an expansin gene from cotton (WO9830698), a promoter from a chitinase gene in cotton (US2003106097), the promoter of CesA1 (U.S. Pat. No. 6,271,443), or the promoters of the fiber specific genes described in U.S. Pat. No. 6,259,003 or U.S. Pat. No. 6,166,294 or WO96040924.

Positively charged oligosaccharides according to the invention can consist of N-acetylglucosamine oligomers such as β1-4 linked N-acetylglucosamine oligomers. Said oligosaccharides can comprise 2 to 10, or 2 to 9, or 2 to 8, or 2 to 7, or 2 to 6, or 2 to 5, or 3 to 5 N-acetylglucosamine monomers.

Degree of polymerisation as used herein is the number of monomers present in an oligomer or in a polymer. The degree of polymerisation of an N-acetylglucosamine oligomer is the number of N-acetylglucosamine monomers present in said oligomer.

In another embodiment, the invention provides a method to produce plants comprising positively charged oligosaccharides in the cell wall using methods according to the invention, characterized in that said plants have a root length which is essentially the same as that of plants not comprising a NODC gene.

The root length is essentially the same when it has a length of at least 70%, or 80% or 90%, or 95%, or between 70% and 120%, or between 80% and 120%, or between 80% and 110%, or between 90% and 110%, or between 95% and 110% of, or which is identical to the length of the wild-type root not comprising a NODC gene.

In a further embodiment, the plants according to the invention are selected from cotton, hemp or flax. In a further embodiment, said plants are cotton plants comprising fibers.

The invention further provides plant cell walls, such as secondary cell walls or fibers including such cell walls obtained from plant cells using the methods according to the invention. Such plant cell walls comprise positively charged oligosaccharides, such as N-acetylglucosamine oligomers, β1-4 linked N-acetylglucosamines, or chitin, embedded into the cellulose.

The invention also provides the step of isolating plant cell walls and fibers from the plants obtained by the method of the invention.

The positively charged polysaccharides according to the invention may be further modified, e.g. partly or completely deacetylated such that oligomers comprising glucosamine residues are obtained. The amino-group of the resulting glucosamines is chemically more reactive than the amino-acetyl group of N-acetylglucosamine or the hydroxyl group of cellulose.

Deacetylation of N-acetylglucosamine can be performed chemically using methods including alkali hydrolysis, through application of thermo-mechano-chemical technology (Pelletier et al, 1990, Biotechnol Bioeng. 36, pp 310-315), using alkali impregnation technique (Rao et al, 1987, Indian Journal of Technology, 25, pp 194-196), using water-miscible organic solvents as diluents (Batista and Roberts, 1990, Makromolekulare Chemie-Macromolecular Chemistry and Physics, 191, pp 429-434.), using thiophenol to trap oxygen during deacetylation processes (Domard and Rinaudo, 1983, International Journal of Biological Macromolecules, 5, pp 49-52.), or using autoclaving conditions (No et al., 2000, Journal of Agricultural and Food Chemistry, 48, pp 2625-2627). Deacetylation of chitin can also be performed enzymatically using chitin deacetylases. Such chitin deacetylases include those from *Mucor rouxii, Absidia coerulea, Aspergillus nidulans, Colletotrichum lindemuthianum* and *Saccharomyces cerevisiae*.

The plant cell wall obtained according to the invention, particularly those which have been subjected to a deacetylation step, can be further chemically modified. Products containing such plant cell walls, such as fibers, yarns or fabrics have qualities resembling those of the cellulose-chitosan blends described in the art, including improved dyeability, improved inhibition of e.g. dermatophytes, controlled drug release etc.

The invention also provides the chimeric genes as herein described, and plant cells or plants containing such chimeric genes, and the use of said chimeric genes to increase the amount of positively charged oligosaccharides in the cell wall, or to increase the reactivity of plant cell walls, cotton fibers or yarns or fabrics for chemical modifications such as dyeability. The invention further provides plants, such as cotton plants, containing such chimeric genes characterized in that the root length of said plant is essentially the same as that of isogenic plants not containing such chimeric genes. The invention further provides the fibers from such cotton plant, and a yarn or fabric made from said fibers.

An increase in the efficiency of production of N-acetylglucosamine oligomers, or an increase in the amount of positively charged oligosaccharides in plant cell walls as used herein means an increase of positively charged oligosaccharides or N-acetylglucosamine oligomers in the plant cell walls which is at least 2-fold, or at least 5-fold, or at least 10-fold, or at least 20-fold, or 2 to 100-fold, or 5 to 100-fold, or 10 to 100-fold or 20 to 100-fold.

In a specific embodiment, the invention provides cotton fibers obtained from or which can be obtained from cotton plants according to the methods of the invention, or comprising the chimeric gene according to the invention. In other words, cotton fibers are provided from cotton plants comprising in the genome, such as the nuclear genome, of their cells a chimeric gene comprising a plant-expressible promoter operably linked to a DNA region coding for a NODC-type N-acetylglucosamine transferase fused to a Golgi signal anchor sequence. Particular embodiments of DNA coding regions or promoters comprised in the chimeric genes transferred into cotton plants are as described elsewhere in this document.

The cotton fibers according to the invention can be distinguished from naturally occurring cotton fibers, i.e. cotton fibers obtained from an isogenic line which does not comprise a chimeric gene according to the invention, by the capacity of such fibers for increased staining with anionic dyes (including e.g. Congo Red), by the capacity of such fibers for increased staining with amine-reactive dyes (including e.g. tetrafluorophenyl ester). The cotton fibers according to the invention also have the capacity of binding of Wheat germ agglutinin which binds chito-oligomers. The cotton fibers according to the invention can also be distinguished from naturally occurring cotton fibers by direct detection of the N-acetylglucosamine and GlcNAc oligmers, such as chitobiose, chitotriose or chitotetraose, preferably after treatment of the fiber cell wall material with cellulase. The cotton fibers according to the invention may also be distinguished by their increased nitrogen content.

Cotton fibers according to the invention can also be distinguished from the chitosan coated fibers or from chitosan/cellulose blended yarns, in that the positively charged oligomers are more or less evenly distributed in the secondary plant cell walls making up the fibers. Accordingly, in microscopical sections of cotton fibers, stained e.g. with WGA or with congo red or with tetrafluorophenyl as described hereinafter, the dyes will be distributed more or less evenly throughout the cell walls making up the cotton fibers, whereas in chitosan-coated fibers, the staining will be concentrated at the coat of chitosan located as a sheet at the surface of the treated fibers.

Cotton fibers according to the invention can also be distinguished from other cotton fibers by detection of the NODC comprising chimeric genes in nucleic acids which remain in the plant material associated with cotton fibers.

The increased staining of the plant cell wall material according to the invention, by anionic dyes such as congo-red can be quantified e.g. by dying a uniform amount of material under standard conditions, spreading out the material over a standardized area (such as a well in a multiwell plate) digitalizing a picture of the area for the gray scale of the colored layer of material. The less gray, the more stained the plant cell wall material is. In this way, fibers and cell wall material according to the invention may be obtained with an increase of at least 10%, or at least 30%, or at least 50% in staining by congo-red compared to control cell wall material or fibers from isogenic plant lines without a NODC encoding gene.

The plant cell wall material according to the invention can also be stained with acid dyes such as Acid Orange 7. Fibers and cell wall material according to the invention may be obtained with an increase of at least 50%, or at least 70%, or between 50% and 100% in staining by Acid Orange 7 as compared to control cell wall material or fibers from isogenic plant lines without a NODC encoding gene.

The capacity of the novel cotton fibers to specifically bind wheat germ agglutin (detectable by the coupled fluorophoric group) is a clear distinguishing feature of the provided novel cotton fibers over the naturally occurring cotton fibers. Except for a very low background fluorescence, naturally occurring cotton fibers do not stain/fluoresce when treated with WGA-alexa fluor 488 or 555. The fluorescence of cotton fibers increases at least 5 times when chito-oligomers are present. Accordingly, the invention provides cotton fibers which are capable of specifically binding wheat germ agglutinin, or WGA coupled to a flurophore, such as WGA Alexa 488 or WGA Alexa 555 or which, when treated with WGA Alexa 488 or WGA Alexa 555 provide a bright fluorescence under UV light. This fluorescence is not restricted to the surface of the cotton fiber but is distributed throughout the cell wall of the fiber cells.

Plant cell wall material according to the invention, including cotton fibers typically possess chito-oligosaccharides in a concentration of at least 0.1 µg/mg cell wall material, or at least 1 µg/mg cell wall material, or at least 5 µg/mg cell wall material.

Wherever the methods of the invention are directed to introduction of a chimeric gene in a plant cell, it will be clear that such methods can also be applied in cases whereby the plant cell is incorporated into a mature plant. E.g. transgenic cells may be regenerated into transgenic plants according to established methods.

Methods to transform plants cells and plants are well known in the art. Methods to transform cotton plants are also well known in the art. *Agrobacterium*-mediated transformation of cotton has been described e.g. in U.S. Pat. No. 5,004,863 or in U.S. Pat. No. 6,483,013 and cotton transformation by particle bombardment is reported e.g. in WO 92/15675.

The chimeric genes may be introduced by transformation in cotton plants from which embryogenic callus can be derived, such as Coker 312, Coker310, Coker 5Acala SJ-5, GSC25110, FiberMax 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA, Fibermax® FM5013, FM5015, FM5017, FM989, FM832, FM966 and FM958, FM989, FM958, FM832, FM991, FM819, FM800, FM960, FM966, FM981, FM5035, FM5044, FM5045, FM5013, FM5015, FM5017 or FM5024 and plants with genotypes derived thereof.

"Cotton" as used herein includes *Gossypium hirsutum*, *Gossypium barbadense*, *Gossypium arboreum* and *Gossypium herbaceum* or progeny from crosses between such species.

The methods and means of the current invention may also be employed for other plant species such as hemp, jute, flax and woody plants, including but not limited to *Pinus* spp., *Populus* spp., *Picea* spp., *Eucalyptus* spp. etc.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

Reactive dyes which can be used in connection with the method of dying cotton fibers, yarn or fabric comprise Reactive Red 120 (RR120), Reactive Yellow 176 (RY176), Levafix Blue CA, Reactive Orange 35, Reactive Black 5, Reactive Red 116. Dyeing can also be done with Acid dyes, such as Acid Orange 7, Acid Blue 62, Acid Blue 281, Acid Red 361, Acid Blue 277, Acid Red 4, Acid Blue 113, Acid Yellow 137, Acid Blue 127:1, and Acid Blue 193. These dyes are applied according to protocols well-known in the art.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The transgenic plant cells and plants obtained by the methods disclosed herein may also be further used in subsequent transformation procedures, e.g. to introduce a further chimeric gene.

The cotton plants or seed comprising the chimeric gene disclosed herein or obtained by the methods disclosed herein may further be treated with cotton herbicides such as Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; cotton insecticides such as Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl) methyl](2,2-difluorethyl)amino]furan-2(5H)-on, Thiodicarb, Avermectin, Flonicamid, Pyridalyl, Spiromesifen, Sulfoxaflor; and cotton fungicides such as Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin. For a treatment with cotton herbicides, said cotton plants or seed preferably further comprise a trait conferring a respective herbicide tolerance or are naturally tolerant to said herbicide.

The following non-limiting Examples describe the methods for altering plant cell walls. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:

SEQ ID No 1: Nodulation protein C of *Azorhizobium caulinodans*

SEQ ID No 2: Nodulation protein C of *Bradyrhizobium japonicum*

SEQ ID No 3: Nodulation protein C of *Rhizobium galegae*

SEQ ID No 4: Nodulation protein C of *Rhizobium leguminosarum* (biovar *viciae*)

SEQ ID No 5: Nodulation protein C of *Rhizobium meliloti*

SEQ ID No 6: Nodulation protein C of *Rhizobium tropici*

SEQ ID No 7: Nodulation protein C of *Rhizobium leguminosarum* (biovar *phaseoli*)

SEQ ID No 8: Nodulation protein C of *Rhizobium* sp. Strain N33

SEQ ID No 9: Nodulation protein C of *Rhizobium loti*

SEQ ID No 10: T-DNA of pTJN6

SEQ ID No 11: Amino acid sequence of NODC linked to Golgi-signal anchor sequence.

SEQ ID No 12: nucleic acid sequence of a TDNA comprising a chimeric gene comprising the F286 fiber-selective promoter operably linked to a NODC encoding nucleic acid additionally comprising a Golgi-targeting sequence (=pTDBI146)

SEQ ID No 13: nucleic acid sequence of a TDNA comprising a chimeric gene comprising the Gluc1A promoter operably linked to a NODC encoding nucleic acid additionally comprising a Golgi-targeting sequence (=pTDBI158)

SEQ ID No 14: nucleic acid sequence of a TDNA comprising a chimeric gene comprising the Gluc1D promoter operably linked to a NODC encoding nucleic acid additionally comprising a Golgi-targeting sequence (=pTDBI159)

SEQ ID No 15: nucleic acid sequence of a TDNA comprising a chimeric gene comprising the expansin promoter operably linked to a NODC encoding nucleic acid additionally comprising a Golgi-targeting sequence (=pTDBI165)

SEQ ID No 16: nucleic acid sequence of a TDNA comprising a chimeric gene comprising the E6 promoter operably linked to a NODC encoding nucleic acid additionally comprising a Golgi-targeting sequence (=pTGK96)

EXAMPLES

Example 1: Construction of Chimeric Plant-Expressible Genes Encoding a N-Acetylglucosamine Transferase Protein Fused to a Golgi Signal Anchor Sequence Using standard recombinant DNA techniques, a plant expressible NODC chimeric gene was constructed containing the following operably linked DNA fragments:

- a 35S promoter region from CaMV
- a DNA fragment coding for an untranslated leader sequence (5'Cab22L)
- a DNA fragment coding for the 35 N-terminal amino acids of β-1,2-xylosyltransferase from *Arabidopsis thaliana*
- a DNA fragment coding for NODC of *Azorhizobium caulinodans* cloned in frame with the previous DNA fragment
- a transcription termination and polyadenylation signal from the 35S transcript of CaMV (3' 35S)

The chimeric gene was introduced between T-DNA borders of a T-DNA vector together with a chimeric bar gene providing resistance to phosphinotricin. The resulting T-DNA vector was named pTJN 6. The sequence of the T-DNA of this vector is provided in SEQ ID No 10.

The T-DNA vector pTJN6 was introduced into the *Agrobacterium* strain C58C1RIF(pEHA101) (Hood et al (1986) J. Bact. 168: 1291) which was used to transform *Arabidopsis thaliana* by means of the floral dip method (Clough S J and Bent A F (1998) Plant J. 16: 735-743).

Example 2: Analysis of Root Length of Transgenic *Arabidopsis* Plants

Figure 3:
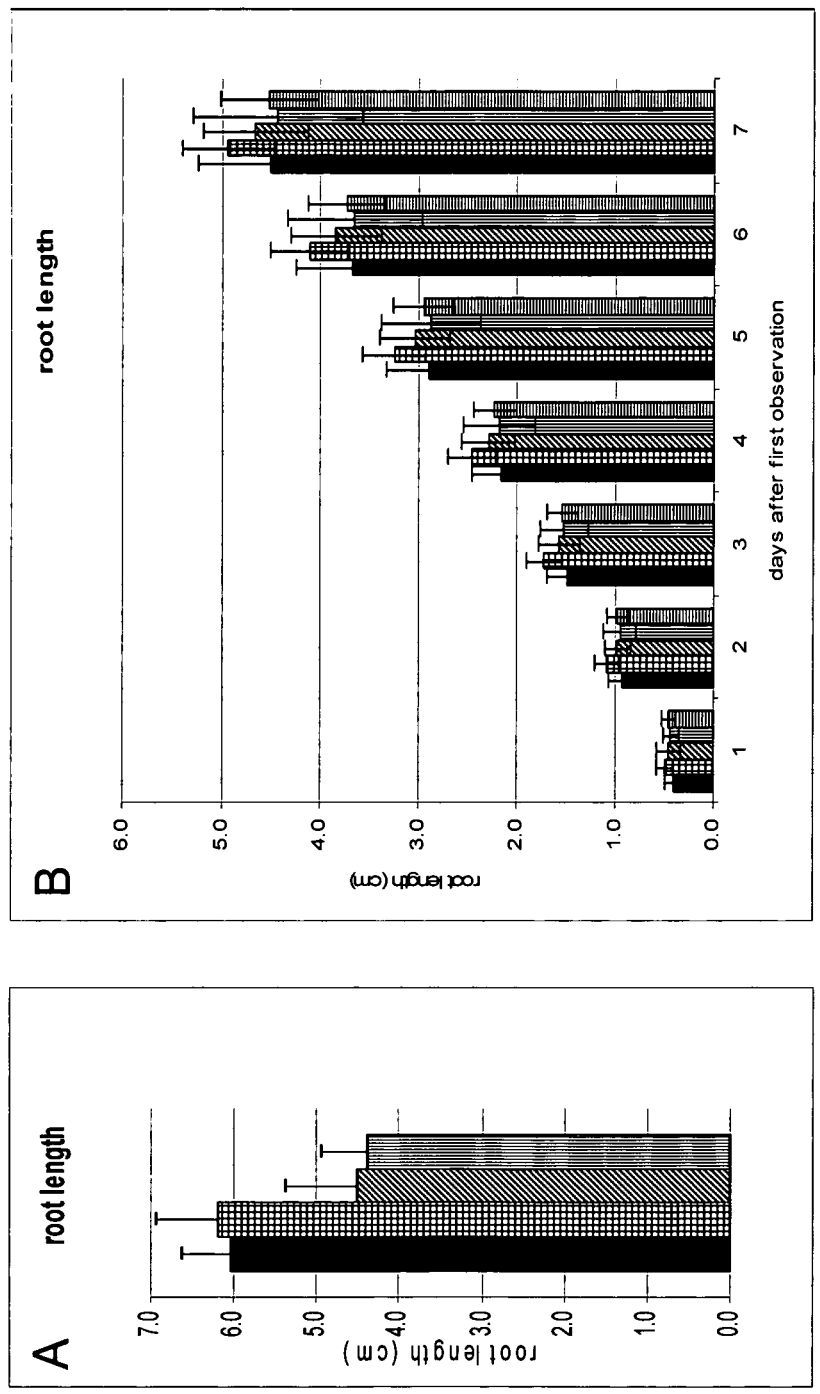
FIG. 3: Root length of wild-type (col) and transgenic *Arabidopsis* plants transformed with pJN6 and pTGK42. A: comparison between wild-type plants and plants transformed with pTJN6 and with two lines containing pTGK42. Black bars: wild-type; checked bars: pTJN6-23; hatched bars: pTGK42-10; vertically striped bars: pTGK42-28. B.

Wild-type *Arabidopsis* and transgenic *Arabidopsis* plants transformed with pTJN6 (NODC with heterologous Golgi signal anchor sequence) and pTGK42 (NODC without heterologous Golgi signal anchor sequence; see WO2006/136351) were gas sterilized and plated on 0.5× Murashige and Skoog (MS) basal salt medium including modified vitamins (Sigma) and 20 g/l glucose. After imbibing for 2 days at 4° C., plates were placed vertically in a growth chamber with a day/night regime of 16 h of light at 21° C. for a period of 9 days. Plates were scanned on a bench-top scanner and measurements were done in ImageJ. Data were exported to Microsoft Excel for analysis. The root length was measured and compared to that of wild-type plants. FIG. 3A shows that, whereas the root length of plants transformed with pTGK42 is about 25% shorter than that of wild-type, there is no significant difference in root length between wild-type and transgenic plants comprising pTJN6.

Figure B shows that, for different transgenic lines comprising pTJN6, there is no significant difference in root length between wild-type and transgenic plants.

Example 3: Characterization of GlcNAc Oligomers in Cell Walls of Transgenic *Arabidopsis* Plants The GlcNAc oligomers in transgenic *Arabidopsis* plants transformed with pTJN6 were analyzed using a combination of derivatization, high-performance liquid chromatography and mass spectrometry as described in Rozaklis et al. (2002, Clinical Chemistry 48:131-139). Briefly, leaf samples (20-150 mg) were snap frozen in liquid nitrogen and grinded in 2 ml eppendorf tubes using a rich mill grinder. 0.5 ml 80% MeOH was added and the tubes were vortexed and centrifuged in a precooled table top centrifuge (5 min 14000 rpm). Supernatant was transferred to a fresh 2 ml tube and freeze dried in a speed vac. The pellet was resuspended in 100 µl MeOH containing 0.5M PMP and 100 µl 800 mM NH3. The reaction mixture was incubated at 70° C. in a thermomixer (Eppendorf) for 9 min at 850 rpm. After this incubation step, the reaction mixture was neutralized by adding 200 µl 800 mM formic acid and further made up to 500 µl with water. After 3 subsequent chloroform extractions using 0.5 ml chloroform, samples were freeze dried and resuspended in 200 ul water. Samples were analyzed on an Acquity UPLC BEH C18 column (Waters Corp., Milford, Mass., USA) (1.7 µm, 150 mm×2.1 mm) using a Finnigan Mat LCQ Mass Spectrometer. Mobile phases were composed of (A) water containing 1% ACN and 0.1% ammonium acetate and (B) ACN containing 1% water and 0.1% ammonium acetate. Column temperature was maintained at 55° C. and the autosampler temperature at 10° C. A flow rate of 300 µl/min was applied during the gradient elution initializing. Conditions where as follows: at time 0 min 20% (B), time 10 min 25% (B) and time 14 min 100% (B). Full MS and MS/MS spectra of the eluting compounds were obtained with electrospray ionization (ESI) operated in positive mode. Derivatized GlcNAC has a m/z value of 552 in positive mode, and the total peak area was considered the best approach for quantification. GlcNAC-oligmers were detected by MS/MS where only specific compounds with specific m/z value were selected for further fragmentation. The 552-peak or 755-peak, corresponding to the derivatized monomer or dimer respectively, were used for quantification. These levels were compared to those of *Arabidopsis* plants transformed with pTGK42 (WO2006/136351) and wild-type *Arabidopsis* plants.

Table 1 shows that, in the presence of the Golgi signal anchor sequence, the amount of GlcNAc2 was up to 65-fold higher, and that of GlcNAc3 was up to 35-fold higher than in the absence of the Golgi signal anchor sequence.

TABLE 1

Relative amounts of the N-acetylglucosamine oligomers GlcNAc2 and GlcNAc3 in leaves of *Arabidopsis* plants transformed with pTJN6 (NODC with heterologous Golgi signal anchor sequence) and with pTGK42 (NODC without heterologous Golgi signal anchor sequence; see WO2006/136351).

| | GlcNAc2 | | GlcNAc3 | |
| --- | --- | --- | --- | --- |
| Construct | area 552 peak | average | area 552 peak | average |
| WT | 3.78E+04 | 5.41E+04 ± 2.31E+04 | — | — |
| WT | 7.04E+04 | | — | |
| pTGK4210 | 3.07E+06 | 2.39E+06 ± 0.97E+06 | 9.22E+05 | 6.70E+05 ± 3.56E+05 |
| pTGK4210 | 1.70E+06 | | 4.18E+05 | |

TABLE 1-continued

Relative amounts of the N-acetylglucosamine oligomers GlcNAc2 and GlcNAc3 in leaves of *Arabidopsis* plants transformed with pTJN6 (NODC with heterologous Golgi signal anchor sequence) and with pTGK42 (NODC without heterologous Golgi signal anchor sequence; see WO2006/136351).

| | GlcNAc2 | | GlcNAc3 | |
|---|---|---|---|---|
| Construct | area 552 peak | average | area 552 peak | average |
| pTGK4228 | 2.83E+06 | 1.82E+06 ± 1.44E+06 | 1.04E+06 | 6.16E+05 ± 6.00E+05 |
| pTGK4228 | 8.00E+05 | | 1.91E+05 | |
| pTJN6-4 | 5.20E+04 | 3.28E+05 ± 3.90E+05 | 1.51E+04 | 5.13E+04 ± 5.12E+04 |
| pTJN6-4 | 6.04E+05 | | 8.75E+04 | |
| pTJN6-14 | 1.67E+05 | 1.42E+05 ± 0.35E+05 | 2.99E+04 | 2.64E+04 ± 0.50E+04 |
| pTJN6-14 | 1.17E+05 | | 2.28E+04 | |
| pTJN6-23 | 1.23E+08 | 1.36E+08 ± 0.18E+08 | 2.17E+07 | 2.24E+07 ± 0.09E+07 |
| pTJN6-23 | 1.49E+08 | | 2.30E+07 | |
| pTJN6-26 | 1.35E+05 | 1.18E+05 ± 0.25E+05 | — | — |
| pTJN6-26 | 1.00E+05 | | — | |
| WT | 1.77E+05 | 1.77E+05 | — | — |
| pTGK4210 | 4.57E+06 | 4.57E+06 | 8.78E+05 | 8.78E+05 |
| pTJN6-23 (1) | 1.43E+07 | 3.00E+07 ± 0.81E+07 | 3.63E+06 | 8.15E+06 ± 6.39E+06 |
| pTJN6-23 (1) | 4.57E+07 | | 1.27E+07 | |
| pTJN6-23 (2) | 5.39E+07 | 4.87E+07 ± 0.74E+07 | 1.40E+07 | 1.30E+07 ± 0.14E+07 |
| pTJN6-23 (2) | 4.35E+07 | | 1.21E+07 | |

As the roots of the plants containing NODC Golgi signal anchor sequence have the same length as those of wild-type plants, whereas those of plants containing NODC without Golgi signal anchor sequence were significantly shorter than wild-type, it was investigated whether oligomers of GlcNAc2 and GlcNAc3 were present in roots of *Arabidopsis* plants comprising NODC without Golgi signal anchor sequence (pTGK42) and with Golgi signal anchor sequence (pTJN6) using methods as described above for the leaves.

Table 2 shows that the roots from the pTJN6 plants contain GlcNAc2 and GlcNAc3 oligonucleotides at levels that are higher than in roots from the pTGK42 plants. The levels of GlcNAc2 and GlcNAc3 in roots are significantly higher than in leaves. The presence of GlcNAc oligos in roots of wild-type plants is presumably due to contamination with root material from the pTGK42 plants and pTJN6 plants.

These results show that the restoration of root length to wild-type levels by adding the Golgi signal anchor sequence to NODC is not due to lack of accumulation of GlcNAc oligos in roots.

TABLE 2

| | Roots | | Leaves | |
|---|---|---|---|---|
| Construct | area 552 peak | average | area 552 peak | average | a. Relative amounts of the N-acetylglucosamine oligomer GlcNAc2 in roots and leaves of *Arabidopsis* plants transformed with pTJN6 (NODC with heterologous Golgi signal anchor sequence) and with pTGK42 (NODC without heterologous Golgi signal anchor sequence; see WO2006/136351) expressed per mg of tissue.

| WT | 1.72E+06 | 1.48E+06 ± 0.31E+06 | 7.53E+04 | 8.41E+04 ± 2.63E+04 |
| WT | 1.58E+06 | | 5.26E+04 | |
| WT | 1.12E+06 | | 9.40E+04 | |
| WT | — | | 1.14E+05 | |
| pTGK4210 | 5.63E+06 | 5.27E+06 ± 0.51E+06 | 3.81E+05 | 3.90E+05 ± 0.13E+05 |
| pTGK4210 | 4.92E+06 | | 4.00E+05 | |
| pTGK4228 | 8.61E+06 | 6.80E+06 ± 2.56E+06 | 8.69E+05 | 8.11E+05 ± 0.83E+05 |
| pTGK4228 | 4.98E+06 | | 7.52E+05 | |
| pTJN6-23 | 2.71E+07 | 1.74E+07 ± 0.66E+07 | 3.00E+06 | 2.97E+06 ± 0.18E+06 |
| pTJN6-23 | 1.49E+07 | | 2.70E+06 | |
| pTJN6-23 | 1.26E+07 | | 3.08E+06 | |
| pTJN6-23 | 1.50E+07 | | 3.09E+06 | | b. Relative amounts of the N-acetylglucosamine oligomer GlcNAc3 in roots and leaves of *Arabidopsis* plants transformed with pTJN6 (NODC with heterologous Golgi signal anchor sequence) and with pTGK42 (NODC without heterologous Golgi signal anchor sequence; see WO2006/136351) expressed per mg of tissue.

| WT | 3.62E+03 | 2.33E+03 ± 1.83E+03 | — | — |
| WT | 1.03E+03 | | — | |
| WT | — | | — | |
| WT | — | | — | |
| pTGK4210 | 3.13E+05 | 2.59E+05 ± 0.75E+05 | 1.69E+04 | 2.21E+04 ± 0.73E+04 |
| pTGK4210 | 2.06E+05 | | 2.73E+04 | |

TABLE 2-continued

| | Roots | | Leaves | |
|---|---|---|---|---|
| Construct | area 552 peak | average | area 552 peak | average |
| pTGK4228 | 4.80E+05 | 3.47E+05 ± 1.88E+05 | 5.34E+04 | 4.31E+04 ± 1.44E+04 |
| pTGK4228 | 2.14E+05 | | 3.29E+04 | |
| pTJN6-23 | 1.45E+06 | 9.57E+05 ± 3.36E+05 | 2.09E+05 | 2.20E+05 ± 0.16E+05 |
| pTJN6-23 | 8.69E+05 | | 2.12E+05 | |
| pTJN6-23 | 7.06E+05 | | 2.43E+05 | |
| pTJN6-23 | 8.01E+05 | | 2.16E+05 | |

Example 4: Characterization of GlcNAc Oligomers with a Degree of Polymerisation of Up to 5 in Cell Walls of Transgenic *Arabidopsis* Plants To detect GlcNAc oligomers with a degree of polymerisation of up to 5 in *Arabidopsis* plants transformed with pTJN6 as compared to wild-type *Arabidopsis* plants, PMP-Derivatisation was performed. LC-MS analysis was performed on a Waters Acquity UPLC system (Waters Corp., Milford, Mass., USA) connected to a Synapt HDMS Q-Tof mass spectrometer (Micromass, Manchester, UK). Chromatographic separation was done on an Acquity BEH C18 column (2.1 mm×150 mm, 1.7 µm) (Waters Corp., Milford, Mass., USA) using a gradient elution. Mobile phases were composed of (A) water containing 1% ACN and 0.1% formic acid and (B) ACN containing 1% water and 0.1% formic acid. Column temperature was maintained at 40° C. and the autosampler temperature at 10° C. A flow rate of 350 µl/min was applied during the gradient elution initializing at time 0 min 5% (B), time 30 min 50% (B), time 33 min 100% (B). The eluant was directed to the mass spectrometer equipped with an electrospray ionization source and lockspray interface for accurate mass measurement. MS source parameters were as following: capillary voltage 1.5 kV, sampling cone 40V, extraction cone 4V, source temperature 120° C., desolvation temperature 350° C., cone gas flow 50 L/h, desolvation gas 550 L/h. The collision energy for the trap and transfer cell were set at 6 and 4 V, respectively. For data acquisition the dynamic range enhancement mode was activated. Full scan data was recorded in negative centroid V-mode, the mass range was set between m/z 100-1600 with a scan speed of 0.2 s/scan using Masslynx software (Waters Corp., Milford, Mass., USA). Leu-enkephalin (400 pg/µl solubilised in water/ACN, (1:1, v/v) acidified with 0.1% formic acid) was used for the lock mass calibration by scanning every 10 seconds with a scan time of 0.5 seconds, 3 scans were averaged. For MS/MS purposes, the same settings were applied, except the trap collision energy was ramped from 10 to 45 V. All solvents used were ULC/MS grade (Biosolve, Valkenswaard, The Netherlands), water was produced by a DirectQ-UV water purification system (Millipore S.A.S, Molsheim, France). FIG. 4 shows that plants expressing pTJN6-23 contain monomers, dimers, trimers, tetramers and pentamers of GlcNAc.

Example 5: Fiber Specific Expression of NODC Fused to a Golgi Signal Anchor Sequence in Cotton Transgenic cotton plants comprising a chimeric NODC gene fused to a Golgi signal anchor sequence as outlined in example 1, under control of the F286 fiber-selective promoter (which is disclosed in US2003/106097) (=pTDBI146), the Gluc1A (=pTDBI158) and Gluc1D (=pTDBI159) promoter (WO 2008/083969), the E6 promoter (U.S. Pat. No. 6,096,950) (=pTGK96) or with the expansin promoter (U.S. Pat. No. 6,566,586) (=pTDBI165) were generated using the transformation method as described in U.S. Pat. No. 6,483,013. Fibers from these transgenic cotton plants were isolated and analyzed for N-acetylglucosamine polymers by HPLC. These transgenic fibers contained up to 0.5% of glucosamine which could only be detected upon TFA hydrolysis, showing that it is part of a polymer. Fibers of untransformed lines contained less than 0.01% of GlcN. The presence of chitobiose was demonstrated in the fiber from one of the lines transformed with pTDBI158. Chitobiose was not detected in the fiber from untransformed lines. Selected lines with high levels of N-acetyl oligomers were grown in the field and lines that grow normal and form normal bolls could be selected. Fiber from these lines is used to produce yarns and fabrics with improved reactivity, such as improved dyeability. Fibers isolated from cotton bolls of transgenic plants have an increased amount of N-acetylglucosamine polymers which are evenly distributed throughout the cell wall.

Example 6: Cotton Fibers with Increased Reactivity

Transgenic cotton plants comprising a chimeric NODC gene fused to a Golgi signal anchor sequence operably linked to a fiber-specific promoter were generated as described in Example 5. Mature cotton fibers are harvested from these plants and can be stained with Congo Red or can be reacted with WGA-Alexa fluor 555. In addition, the resulting mature cotton fibers can be stained with commercial dyes including cotton reactive dyes (e.g. Reactive Red 120, Levafix Blue CA), acid dyes (Acid Orange 7, Acid Blue 281) and wool reactive dyes (e.g. Reactive Red 116, Realan Amber EHF).

WGA-Alexa 555 Staining

Cotton fibers do not need to be dehydrated or permeabilized. Instead, lipids and waxes are removed by treating the fibers for 3 times 10 minutes in a chloroform: methanol mixture (1:1), follow by twice a treatment of 10 minutes in acetone and twice 5 minutes in ether. The fibers are allowed to air dry.

Fibers can be stained with either WGA-Alexa555, WGA-Alexa488 or WGA-tetramethylrhodamine.

The fibers are placed in blocking solution (150 mM NaCl, 10 mM sodiumphosphate buffer pH 7.4; 0.1% Tween 20 and 1% bovine serum albumin) and are incubated for one hour. Thereafter, the buffer is replaced by the same buffer containing WGA-fluorochrome and incubated for 4 hrs. The WGA-fluorochrome solution is replaced by blocking solution, washed 10 minutes, followed by 3 times 10 min washing with blocking solution without BSA, and 2 times 5 min washing with blocking solution without BSA and without Tween. The stained fibers are mounted on a microscope slide and evaluated by means of fluorescence microscopy (Axioplan 2 (Zeiss, Jena, Germany) using Filterset 38 (exitation: BP470/40; emission: BP525/50) for Alexa fluor 488 conugate or Filterset 20 (exitation: BP546/12; emission: BP575-640) for Alexa fluor 555 or tetramethylrhodamine conjugate. Whereas no specific fluorescence can be detected in cotton fibers from non-transgenic cotton plants, a bright fluorescence is detectable in cotton fibers from transgenic cotton plants comprising a chimeric NODC gene fused to a Golgi signal anchor sequence. Virtual microscopic sections of the cotton fibers show that the WGA-fluor555 is evenly distributed throughout the secondary cell wall of the cotton fiber cells.

To prepare for dyeing, fiber was treated for 30 min at 80° C. with distilled water containing 1 g/l sodium carbonate and 1 g/l Sandozin NIN (non-ionic detergent) followed by drying. Fiber was dyed using a liquor:fiber ratio of 50:1 with 2% omf Acid Blue 62 for 60 min at 98° C. After dyeing, fibre samples were rinsed with cold water and dried at ambient conditions. Exhaustion was determined by measuring dye concentration of the dye bath before and after dyeing using a spectrophotometer.

As can be seen on the example of a cotton line transformed with T-DNA vector pTDBI158, fiber dyed with Acid Blue 62 according to the protocol above shows an increased exhaustion level.

|  | transgene | % exhaustion at pH 4 | % exhaustion at pH 7 |
| --- | --- | --- | --- |
| G4GH396-35101 HH | gfa-nodc | 23.9 | 18.7 |
| G4GH396-35101 wt | none | 16.3 | 13.0 |

The invention claimed is:

1. A method for production of positively charged oligosaccharides in the secondary cell wall of a plant cell, said method comprising
   a. introducing or providing a chimeric gene in the plant cell, said chimeric gene comprising:
      a. a plant-expressible promoter;
      b. a DNA region coding for a Nodulation C protein fused to a heterologous signal anchor sequence for targeting to the membranes of the Golgi-apparatus; and
      c. a transcription termination and polyadenylation region
   b. regenerating said plant cell into a plant
   wherein said incorporation of positively charged oligosaccharides in cell walls from plants is increased when compared to cell walls from plants expressing a Nodulation C protein not fused to said heterologous signal anchor sequence for targeting to the membranes of the Golgi apparatus and wherein the root length of said plant is essentially the same as that of a wild-type plant not comprising the Nodulation C protein.

2. A method for production of positively charged oligosaccharides in the secondary cell wall of a plant cell, said method comprising
   a. introducing or providing a chimeric gene in the plant cell, said chimeric gene comprising:
      i. a plant-expressible promoter;
      ii. a DNA region coding for a Nodulation C protein fused to a heterologous signal anchor sequence for targeting to the membranes of the Golgi-apparatus; and
      iii. a transcription termination and polyadenylation region;
   b. regenerating said plant cell into a plant, and
   c. isolating the plant cell wall or fibers from said plant;
   wherein said incorporation of positively charged oligosaccharides in cell walls from plants is increased when compared to cell walls from plants expressing a Nodulation C protein not fused to said heterologous signal anchor sequence for targeting to the membranes of the Golgi apparatus and wherein the root length of said plant is essentially the same as that of a wild-type plant not comprising the Nodulation C protein.

3. A plant comprising the chimeric gene as described in claim 1, having an increased incorporation of positively charged oligosaccharides in their cell walls when compared to cell walls from plants expressing a Nodulation C protein not fused to said heterologous signal anchor sequence for targeting to the membranes of the Golgi apparatus and having a root length essentially the same as that of a wild-type plant not comprising the Nodulation C protein.

4. The plant of claim 3, which is cotton.

5. The method of claim 1, wherein said positively charged oligosaccharides consist of β1-4 linked N-acetylglucosamines with a degree of polymerisation of 2 to 10.

6. The method of claim 1, wherein said signal anchor sequence is the signal anchor sequence of β1,2-xylosyltransferase from *Arabidopsis thaliana*, and/or wherein said nodulation C protein comprises the amino acid sequence of SEQ ID NO: 1.

7. The method of claim 1, wherein said Nodulation C fused to the Golgi signal anchor sequence comprises the amino acid sequence of SEQ ID NO: 11.

8. The method of claim 1, wherein said plant-expressible promoter is a fiber-specific promoter.

9. The method of claim 1, wherein said plant is selected from cotton, hemp or flax, and wherein said plant cell wall in said cotton plant optionally comprises fibers.

10. The method of claim 1, wherein said plant-expressible promoter is a fiber-specific promoter selected from the fiber-specific promoter of a beta tubulin gene from cotton, a fiber-specific promoter from an actin gene from cotton, a fiber specific promoter from a lipid transfer protein gene from cotton, a promoter from the seed coat and fiber-specific protease from cotton, a promoter from fiber-specific R2R3 MYB gene from cotton, a promoter from an expansin gene from cotton or a promoter from a chitinase gene in cotton.

11. The method of claim 1, wherein the cell wall of said plant is a secondary plant cell wall.

* * * * *